US011924152B2

(12) United States Patent
Gao et al.

(10) Patent No.: US 11,924,152 B2
(45) Date of Patent: Mar. 5, 2024

(54) MESSAGING SELECTION SYSTEMS IN NETWORKED ENVIRONMENTS

(71) Applicant: Click Therapeutics, Inc., New York, NY (US)

(72) Inventors: Adam Gao, New York, NY (US); Michael Brandon Ng, New York, NY (US); Christopher Mark Jordan, New York, NY (US); Victor Gao, New York, NY (US); Adam Berger, Woodcliff Lake, NJ (US)

(73) Assignee: Click Therapeutics, Inc., New York, NY (US)

( * ) Notice: Subject to any disclaimer, the term of this patent is extended or adjusted under 35 U.S.C. 154(b) by 0 days.

(21) Appl. No.: 17/569,843

(22) Filed: Jan. 6, 2022

(65) Prior Publication Data

US 2022/0131824 A1    Apr. 28, 2022

Related U.S. Application Data

(63) Continuation of application No. 16/851,485, filed on Apr. 17, 2020, now Pat. No. 11,233,759.
(Continued)

(51) Int. Cl.
*H04L 51/212* (2022.01)
*G06N 5/04* (2023.01)
(Continued)

(52) U.S. Cl.
CPC ............ *H04L 51/212* (2022.05); *G06N 5/04* (2013.01); *G06N 20/00* (2019.01); *G06Q 30/0246* (2013.01); *H04L 51/043* (2013.01); *H04L 51/18* (2013.01); *H04L 67/306* (2013.01); *H04L 67/535* (2022.05); *H04L 67/55* (2022.05)

(58) Field of Classification Search
CPC ..... H04L 51/212; H04L 51/043; H04L 51/18; H04L 67/306; H04L 67/55; H04L 67/535
See application file for complete search history.

(56) References Cited

U.S. PATENT DOCUMENTS

| 10,242,381 B1 | 3/2019 | Zappella et al. |
| 2013/0325755 A1 | 12/2013 | Arquette et al. |

(Continued)

FOREIGN PATENT DOCUMENTS

CN    108352006 A    7/2018

OTHER PUBLICATIONS

International Preliminary Report for PCT Appl. No. PCT/US2020/028527, dated Sep. 28, 2021.
(Continued)

*Primary Examiner* — Ryan J Jakovac
(74) *Attorney, Agent, or Firm* — Foley & Lardner LLP

(57) ABSTRACT

Users of personalized messaging systems can encounter message fatigue, thereby reducing the efficacy of a message on its intended recipient. Message fatigue can result in wasted computational resources and bandwidth as messages transmitted over a network to the user's client device are not acted upon at the client device. For applications involving desired user interactions and responses, personalized messaging can be a tool to achieve user engagement targets. The systems and methods presented herein may address several of the technical challenges with personalized messaging.

20 Claims, 21 Drawing Sheets

Related U.S. Application Data

(60) Provisional application No. 62/835,267, filed on Apr. 17, 2019, provisional application No. 62/835,271, filed on Apr. 17, 2019.

(51) Int. Cl.
  *G06N 20/00* (2019.01)
  *G06Q 30/0242* (2023.01)
  *H04L 51/043* (2022.01)
  *H04L 51/18* (2022.01)
  *H04L 67/306* (2022.01)
  *H04L 67/50* (2022.01)
  *H04L 67/55* (2022.01)

(56) References Cited

U.S. PATENT DOCUMENTS

| | | |
|---|---|---|
| 2014/0273978 A1 | 9/2014 | Van Snellenberg |
| 2016/0255139 A1 | 9/2016 | Rathod |
| 2016/0269347 A1 | 9/2016 | Arquette et al. |
| 2017/0208021 A1 | 7/2017 | Ingram et al. |
| 2018/0075219 A1 | 3/2018 | Klein et al. |
| 2018/0181873 A1 | 6/2018 | Chen |
| 2019/0089194 A1* | 3/2019 | Okita ............... H02J 3/003 |
| 2019/0124023 A1* | 4/2019 | Conroy ............. G06N 5/003 |

OTHER PUBLICATIONS

International Search Report and Written Opinion of the International Searching Authority on PCT/US2020/028527 dated Aug. 3, 2020.

International Search Report on PCT PCT/US2020/028529 dated Aug. 3, 2020.

Non-Final Office Action on U.S. Appl. No. 16/851,485 dated Feb. 23, 2021.

Written Opinion on PCT/US2020/028529 dated Oct. 22, 2020.

First CN Office Action on CN Appl. No. 202080044537.1, dated Feb. 22, 2023.

* cited by examiner

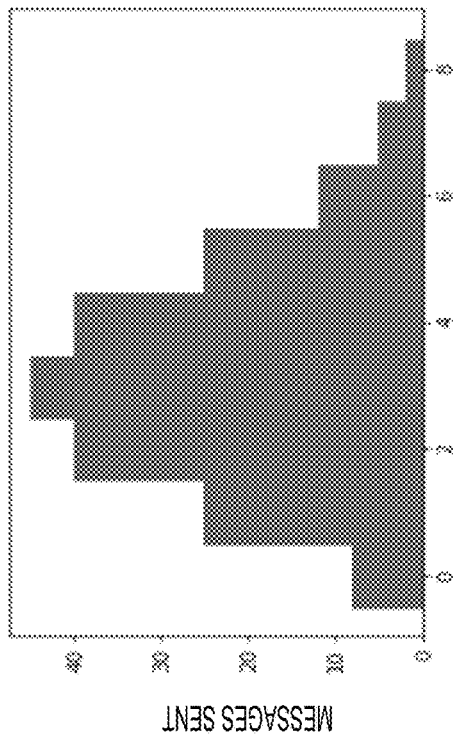
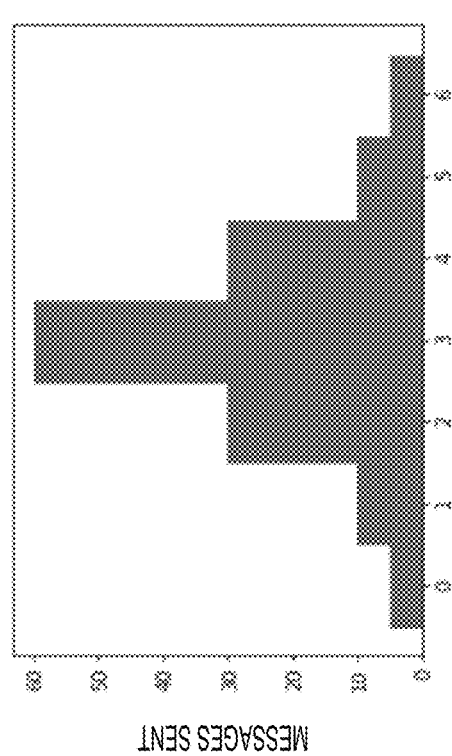

MESSAGING SELECTION SYSTEMS IN NETWORKED ENVIRONMENTS

CROSS REFERENCE TO RELATED APPLICATIONS

The present application claims priority under priority under 35 U.S.C. § 120 as a continuation of U.S. patent application Ser. No. 16/851,485, titled "MESSAGING SELECTION SYSTEMS IN NETWORKED ENVIRONMENTS," filed Apr. 17, 2020, which claims priority under priority under 35 U.S.C. § 119(e) to U.S. Provisional Patent Application No. 62/835,267, titled "MESSAGE SELECTION AND TRANSMISSION BASED ON CONFIDENCE VALUES AND COOL DOWN FACTORS IN A NETWORKED ENVIRONMENT," filed Apr. 17, 2019 and U.S. Provisional Patent Application No. 62/835,271, titled "INDIRECT UPDATES TO MESSAGING SYSTEMS IN A NETWORKED ENVIRONMENT," filed Apr. 17, 2019, each of which are incorporated herein by reference in their entirety.

BACKGROUND

Users of customized messaging systems can encounter message fatigue, thereby reducing the efficacy of a message on its intended recipient. Message fatigue can result in wasted computational resources and bandwidth as messages transmitted over a network to the user's client device are not acted upon at the client device. For applications involving desired user interactions and responses, customized messaging can be a tool to achieve user engagement targets.

SUMMARY

The present disclosure describes systems and methods for message selection and transmission based on confidence values and cool down factors. The messaging system can send relevant messages to a user at relevant times. The personalized messaging system can increase user engagement and efficacy of an application. Appropriate content delivered at the right time, tailored for each user, can have a positive effect on a user's engagement with application. Personalized and relevant messages delivered in a timely manner to each user through an application can translate to real-world actions undertaken by the user to improve health, wellbeing, fitness and overall quality of life.

To address some of the challenges associated with message fatigue as well as other related challenges, the present disclosure relates to a message selection system that can invoke a plurality of message objects, which, when invoked, can generate a plurality of messages. The message selection system can generate a confidence value for each of the messages and use the confidence value associated with each message to select one or more messages to send to the application of the client device. The message selection system can adjust the confidence values associated with each of the selected messages based on a cool down factor. The message selection system can use the cool down factor to adjust the confidence values of each of the selected messages based on various factors including but not limited to an amount of time since the last message was received by a client device, the total number of messages a user of the client device elects to receive within a predetermined time period, and a length of time the user of the client device is awake or active. The message selection system can then, based on the adjusted confidence values of each of the selected messages, make a determination to send one or more of the selected messages based on the adjusted confidence values.

The message selection system can select messages based on a likelihood that the message is going to achieve a desired endpoint or target value while adjusting the likelihood based on a time since the last message was delivered to the client device so as to reduce the likelihood that a user will experience message fatigue. The message selection system can reduce the likelihood that a user will experience message fatigue by selectively transmitting or sending a message to the client device of the user based upon a likelihood that the message will have an intended effect. Because the number and frequency of messages that cause individual users to experience message fatigue can vary, the message selection system can incorporate information about each user's message preferences, application engagement, and responses to similar messages to build a framework or model for delivering personalized messages at appropriate times.

The messages sent by the message selection system to respective client devices of users can be opened via an application executing on the respective client devices. The application executing on the client device can display a message from the message selection system to a user of the client device, prompting the user to perform an action or to elicit a user response. The application can be configured to provide information back to the message selection system including data corresponding to when messages were received at the client device, when the application displayed the message, activity performed on the application by the user, activity performed by the user on the client device, among others. The message selection system can use the information collected or received from the client device of the user to evaluate the effectiveness of the message in getting the user to perform an action or the content and timing of the user response to improve the personalization of the messages sent to individual users or in some embodiments, to monitor the user and their behavior to the messages.

In certain embodiments, the message selection system can maintain user profiles for a plurality of users. For each user profile, the message selection system can execute an invocator which can invoke message objects at predetermined time intervals. Each message object can generate a candidate message using a message template that is a candidate for transmission to the client device associated with the user profile. A message object evaluator of the message selection system can incorporate contextual data into a model of the message object to output a confidence value associated with the candidate message generated by the message object. The confidence value can be indicative of the likelihood that a candidate message sent to a user will have an intended effect. The message object evaluator can output a confidence value for message objects that satisfy certain constraints. The message object evaluator can evaluate the confidence values associated with each of the candidate messages based on certain conditions, update the confidence value based on a cool down factor and determine to send the candidate message to the client device if the updated confidence value crosses a predetermined threshold.

The message selection system can receive response data from a reporting agent of the application executing on the client device associated with the user profile. A response evaluator of the message selection system can incorporate the response data into the models of the message objects so as to improve the performance of the models based on response data corresponding to previous messages sent to the client device. The response data can be compared against target values (or desired endpoints) of the message objects to improve the models of the message objects. In this way, the message selection system can learn from a user's message preferences and responses and improve the selection process of future candidate messages as well as improve the quality of the confidence values computed for the future candidate messages. By doing so, the message selection system can select and send fewer messages to the client device of the user while at the same time increasing the likelihood that the user will engage or respond to the message and achieve the desired endpoint of the message.

According to at least one aspect of the disclosure, a method can include identifying, by one or more processors, a plurality of users and a plurality of message objects. The method can include retrieving, by one or more processors, contextual data for each of the plurality of users for one or more message objects. The method can include generating, by one or more processors, candidate messages based on the one or more message objects and contextual data. The method can include updating, by one or more processors, the confidence value for each of the candidate messages based on a cool down factor to generate an updated confidence value. The method can include selecting, by one or more processors, a candidate message based on the updated confidence value. The method can include transmitting, by one or more processors, the selected candidate message based on the updated confidence value crossing a predetermined threshold.

The present disclosure describes system and methods for indirect updates to models of messages objects of a messaging system. The messaging system uses responses to non-rhetorical messages to update models of message objects associated with non-rhetorical messages. Because rhetorical messages do not elicit a response from the user, the messaging system may not be able to update the models of message objects associated with rhetorical messages. A lack of response from the user who receive the rhetorical message does not provide information pertaining to the effectiveness or ineffectiveness of the rhetorical message. Additionally, without a response from the user, the messaging system may not be able to quantify the benefit that rhetorical messages have on the user.

To address some of the challenges associated with a lack of response data from rhetorical messages, the present disclosure relates to indirect updates to models of messages objects of a message selection system. The message selection system can include a response evaluator that can incorporate the response data of models of message objects associated with non-rhetorical messages into models of message objects associated with rhetorical messages. In this way, the message selection system can use the response data of non-rhetorical messages as a proxy for the response data (or lack thereof) of rhetorical messages. By doing so, the message selection system can select and transmit customized rhetorical messages to the client device of the user, even though the message selection system does not receive direct feedback regarding the rhetorical messages. The message selection system can also transmit rhetorical messages to the client device of the user at a customized time to prevent message fatigue.

The message selection system can select messages based on a likelihood that the message is going to achieve a desired endpoint or target value while adjusting the likelihood based on a time since the last message was delivered to the client device so as to reduce the likelihood that a user will experience message fatigue. The message selection system can reduce the likelihood that a user will experience message fatigue by selectively transmitting or sending a message to the client device of the user based upon a likelihood that the message will have an intended effect. Because the number and frequency of messages that cause individual users to experience message fatigue can vary, the message selection system can incorporate information about each user's message preferences, application engagement, and responses to similar messages to build a framework or model for delivering customized messages at appropriate times.

The messages sent by the message selection system to respective client devices of users can be opened via an application executing on the respective client devices. The application executing on the client device can display a message from the message selection system to a user of the client device, prompting the user to perform an action or to elicit a user response. The application can be configured to provide information back to the message selection system including data corresponding to when messages were received at the client device, when the application displayed the message, activity performed on the application by the user, activity performed by the user on the client device, among others. The message selection system can use the information collected or received from the client device of the user to evaluate the effectiveness of the message in getting the user to perform an action or the content and timing of the user response to improve the personalization of the messages sent to individual users or in some embodiments, to monitor the user and their behavior to the messages.

In certain embodiments, the message selection system can maintain user profiles for a plurality of users. For each user profile, the message selection system can execute an invocator which can invoke message objects at predetermined time intervals. Each message object can generate a candidate message using a message template that is a candidate for transmission to the client device associated with the user profile. A message object evaluator of the message selection system can incorporate contextual data into a model of the message object to output a confidence value associated with the candidate message generated by the message object. The confidence value can be indicative of the likelihood that a candidate message sent to a user will have an intended effect. The message object evaluator can output a confidence value for message objects that satisfy certain constraints. The message object evaluator can evaluate the confidence values associated with each of the candidate messages based on certain conditions, update the confidence value based on a cool down factor and determine to send the candidate message to the client device if the updated confidence value crosses a predetermined threshold.

The message selection system can receive response data from a reporting agent of the application executing on the client device associated with the user profile. A response evaluator of the message selection system can incorporate the response data into the models of the message objects so as to improve the performance of the models based on response data corresponding to previous messages sent to the client device. The response data can be compared against target values (or desired endpoints) of the message objects to improve the models of the message objects. In this way, the message selection system can learn from a user's message preferences and responses and improve the selection process of future candidate messages as well as improve the quality of the confidence values computed for the future candidate messages. By doing so, the message selection system can select and send fewer messages to the client device of the user while at the same time increasing the likelihood that the user will engage or respond to the message and achieve the desired endpoint of the message.

The response evaluator can incorporate the response data of models of message objects associated with non-rhetorical messages into models of message objects associated with rhetorical messages. In this way, the message selection system can use the response data of non-rhetorical messages as a proxy for the response data (or lack thereof) of rhetorical messages. By doing so, the message selection system can select and transmit appropriate and personalized rhetorical messages to the client device of the user, even though the message selection system does not receive direct feedback from users upon user receipt of the rhetorical messages.

According to at least one aspect of the disclosure, a method can include identifying, by one or more processors of a server, a plurality of non-rhetorical messages. The non-rhetorical messages can include a first set of requests configured to generate a response message at a remote device to be transmitted to the server. The method can include identifying, by one or more processors of a server, a rhetorical message. The rhetorical message can include a second set of requests configured not to generate a response message at the remote device. The method can include identifying, by one or more processors of a server, a rhetorical message model. The rhetorical message model can correspond to the rhetorical message. The method can include identifying, by one or more processors of a server, a plurality of non-rhetorical message models. The non-rhetorical message models can correspond to the rhetorical message model. The method can include receiving, by one or more processors of a server, a response message to a non-rhetorical message. The method can include updating the rhetorical message model based on the received response message to the non-rhetorical message.

According to at least one aspect, the present disclose is directed to systems and methods of transmitting messages across networked environments. At least one server having one or more processors may identify a plurality of candidate message objects. Each of the plurality of candidate message objects may be associated with a selection criterion for presentation to users to achieve one or more of a plurality of endpoints. The at least one server may obtain, from an activity log for a user associated with a remote computing device, one or more actions by the user recorded via the remote computing device. The at least one server may determine, from the one or more actions recorded by the user, a user state used to identify one of the plurality of candidate message objects. The at least one server may determine, for each of the plurality of candidate message objects, a confidence value based on a comparison between the user state and the selection criterion of the candidate message object. The confidence value may indicate a predicted effectiveness of the corresponding candidate message on the user toward achieving one or more of the plurality of endpoints. The at least one server may update, for each of the plurality of candidate message objects, the confidence value based at least on an amount of time elapsed between a previous time of transmission of a previous message corresponding to at least one of the plurality of candidate message objects and a current time. The at least one server may select, from the plurality of candidate message objects, a message object based on the confidence value for the message. The at least one server may generate a message based on the message object selected from the plurality of message objects. The at least one server may transmit, to the remote computing device associated with the user, the message for presentation.

In some embodiments, the at least one server may record on the activity log, one or more subsequent actions by the user in response to the presentation of the message via the remote computing device. In some embodiments, the at least one server may update the user state based on the one or more subsequent actions in response to the presentation of the message.

In some embodiments, the at least one server may establish a message object model using a training dataset. The training dataset may include historical response data from users for messages corresponding to one or more of the plurality of candidate message objects. In some embodiments, the at least one server may apply the message object model to the user state and the selection criteria of the plurality of candidate message objects to determine the confidence value.

In some embodiments, each candidate message object of the plurality of candidate message objects may include: a message template for generating the corresponding message; a model for determining the confidence value; a constraint on a time of transmitting the corresponding message; and the selection criterion defining the one or more of the plurality of endpoints to achieve within a defined time window.

In some embodiments, the at least one server may determine, from a plurality of users states for the user associated with the remote computing device, the user state corresponding to at least one of the plurality of endpoints. In some embodiments, the at least one server may identify a cool down factor corresponding to the amount of time elapsed between the previous time of transmission and the current time to apply to the confidence value.

In some embodiments, the at least one server may select the message object from the plurality candidate message objects based on a comparison of the confidence value for the message object and a threshold value. The threshold value may be defined by a delivery policy for transmitting messages. In some embodiments, the at least one server may obtain, from the activity log for the user, the one or more actions by the users in response to presentations of previous messages corresponding to one or more of the plurality of candidate message objects.

In some embodiments, the at least one server may transmit the message to the remote computing device at the current time defined by a delivery policy for transmitting messages. In some embodiments, the at least one server may remove, from selection, at least a subset of the plurality of candidate message objects based on the user state not matching the selection criterion of each of the subset.

According to at least one aspect, the present disclosure is directed to systems and methods of selecting messages to transmit across networked environments. At least one server having one or more processors may identify a plurality of message objects. Each message object of the plurality of message objects may be associated with one or more of a plurality of endpoints to be achieved. The at least one server may determine, for each message object of the plurality of message objects, a number of users associated with a plurality of remote computing devices to which a corresponding message is presented that satisfied at least one of one or more of the plurality of endpoints of the message object. The at least one server may determine, for each message object of the plurality of message objects, a performance score for the message object based on the number of users that were presented with the corresponding message and that satisfied at least one of one or more of the plurality of behavior endpoints of the message object. The at least one server may rank the plurality of message objects based on a corresponding plurality of performance scores. The at least one server may restrict, based on the ranking of the plurality of message objects, at least a subset of the plurality of message objects from being used to generate messages for transmission to the plurality of remote computing devices.

In some embodiments, the at least server may identify the plurality of message objects of a first message type. Each message object of the plurality of message objects of the first message type may define a message template for generating a corresponding message. The corresponding message may have one or more input elements when presented on the plurality of remote computing devices.

In some embodiments, the at least server may identify a second plurality of message objects, each message object of the second plurality of message objects associated with the one or more endpoints to be achieved. In some embodiments, the at least server may select, for transmission, a subset of the second plurality of message objects based on one or more of the plurality of endpoints to be achieved associated with a remaining subset of the plurality of message objects of the first message type subsequent to removal of at least the subset.

In some embodiments, each message object of the second plurality of message objects may be of a second message type different from a first message type for the plurality of message objects. Each message object of the second plurality of message objects of the second message type may define a message template for generating a corresponding message. The corresponding message may lack any input elements when presented on the plurality of remote computing devices.

In some embodiments, for each message object of the plurality of message objects, the at least one server may identify, in each response to a message corresponding to the message object when presented on one of the plurality of remote computing devices, an input on one or more input elements of the corresponding message. In some embodiments, for each message object of the plurality of message objects, the at least one server may determine, for each response to the corresponding message, that at least one of one or more of the plurality of endpoints of the message object is satisfied based on the input on the one or more input elements of the message. In some embodiments, the at least one server may determine the number of users based on the determination, for each message object of the plurality of message, that at least one of one or more of the plurality of endpoints of the message object is satisfied.

In some embodiments, the at least one server may establish a performance model for determining performance scores using a training dataset. The training dataset may include historical response data from users for one or more of the plurality of candidate message objects. In some embodiments, the at least one server may apply the performance model to responses received from the plurality of remote computing devices responsive to the presentation of the corresponding message.

In some embodiments, the at least one server may determine, for each message object of the plurality of message objects, that at least one of one or more of the plurality of endpoints of the message object is satisfied based on an input on the one or more input elements of a message corresponding to the message object. In some embodiments, the at least one server may update a performance model for determining performance scores using the determination, for each message object of the plurality of message objects, that at least one of one or more of the plurality of endpoints of the message object is satisfied.

In some embodiments, the at least one server may attribute one or more of the plurality of endpoints to each message object of the plurality of message objects based on responses received from the plurality of remote computing devices responsive to the presentation of the corresponding message. In some embodiments, the at least one server may restrict at least the subset of the plurality of message objects based on a comparison between the performance scores and a threshold value. In some embodiments, the at least one server may permit transmission of a plurality of messages corresponding to a remaining subset of the plurality of message objects across the plurality of remote computing devices.

BRIEF DESCRIPTIONS OF THE DRAWINGS

The foregoing and other objects, aspects, features, and advantages of the disclosure will become more apparent and better understood by referring to the following description taken in conjunction with the accompanying drawings, in which:

FIGS. 6A-6C illustrate distribution of numbers of messages sent per day;

Figure 9A:
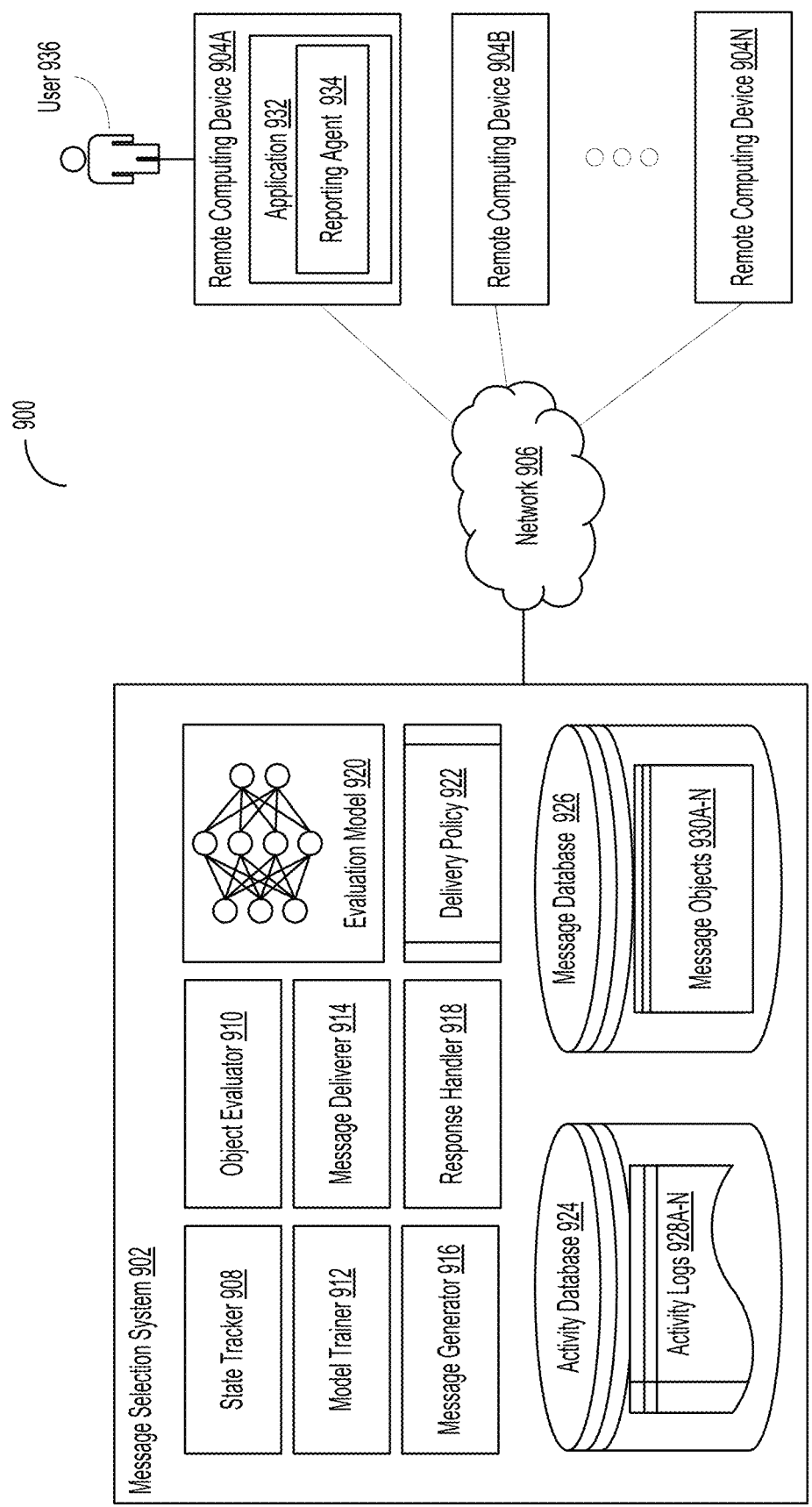
FIG. 9A illustrates a block diagram of a system for selecting and transmitting messages across networked environments using confidence values.
Figure 9B:
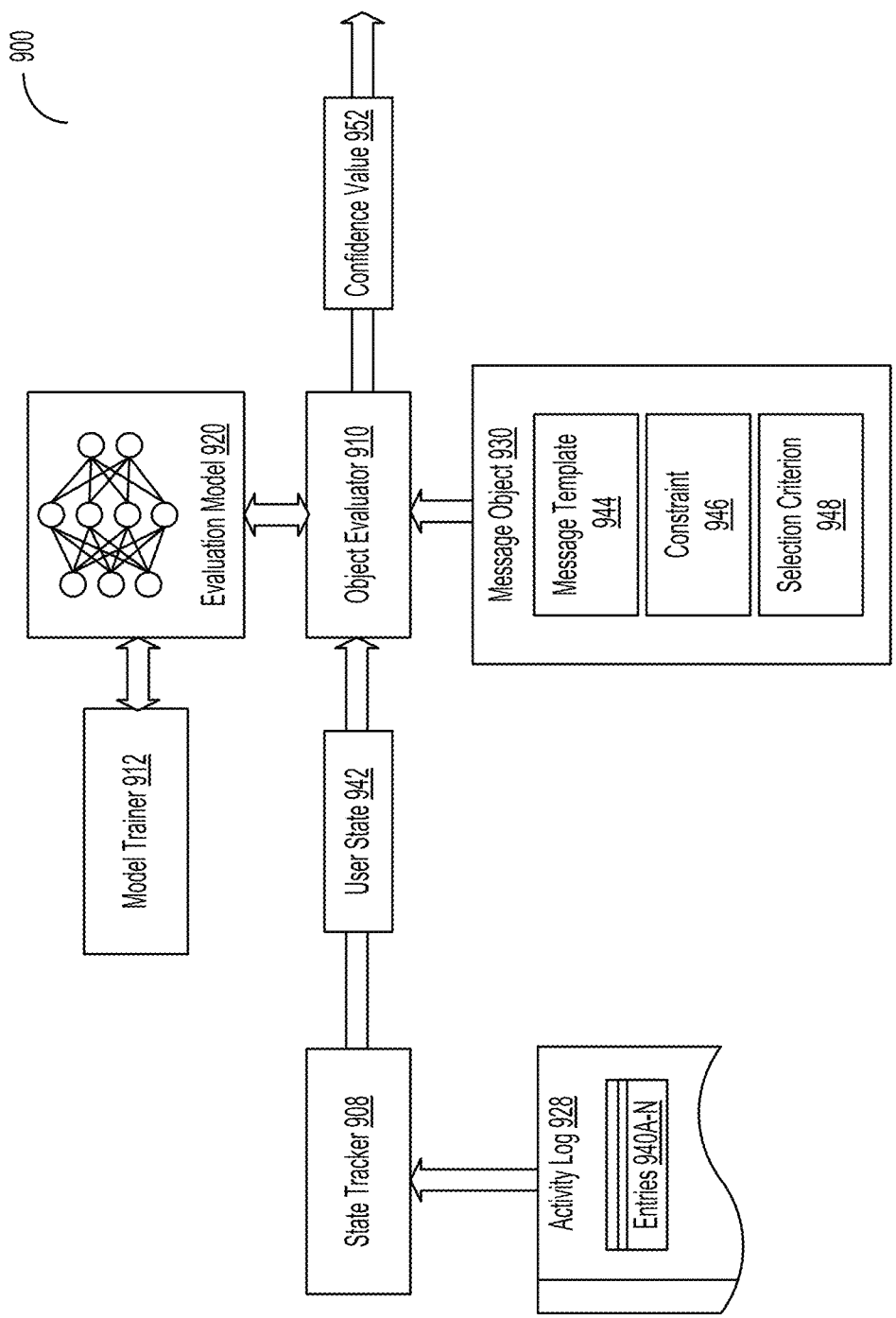
Figure 9C:
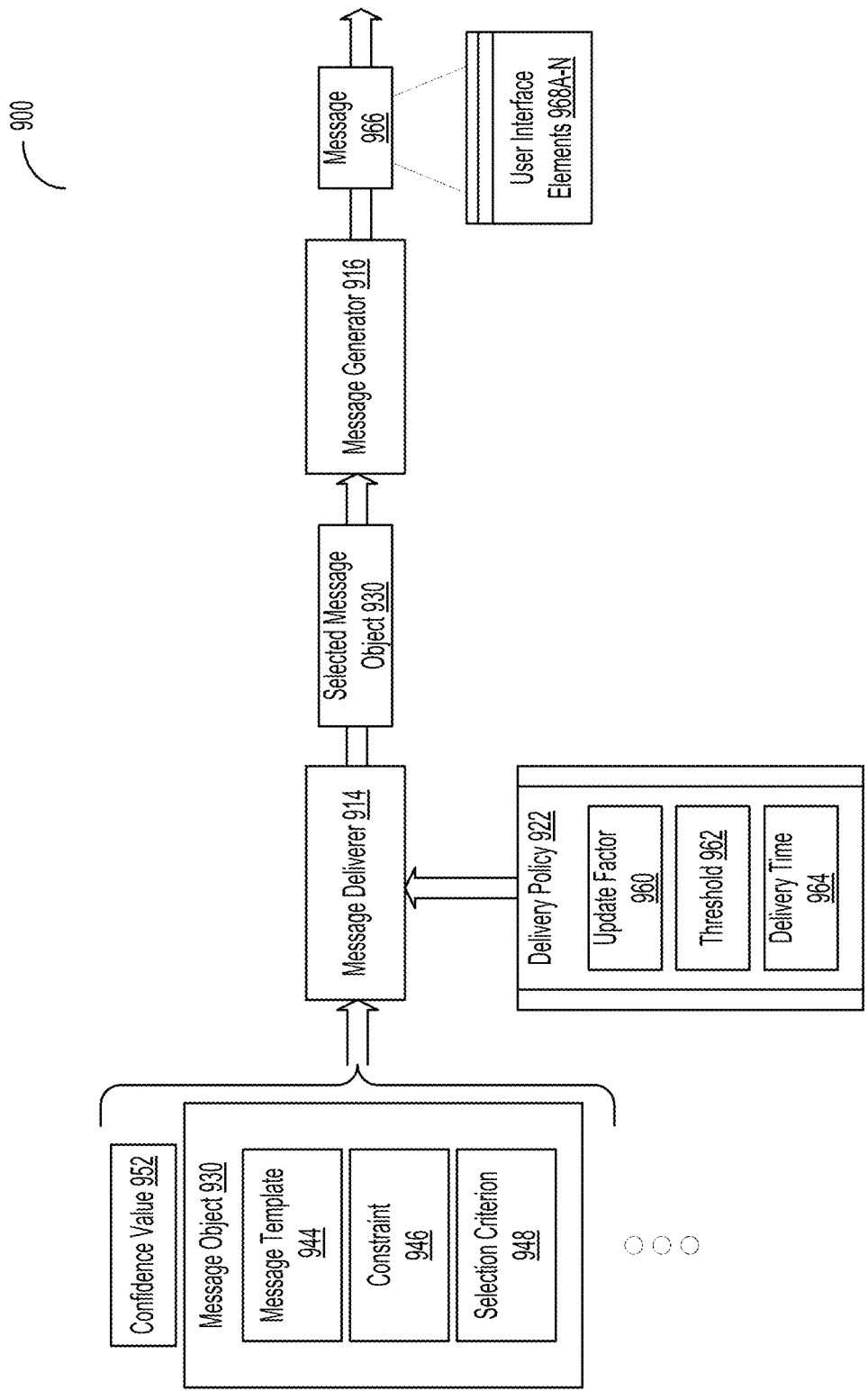
Figure 9D:
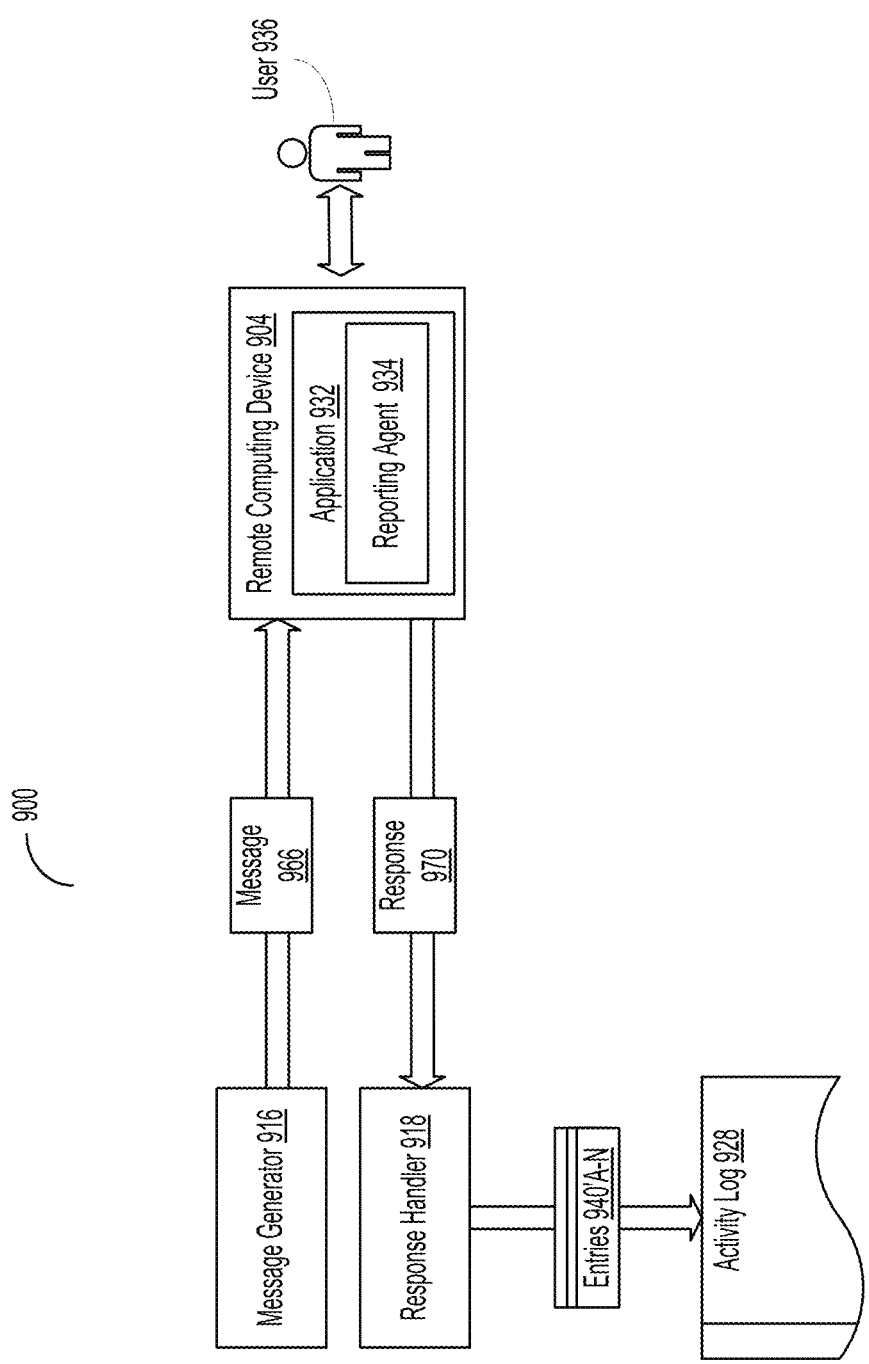
Figure 10:
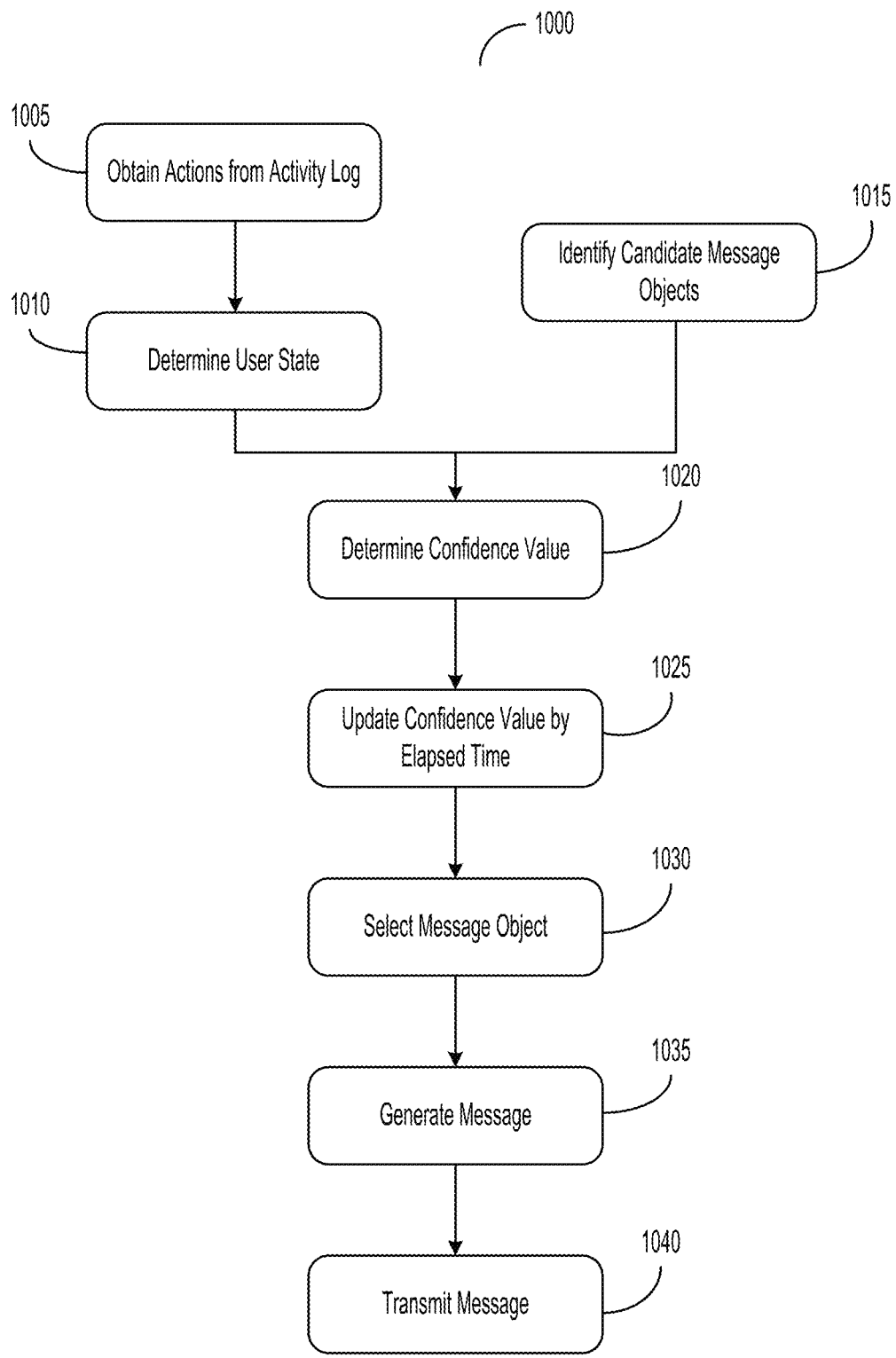
Figure 11A:
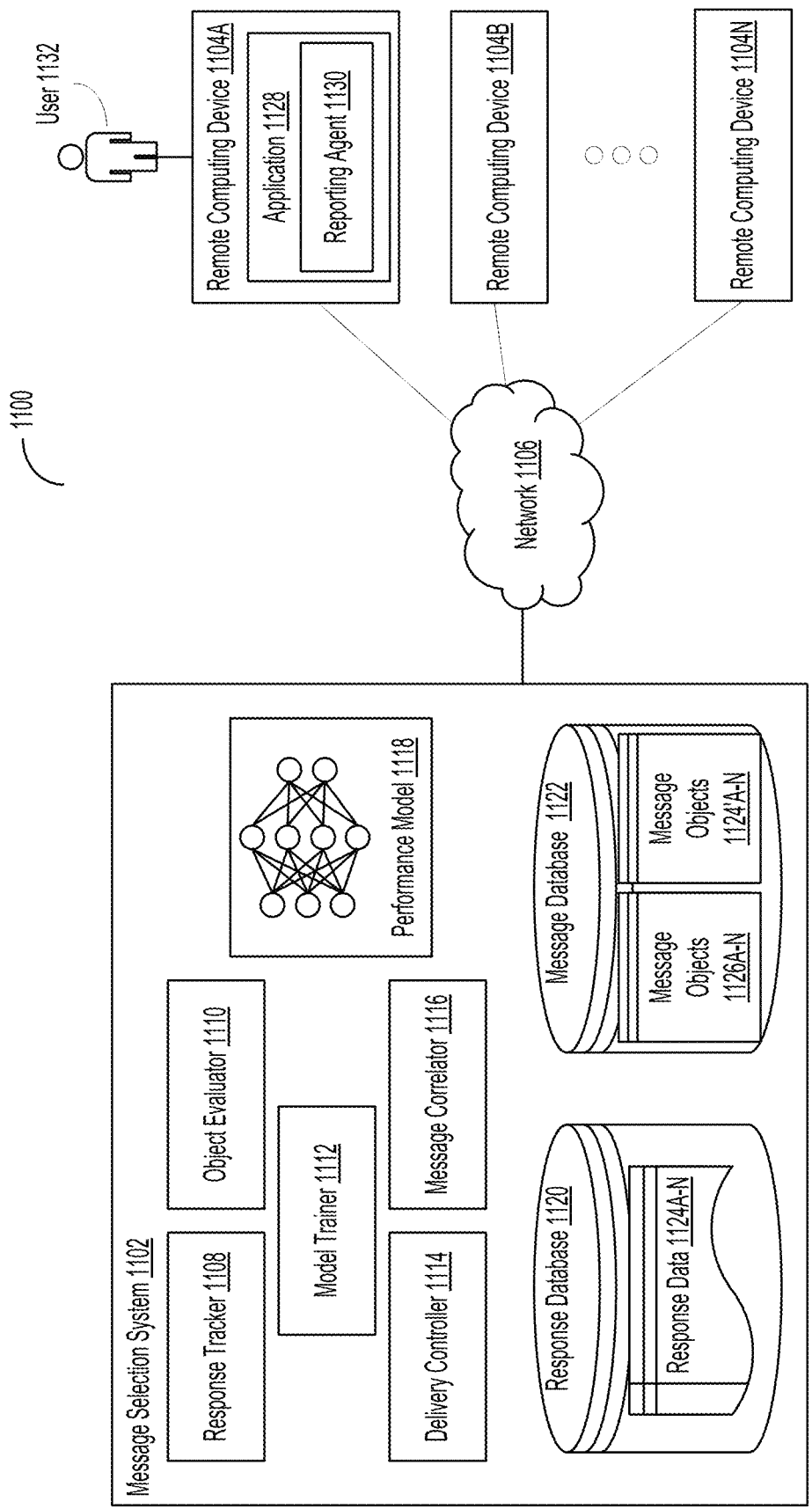
Figure 11B:
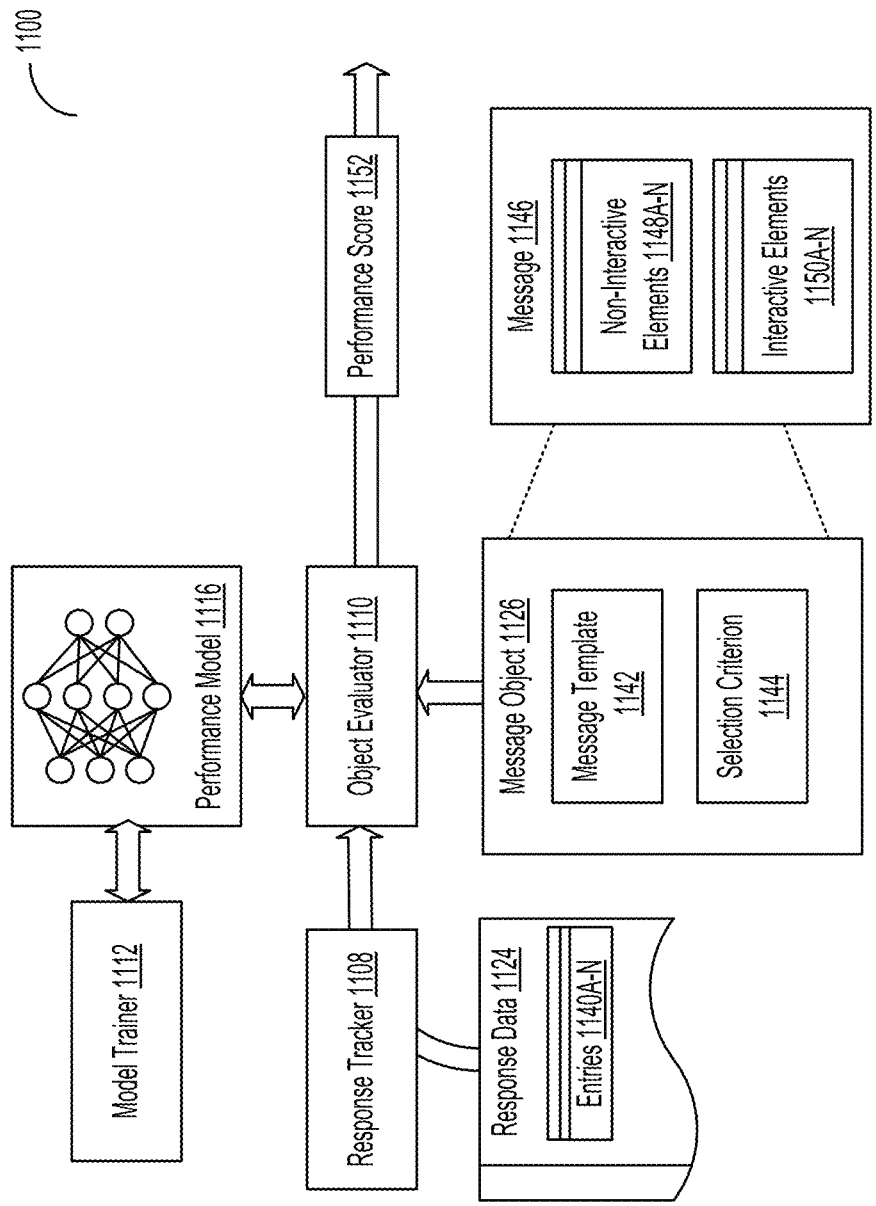
Figure 11C:
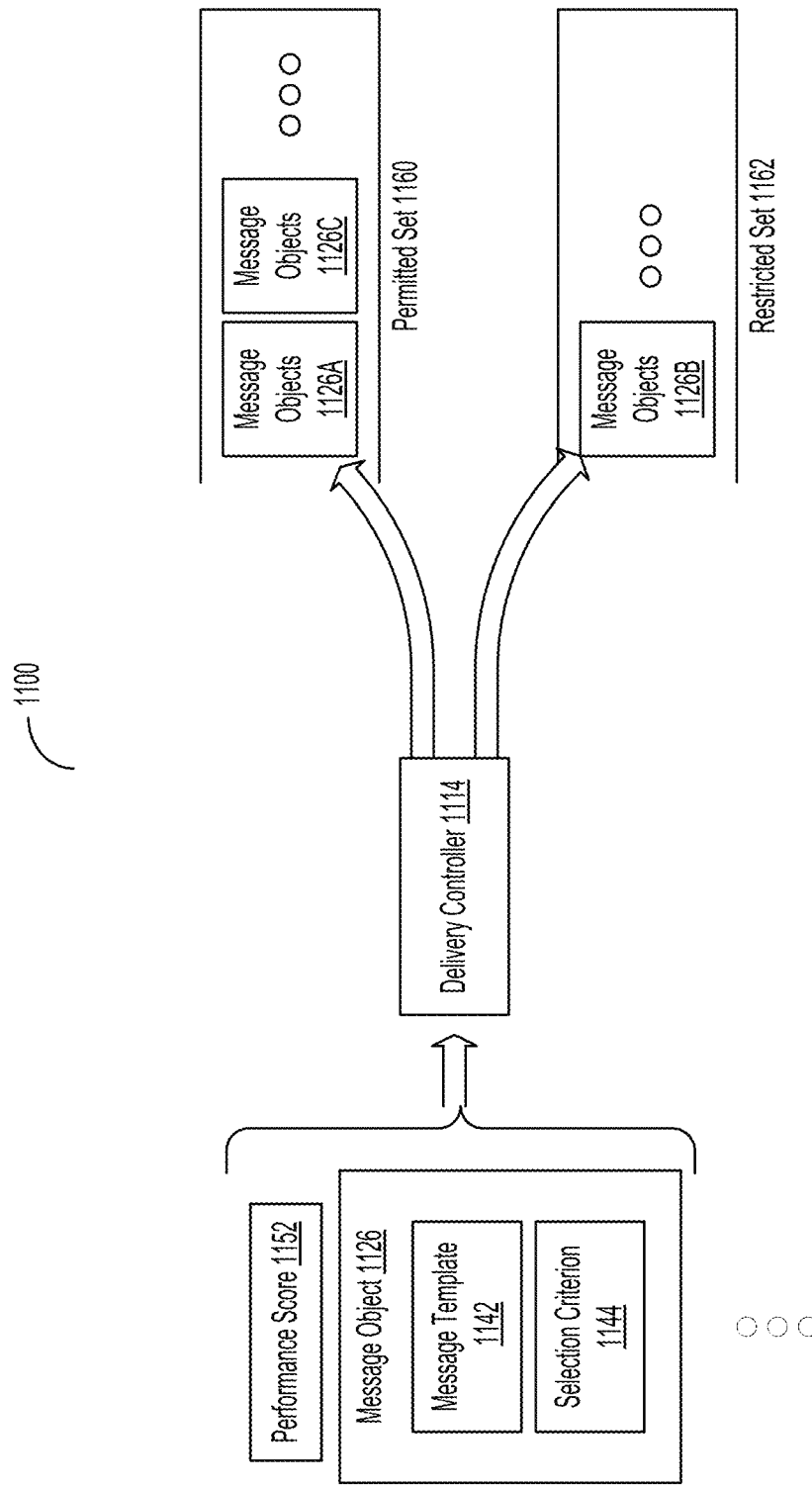
Figure 11D:
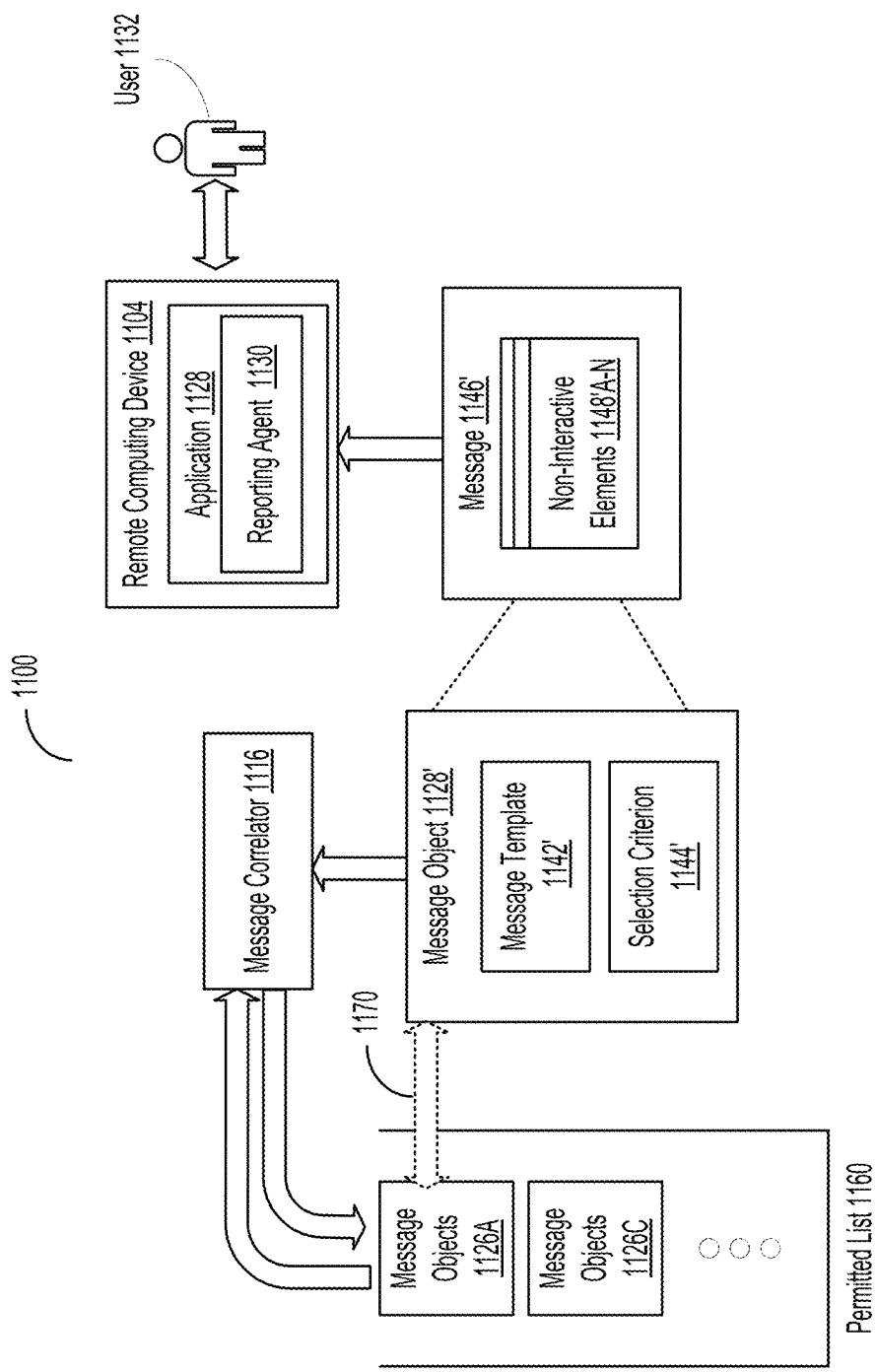
Figure 12:
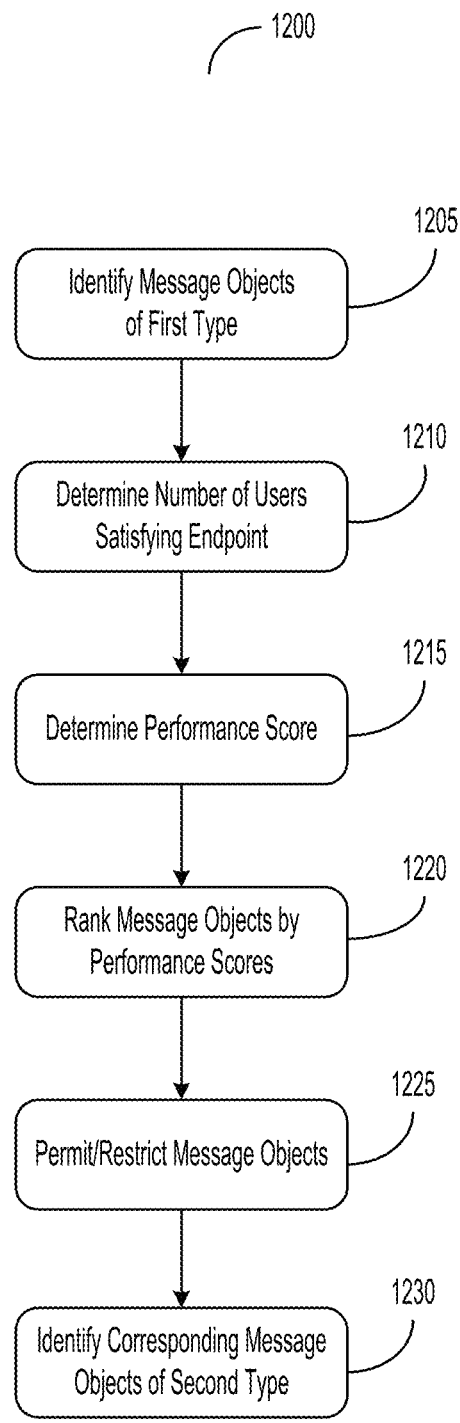

FIGS. 9B-D illustrate sequence diagrams of a system for selecting and transmitting messages across networked environments using confidence values;

FIG. 10 illustrates a flow diagram of a method of selecting and transmitting messages across networked environments using confidence values;

FIG. 11A illustrates a block diagram of a system for selecting and transmitting messages of different types across networked environments;

FIGS. 11B-D illustrate sequence diagrams of a system for selecting and transmitting messages of different types across networked environments; and FIG. 12 illustrates a flow diagram of a method of selecting and transmitting messages of different types across networked environments.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

For purposes of reading the description of the various embodiments below, the following enumeration of the sections of the specification and their respective contents may be helpful:

Section A describes a network and computing environment which may be useful for practicing embodiments described herein;

Section B describes embodiments of systems and methods for message selection and transmission based on confidence values and cool down factors in a networked environment;

Section C describes embodiments of systems and methods for indirect updates to messaging systems;

Section D describes embodiments of systems and methods of selecting and transmitting messages across networked environments using confidence values; and Section E describes embodiments of systems and methods of selecting and transmitting messages of different types across networked environments.

A. Network and Computing Environment

Figure 1A:
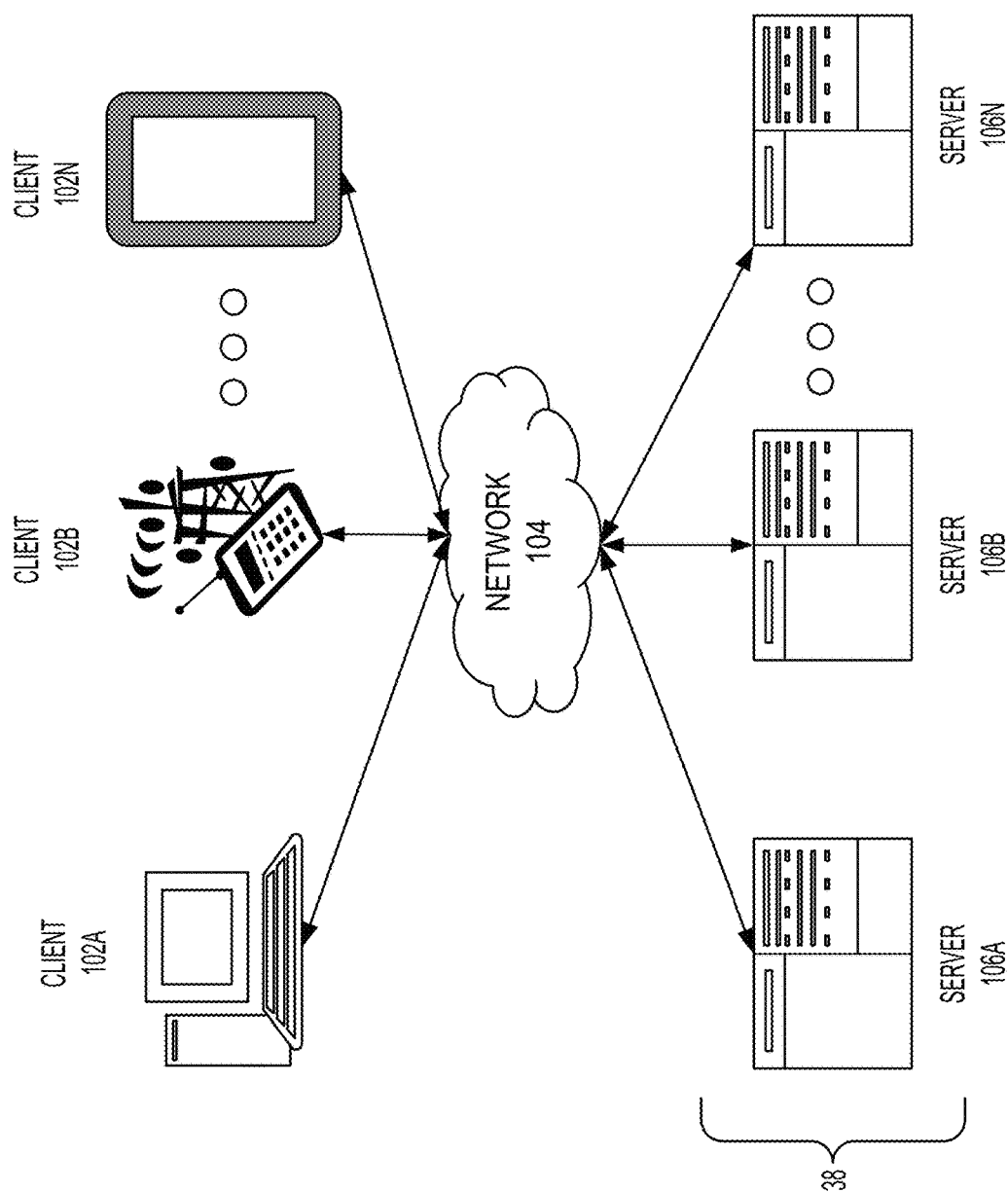
FIG. 1A illustrates a block diagram depicting an embodiment of a network environment comprising local devices in communication with remote devices.

In addition to discussing specific embodiments of the present solution, it may be helpful to describe aspects of the operating environment as well as associated system components (e.g., hardware elements) in connection with the methods and systems described herein. Referring to FIG. 1A, an embodiment of a network environment is depicted. In brief overview, the network environment includes one or more clients 102a-102n (also generally referred to as local machine(s) 102, client(s) 102, client node(s) 102, client machine(s) 102, client computer(s) 102, client device(s) 102, endpoint(s) 102, or endpoint node(s) 102) in communication with one or more servers 106a-106n (also generally referred to as server(s) 106, node 106, or remote machine(s) 106) via one or more networks 104. In some embodiments, a client 102 has the capacity to function as both a client node seeking access to resources provided by a server and as a server providing access to hosted resources for other clients 102a-102n.

Although FIG. 1A shows a network 104 between the clients 102 and the servers 106, the clients 102 and the servers 106 may be on the same network 104. In some embodiments, there are multiple networks 104 between the clients 102 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be connected via wired or wireless links. Wired links may include Digital Subscriber Line (DSL), coaxial cable lines, or optical fiber lines. The wireless links may include BLUETOOTH, Wi-Fi, Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 1G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 104 may be any type and/or form of network. The geographical scope of the network 104 may vary widely and the network 104 can be a body area network (BAN), a personal area network (PAN), a local-area network (LAN), e.g. Intranet, a metropolitan area network (MAN), a wide area network (WAN), or the Internet. The topology of the network 104 may be of any form and may include, e.g., any of the following: point-to-point, bus, star, ring, mesh, or tree. The network 104 may be an overlay network which is virtual and sits on top of one or more layers of other networks 104'. The network 104 may be of any such network topology as known to those ordinarily skilled in the art capable of supporting the operations described herein. The network 104 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 104 may be a type of a broadcast network, a telecommunications network, a data communication network, or a computer network.

In some embodiments, the system may include multiple, logically-grouped servers 106. In one of these embodiments, the logical group of servers may be referred to as a server farm 38 or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous—one or more of the servers 106 or machines 106 can operate according to one type of operating system platform (e.g., WINDOWS NT, manufactured by Microsoft Corp. of Redmond, Washington), while one or more of the other servers 106 can operate on according to another type of operating system platform (e.g., Unix, Linux, or Mac OS X).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualize physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, California; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store. Server 106 may be a file server, application server, web server, proxy server, appliance, network appliance, gateway, gateway server, virtualization server, deployment server, SSL VPN server, or firewall. In one embodiment, the server 106 may be referred to as a remote machine or a node.

Figure 1B:
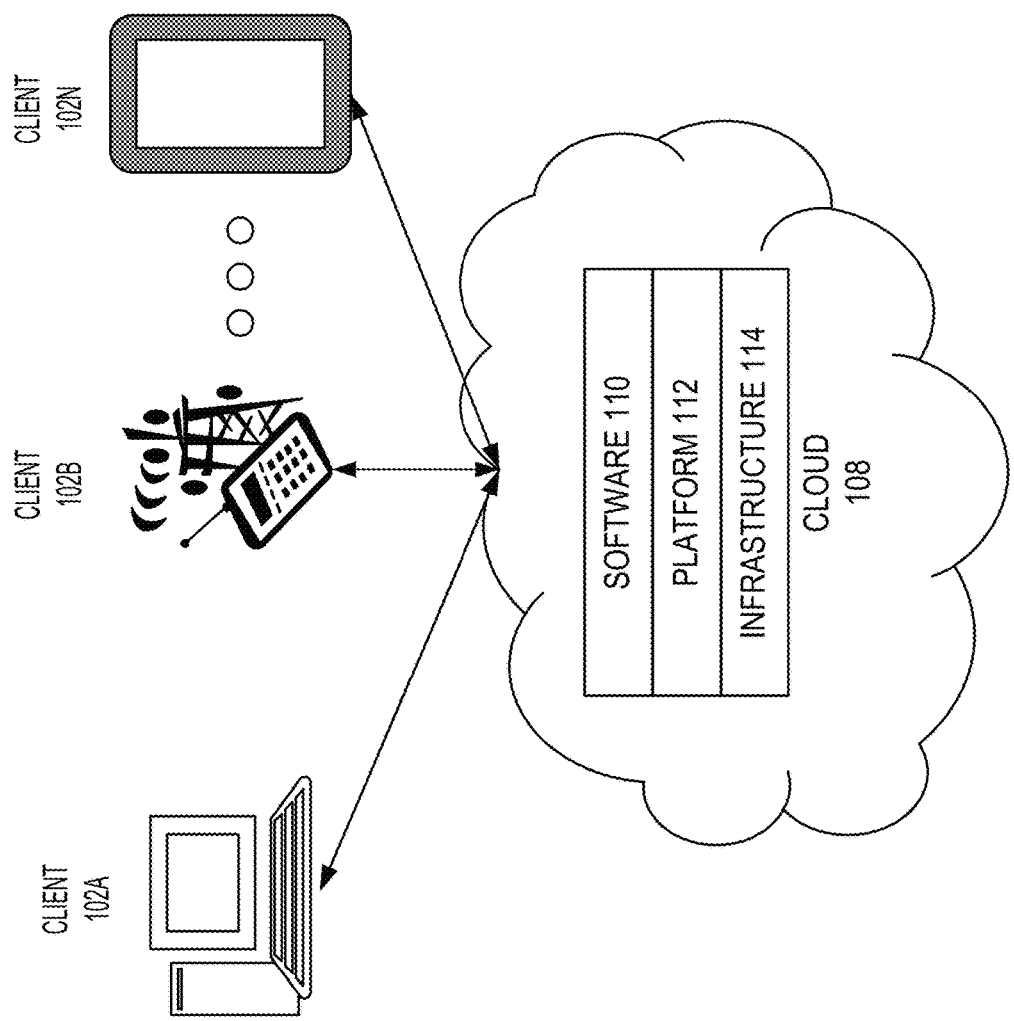
FIG. 1B-1D illustrates block diagrams depicting embodiments of computers useful in connection with the methods and systems described herein.

Referring to FIG. 1B, a cloud computing environment is depicted. A cloud computing environment may provide client 102 with one or more resources provided by a network environment. The cloud computing environment may include one or more clients 102a-102n, in communication with the cloud 108 over one or more networks 104. Clients 102 may include, e.g., thick clients, thin clients, and zero clients. A thick client may provide at least some functionality even when disconnected from the cloud 108 or servers 106. A thin client or a zero client may depend on the connection to the cloud 108 or server 106 to provide functionality. A zero client may depend on the cloud 108 or other networks 104 or servers 106 to retrieve operating system data for the client device. The cloud 108 may include back end platforms, e.g., servers 106, storage, server farms or data centers.

The cloud 108 may be public, private, or hybrid. Public clouds may include public servers 106 that are maintained by third parties to the clients 102 or the owners of the clients. The servers 106 may be located off-site in remote geographical locations as disclosed above or otherwise. Public clouds may be connected to the servers 106 over a public network. Private clouds may include private servers 106 that are physically maintained by clients 102 or owners of clients. Private clouds may be connected to the servers 106 over a private network 104. Hybrid clouds 108 may include both the private and public networks 104 and servers 106.

The cloud 108 may also include a cloud based delivery, e.g. Software as a Service (SaaS) 110, Platform as a Service (PaaS) 112, and Infrastructure as a Service (IaaS) 114. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS include AMAZON WEB SERVICES provided by Amazon.com, Inc., of Seattle, Washington, RACKSPACE CLOUD provided by Rackspace US, Inc., of San Antonio, Texas, Google Compute Engine provided by Google Inc. of Mountain View, California, or RIGHTSCALE provided by RightScale, Inc., of Santa Barbara, California PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Washington, Google App Engine provided by Google Inc., and HEROKU provided by Heroku, Inc. of San Francisco, California SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, California, or OFFICE 365 provided by Microsoft Corporation. Examples of SaaS may also include data storage providers, e.g. DROPBOX provided by Dropbox, Inc. of San Francisco, California, Microsoft SKYDRIVE provided by Microsoft Corporation, Google Drive provided by Google Inc., or Apple ICLOUD provided by Apple Inc. of Cupertino, California.

Clients 102 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 102 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 102 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, California). Clients 102 may also access SaaS resources through smartphone or tablet applications, including, for example, Salesforce Sales Cloud, or Google Drive app. Clients 102 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 1C:
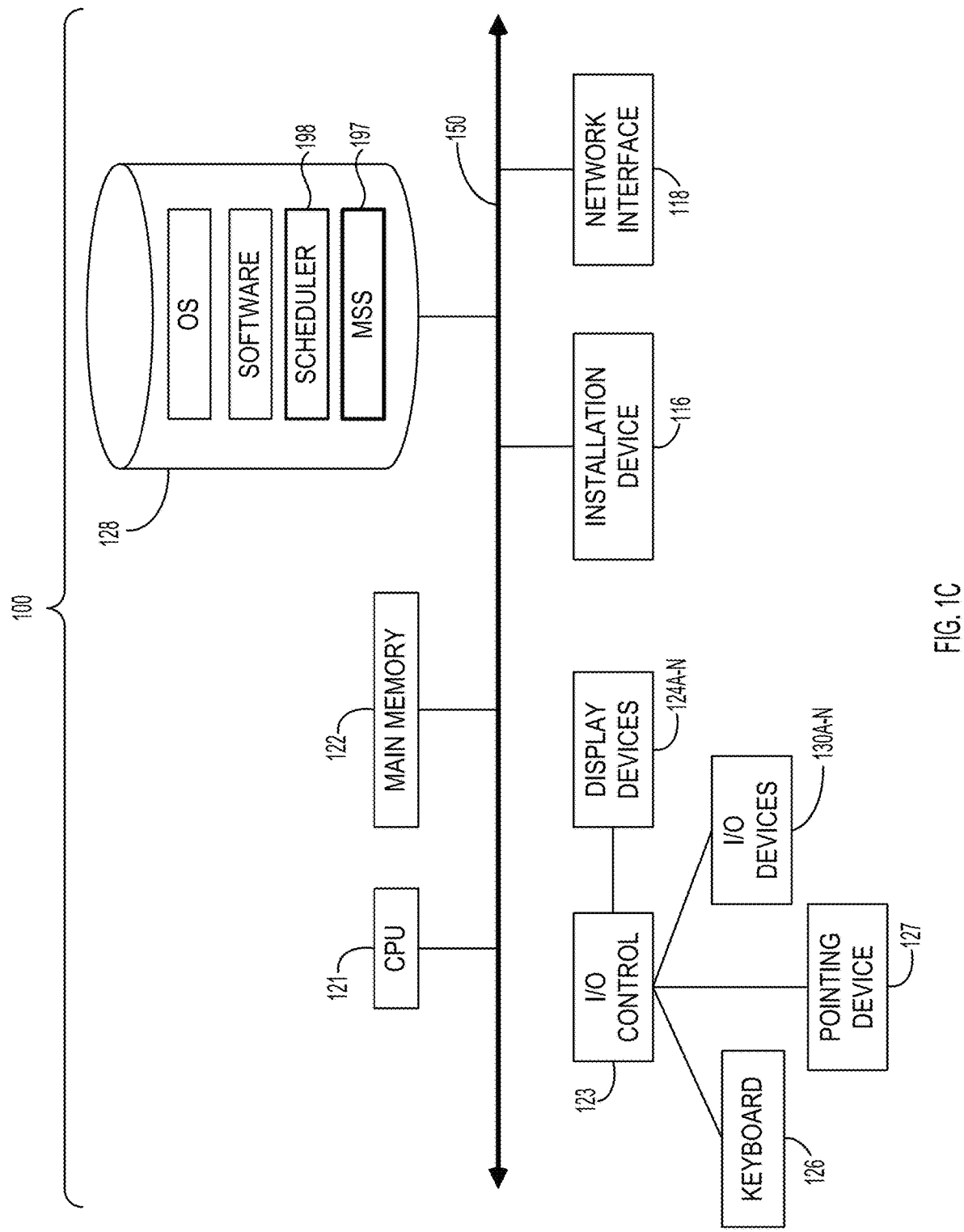
Figure 1D:
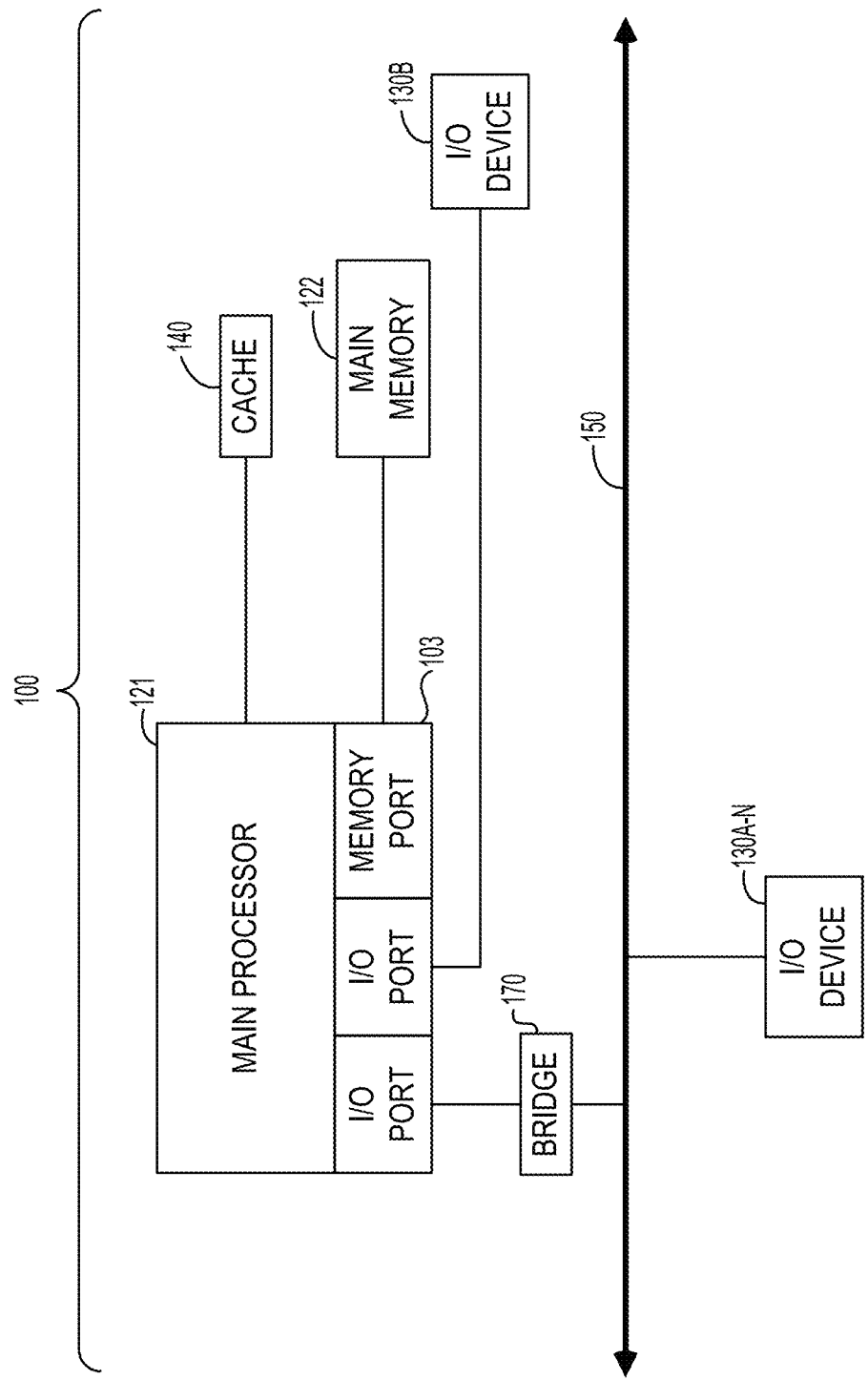

The client 102 and server 106 may be deployed as and/or executed on any type and form of computing device, e.g. a computer, network device or appliance capable of communicating on any type and form of network and performing the operations described herein. FIGS. 1C and 1D depict block diagrams of a computing device 100 useful for practicing an embodiment of the client 102 or a server 106. As shown in FIGS. 1C and 1D, each computing device 100 includes a central processing unit 121, and a main memory unit 122. As shown in FIG. 1C, a computing device 100 may include a storage device 128, an installation device 116, a network interface 118, an I/O controller 123, display devices 124a-124n, a keyboard 126 and a pointing device 127, e.g. a mouse. The storage device 128 may include, without limitation, an operating system, software, and a software of a message selection system (MSS) 197. As shown in FIG. 1D, each computing device 100 may also include additional optional elements, e.g. a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, e.g.: those manufactured by Intel Corporation of Mountain View, California; those manufactured by Motorola Corporation of Schaumburg, Illinois; the ARM processor and TEGRA system on a chip (SoC) manufactured by Nvidia of Santa Clara, California; the POWER7 processor, those manufactured by International Business Machines of White Plains, New York; or those manufactured by Advanced Micro Devices of Sunnyvale, California. The computing device 100 may be based on any of these processors, or any other processor capable of operating as described herein. The central processing unit 121 may utilize instruction level parallelism, thread level parallelism, different levels of cache, and multi-core processors. A multi-core processor may include two or more processing units on a single computing component. Examples of a multi-core processors include the AMD PHENOM IIX2, INTEL CORE i5 and INTEL CORE i7.

Main memory unit 122 may include one or more memory chips capable of storing data and allowing any storage location to be directly accessed by the microprocessor 121. Main memory unit 122 may be volatile and faster than storage 128 memory. Main memory units 122 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 122 or the storage 128 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 may be based on any of the above described memory chips, or any other available memory chips capable of operating as described herein. In the embodiment shown in FIG. 1C, the processor 121 communicates with main memory 122 via a system bus 150 (described in more detail below). FIG. 1D depicts an embodiment of a computing device 100 in which the processor communicates directly with main memory 122 via a memory port 103. For example, in FIG. 1D the main memory 122 may be DRDRAM.

FIG. 1D depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1D, the processor 121 communicates with various I/O devices 130 via a local system bus 150. Various buses may be used to connect the central processing unit 121 to any of the I/O devices 130, including a PCI bus, a PCI-X bus, or a PCI-Express bus, or a NuBus. For embodiments in which the I/O device is a video display 124, the processor 121 may use an Advanced Graphics Port (AGP) to communicate with the display 124 or the I/O controller 123 for the display 124. FIG. 1D depicts an embodiment of a computer 100 in which the main processor 121 communicates directly with I/O device 130b or other processors 121' via HYPERTRANSPORT, RAPIDIO, or INFINIBAND communications technology. FIG. 1D also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 130a-130n may include a combination of multiple input or output devices, including, e.g., Microsoft KINECT, Nintendo Wiimote for the WII, Nintendo WII U GAMEPAD, or Apple IPHONE. Some devices 130a-130n allow gesture recognition inputs through combining some of the inputs and outputs. Some devices 130a-130n provides for facial recognition which may be utilized as an input for different purposes including authentication and other commands. Some devices 130a-130n provides for voice recognition and inputs, including, e.g., Microsoft KINECT, SIRI for IPHONE by Apple, Google Now or Google Voice Search.

Additional devices 130a-130n have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, may have larger surfaces, such as on a table-top or on a wall, and may also interact with other electronic devices. Some I/O devices 130a-130n, display devices 124a-124n or group of devices may be augment reality devices. The I/O devices may be controlled by an I/O controller 123 as shown in FIG. 1C. The I/O controller may control one or more I/O devices, such as, e.g., a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices. In further embodiments, an I/O device 130 may be a bridge between the system bus 150 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 124a-124n may be connected to I/O controller 123. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopy. Display devices 124a-124n may also be a head-mounted display (HMD). In some embodiments, display devices 124a-124n or the corresponding I/O controllers 123 may be controlled through or have hardware support for OPENGL or DIRECTX API or other graphics libraries.

In some embodiments, the computing device 100 may include or connect to multiple display devices 124a-124n, which each may be of the same or different type and/or form. As such, any of the I/O devices 130a-130n and/or the I/O controller 123 may include any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may include multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices 100a or 100b connected to the computing device 100, via the network 104. In some embodiments software may be designed and constructed to use another computer's display device as a second display device 124a for the computing device 100. For example, in one embodiment, an Apple iPad may connect to a computing device 100 and use the display of the device 100 as an additional display screen that may be used as an extended desktop. One ordinarily skilled in the art will recognize and appreciate the various ways and embodiments that a computing device 100 may be configured to have multiple display devices 124a-124n.

Referring again to FIG. 1C, the computing device 100 may comprise a storage device 128 (e.g. one or more hard disk drives or redundant arrays of independent disks) for storing an operating system or other related software, and for storing application software programs such as any program related to the software for the delivery scheduler 198. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 128 may be non-volatile, mutable, or read-only. Some storage device 128 may be internal and connect to the computing device 100 via a bus 150. Some storage device 128 may be external and connect to the computing device 100 via an I/O device 130 that provides an external bus. Some storage device 128 may connect to the computing device 100 via the network interface 118 over a network 104, including, e.g., the Remote Disk for MACBOOK AIR by Apple. Some client devices 100 may not require a non-volatile storage device 128 and may be thin clients or zero clients 102. Some storage device 128 may also be used as an installation device 116, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 102. An application distribution platform may include a repository of applications on a server 106 or a cloud 108, which the clients 102a-102n may access over a network 104. An application distribution platform may include application developed and provided by various developers. A user of a client device 102 may select, purchase and/or download an application via the application distribution platform.

Furthermore, the computing device 100 may include a network interface 118 to interface to the network 104 through a variety of connections including, but not limited to, standard telephone lines LAN or WAN links (e.g., 802.1, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.1a/b/g/n/ac CDMA, GSM, WiMax and direct asynchronous connections). In one embodiment, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Florida. The network interface 118 may comprise a built-in network adapter, network interface card, PCMCIA network card, EXPRESSCARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1B and 1C may operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Washington; MAC OS and iOS, manufactured by Apple, Inc. of Cupertino, California; and Linux, a freely-available operating system, e.g. Linux Mint distribution ("distro") or Ubuntu, distributed by Canonical Ltd. Of London, United Kingdom; or Unix or other Unix-like derivative operating systems; and Android, designed by Google, of Mountain View, California, among others. Some operating systems, including, e.g., the CHROME OS by Google, may be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some embodiments, the computing device 100 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 100 is a gaming system. For example, the computer system 100 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Washington.

In some embodiments, the computing device 100 is a digital audio player such as the Apple IPOD, IPOD Touch, and IPOD NANO lines of devices, manufactured by Apple Computer of Cupertino, California Some digital audio players may have other functionality, including, e.g., a gaming system or any functionality made available by an application from a digital application distribution platform. For example, the IPOD Touch may access the Apple App Store. In some embodiments, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 100 is a tablet e.g. the IPAD line of devices by Apple; GALAXY TAB family of devices by Samsung; or KINDLE FIRE, by Amazon.com, Inc. of Seattle, Washington In other embodiments, the computing device 100 is an eBook reader, e.g. the KINDLE family of devices by Amazon.com, or NOOK family of devices by Barnes & Noble, Inc. of New York City, New York.

In some embodiments, the communications device 102 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc.; or a Motorola DROID family of smartphones. In yet another embodiment, the communications device 102 is a laptop or desktop computer equipped with a web browser and a microphone and speaker system, e.g. a telephony headset. In these embodiments, the communications devices 102 are web-enabled and can receive and initiate phone calls. In some embodiments, a laptop or desktop computer is also equipped with a webcam or other video capture device that enables video chat and video call.

In some embodiments, the status of one or more machines 102, 106 in the network 104 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. Message Selection and Transmission Based on Confidence Values and Cool Down Factors in a Networked Environment Users of personalized messaging systems can encounter message fatigue, thereby reducing the efficacy of a message on its intended recipient. Message fatigue can result in wasted computational resources and bandwidth as messages transmitted over a network to the user's client device are not acted upon at the client device. For applications involving desired user interactions and responses, personalized messaging can be a tool to achieve user engagement targets.

The present disclosure describes systems and methods for message selection and transmission based on confidence values and cool down factors. The personalized messaging system can send relevant messages to a user at relevant times. The personalized messaging system can increase user engagement and efficacy of an application. Appropriate content delivered at the right time, tailored for each user, can have a positive effect on a user's engagement with application. Personalized and relevant messages delivered in a timely manner to each user through an application can translate to real-world actions undertaken by the user to improve health, wellbeing, fitness and overall quality of life.

To address some of the challenges associated with message fatigue as well as other related challenges, the present disclosure relates to a message selection system that can invoke a plurality of message objects, which, when invoked, can generate a plurality of messages. The message selection system can generate a confidence value for each of the messages and use the confidence value associated with each message to select one or more messages to send to the application of the client device. The message selection system can adjust the confidence values associated with each of the selected messages based on a cool down factor. The message selection system can use the cool down factor to adjust the confidence values of each of the selected messages based on various factors including but not limited to an amount of time since the last message was received by a client device, the total number of messages a user of the client device elects to receive within a predetermined time period, and a length of time the user of the client device is awake or active. The message selection system can then, based on the adjusted confidence values of each of the selected messages, make a determination to send one or more of the selected messages based on the adjusted confidence values.

The message selection system can select messages based on a likelihood that the message is going to achieve a desired endpoint or target value while adjusting the likelihood based on a time since the last message was delivered to the client device so as to reduce the likelihood that a user will experience message fatigue. The message selection system can reduce the likelihood that a user will experience message fatigue by selectively transmitting or sending a message to the client device of the user based upon a likelihood that the message will have an intended effect. Because the number and frequency of messages that cause individual users to experience message fatigue can vary, the message selection system can incorporate information about each user's message preferences, application engagement, and responses to similar messages to build a framework or model for delivering personalized messages at appropriate times.

The messages sent by the message selection system to respective client devices of users can be opened via an application executing on the respective client devices. The application executing on the client device can display a message from the message selection system to a user of the client device, prompting the user to perform an action or to elicit a user response. The application can be configured to provide information back to the message selection system including data corresponding to when messages were received at the client device, when the application displayed the message, activity performed on the application by the user, activity performed by the user on the client device, among others. The message selection system can use the information collected or received from the client device of the user to evaluate the effectiveness of the message in getting the user to perform an action or the content and timing of the user response to improve the personalization of the messages sent to individual users or in some embodiments, to monitor the user and their behavior to the messages.

In certain embodiments, the message selection system can maintain user profiles for a plurality of users. For each user profile, the message selection system can execute an invocator which can invoke message objects at predetermined time intervals. Each message object can generate a candidate message using a message template that is a candidate for transmission to the client device associated with the user profile. A message object evaluator of the message selection system can incorporate contextual data into a model of the message object to output a confidence value associated with the candidate message generated by the message object. The confidence value can be indicative of the likelihood that a candidate message sent to a user will have an intended effect. The message object evaluator can output a confidence value for message objects that satisfy certain constraints. The message object evaluator can evaluate the confidence values associated with each of the candidate messages based on certain conditions, update the confidence value based on a cool down factor and determine to send the candidate message to the client device if the updated confidence value crosses a predetermined threshold.

The message selection system can receive response data from a reporting agent of the application executing on the client device associated with the user profile. A response evaluator of the message selection system can incorporate the response data into the models of the message objects so as to improve the performance of the models based on response data corresponding to previous messages sent to the client device. The response data can be compared against target values (or desired endpoints) of the message objects to improve the models of the message objects. In this way, the message selection system can learn from a user's message preferences and responses and improve the selection process of future candidate messages as well as improve the quality of the confidence values computed for the future candidate messages. By doing so, the message selection system can select and send fewer messages to the client device of the user while at the same time increasing the likelihood that the user will engage or respond to the message and achieve the desired endpoint of the message.

According to at least one aspect of the disclosure, a method can include identifying, by one or more processors, a plurality of users and a plurality of message objects. The method can include retrieving, by one or more processors, contextual data for each of the plurality of users for one or more message objects. The method can include generating, by one or more processors, candidate messages based on the one or more message objects and contextual data. The method can include updating, by one or more processors, the confidence value for each of the candidate messages based on a cool down factor to generate an updated confidence value. The method can include selecting, by one or more processors, a candidate message based on the updated confidence value. The method can include transmitting, by one or more processors, the selected candidate message based on the updated confidence value crossing a predetermined threshold.

Figure 2:
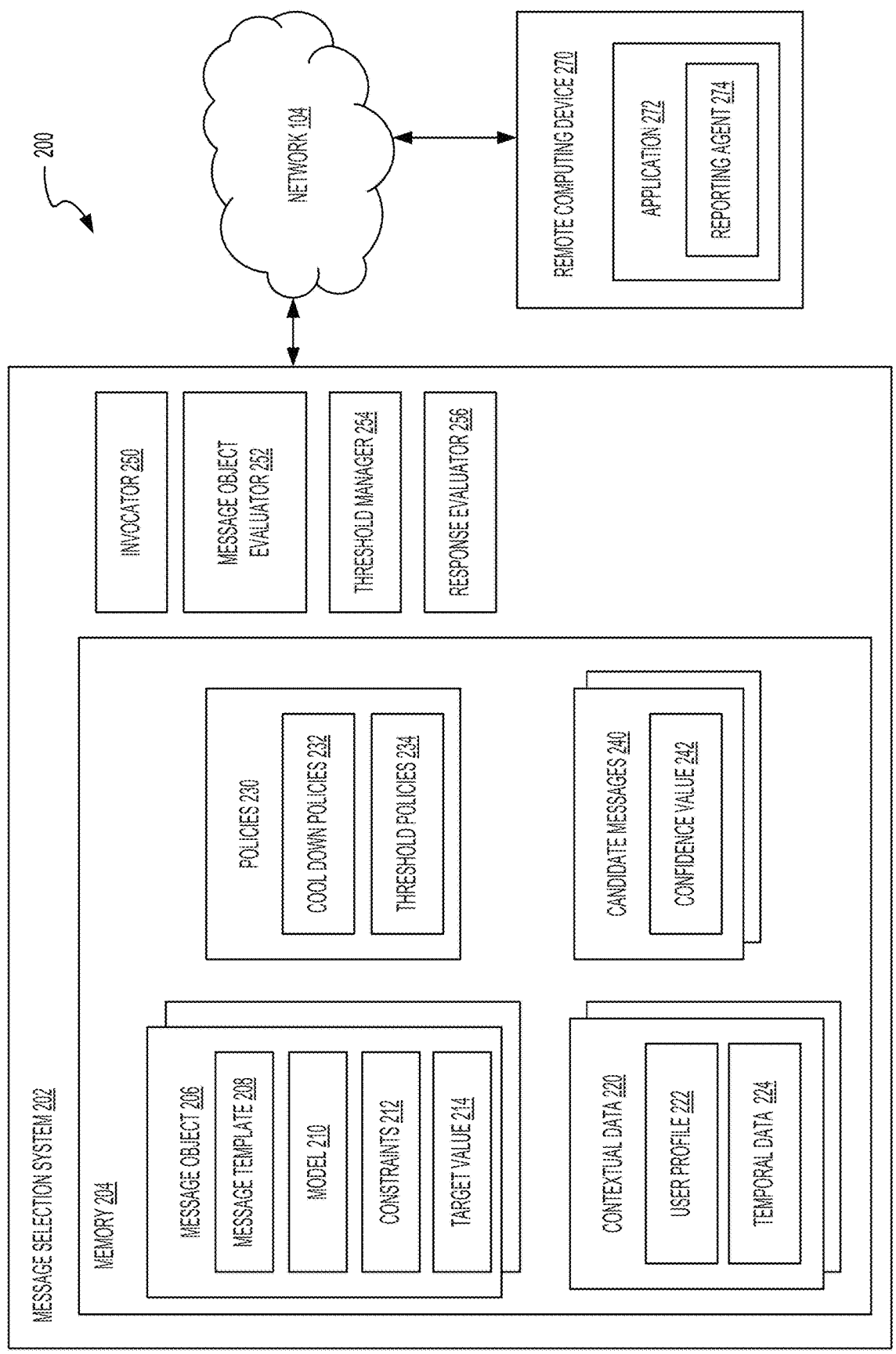
FIG. 2 illustrates a block diagram depicting an embodiment of system for sending relevant messages to a user.

FIG. 2 illustrates a block diagram of an environment 200 for competitive message selection. The environment 200 includes a message selection system 202 and at least one remote computing device 270. The message selection system 202 can select one or more messages to send to the remote computing device 270 via the network 104 and receive data from the remote computing device 270 including data corresponding to actions performed in response to the one or more messages that are sent to the remote computing device 270.

The environment 200 can include a plurality of remote computing devices 270. The plurality of remote computing devices 270 can belong to the same user or can belong to different users or entities of the message selection system 202. Each remote computing device can include an application 272 configured to communicate with the message selection system 202. The application 272 can include a reporting agent 274 configured to provide data corresponding to actions performed on the computing device in response to receiving messages from the message selection system 202. In some embodiments, the application 272 can be configured to display the messages generated and sent by the message selection system 202 as well as to provide data to the message selection system 202. Additional details regarding the application 272 and the reporting agent are provided below.

Referring now to the message selection system 202, the message selection system 202 includes memory 204. The memory 204 includes a plurality of message objects 206. Each of the plurality of message objects 206 can include message templates 208, models 210, constraints 212, and target values 214. The memory 204 also includes contextual data 220, which can include at least one user profile 222 and temporal data 224. The memory can also store candidate messages 240 as well as respective confidence values 242 for each of the candidate messages 240. As will be described herein, the message selection system 202 can generate the candidate messages 240 using the message objects and further calculate confidence values 242 for each of the candidate messages 240.

The message selection system 202 also includes an invocator 250, a message object evaluator 252, and a threshold manager 254 to evaluate each of the candidate messages 240. The invocator 250 can be an application, applet, script, service, daemon, routine, or other executable logic to select, identify and invoke a plurality of message objects 206. The invocator 250 can initiate an invoke process, which can be initiated by a cron job scheduled on a regular interval. A cron is a time-based job scheduler in Unix-like computer operating systems which can be used to schedule jobs (e.g., commands, or shell scripts). An invoke process can be based on a time (e.g. an invoke process can occur at 8 am on Monday, an invoke process can occur every 30 minutes, or an invoke process can occur every other Thursday). An invoke process can be based on an event (e.g. an invoke process can occur upon the message selection system 202 receiving data from the remote computing device 270 as described below). The invocator 250 can initiate an invoke process for a specific group of users. For example, the invocator 250 can initiate an invoke process for a subset of users using a predetermined feature of an application 272. The invocator 250 can initiate a different invoke process for different users. For example, the invocator 250 can initiate a first invoke process at a first time for a first user and a second invoke process for a second user at a second time. The invocator 250 can be broken down into a number of asynchronous requests, such as getting active users, getting user data and writing an invocation record to a database.

An example of the invoke process can be illustrated in the following pseudocode:

```
users = getActiveUsers( )
for u in users:
    d = getData(u)
    ts = Date.now( )
    for n in messageObjects:
        db.write(u.id, ts, hash(d))
        aws.s3.store({key: hash(d), value: d})
        meta = {ts}
        enqueue(n, meta + d)
```

The invoke process as illustrated by the pseudocode above can occur at a regular time interval (e.g., every 30 minutes). The invoke process can include identifying contextual data 220 (described in detail herein) for each user (e.g., getData(u)) and identifying the current time (e.g., Date.now( ). The invoke process can include writing an invocation record to a database (e.g., db.write(u.id, ts, hash(d)) which can include a hash of the contextual data 220. An invocation record can include a user identification, time stamp and data for each user (e.g. application data and user attention data). Application data can include user actions in response to messages received in the application. User attention data can include receptiveness of a user throughout the day such as the frequency of a user to respond messages receive in the application. The invocation record can be stored in Amazon Simple Storage Service (AWS S3) as illustrated in the pseudocode above.

Identifying active users (e.g., users of an application, users who respond to messages) can include querying the application 272 to get active users with messaging enabled. Getting user data can include getting data for each user, which can include application data and user attention data. The data can be used to filter out message objects 206 that do not satisfy hard constraints. Writing an invocation record to a database can be performed to group future evaluations and to track message object 206 decision making history for future model training. For example, the time stamp of the invocation record, application data for a user, and user attention data can be used by the response evaluator 256 as inputs into message object models 210. A hash of the contextual data 220 can be stored in a remote object for storage, which can conserve space in the message object 206 database. Storing some data remotely can allow the message selection system 202 to avoid performance degradation as a result of scarce disk space. The message object evaluator 252 can offload read request traffic from message object 206 at evaluation time to a remote database (e.g., AWS S3). The message selection system 202 can store user data with a hash table. A hash table can store unique changes in contextual data 220, which can be space efficient. For example, storing duplicate data can be avoided. Storing data in a remote database can reduce the frequency of the invocator 250 having to copy data out of a live database. Instead, the invocator 250 can read directly from a remote database during offline training of models 210. The invoke architecture can include parallel user processing, which can include multiple processes for getting user data.

As described above, the environment 200 can include one or more remote computing devices 270. In further detail, the remote computing device 270 can receive messages from the message selection system 202. The remote computing devices 270 can be internet enabled remote devices. For example, the remote computing device 270 can be an internet of things ("IoT") device. The IoT device can include a remote monitoring device that include remote motion sensors, temperature sensors, soil condition sensors, or video cameras. In some implementations, the remote computing device 270 can be a mobile computing device (or components thereof) such as cell phones, smart phones, laptops, or tablet computers. The remote computing device 270 can have limited computational power. The remote computing device 270 can be awoken, pinged, messaged, or otherwise contacted at predetermined intervals to make measurements, perform activities, or provide responses to requests for information. In some implementations, the remote computing device 270 can receive requests at regular, predetermined intervals.

The remote computing device 270 can include the application 272 to enable the remote computing device 270 to communicate with the message selection system 202. For example, the application 272 can receive messages from the message selection system 202 and return responses to the messages to the response evaluator 256. The application 272 can receive messages when the remote computing device 270 receives a data packet from the message selection system 202 via the network 104. When the message selection system 202 sends a message to the application 272, the application 272 can launch on the remote computing device 270. The application 272 can send a notification to the remote computing device 270 to ping, wake, message, or otherwise contact a user of the remote computing device 270. The application 272 can launch and display the message from the message selection system 202. The application 272 can include a reporting agent 274. The application 272 can include a graphical user interface to engage a user of the remote computing device 270. In some embodiments, the application 272 can include a smoking cessation application or any other digital therapeutic application in which messages can be transmitted to a subject using the digital therapeutic application.

The reporting agent 274 of the application 272 can be an application, applet, script, service, daemon, routine, or other executable logic configured to monitor the activity within the application 272. The activity can include one or more user performed actions. For example, a user performed action can include a breathing exercise, meditation session, yoga session, walking session, jogging session, running session, communication with colleagues, a phone call session, communication with a medical advisor or any other action that can be detected, determined or inferred by the reporting agent 274. In some implementations, the reporting agent 274 can monitor a time at which an activity was initiated, a time at which the activity was completed, a time at which the activity was interrupted by another computer function occurring in another process of the computing device, or a time at which the activity was paused or stopped due to an interaction with the environment of the application 272. For example, the application 272 can use acceleration data from the remote computing device 270 to detect an initiation of a walking session and a completion of the walking session. The application 272 can relay or otherwise provide data to the reporting agent 274 that a user of the remote computing device 270 initiated a walking session and completed the walking session. The application 272 can correlate data on the remote computing device 270 to a user generated response. For example, the application 272 can display information requesting a response from a user. The application 272 can display a message asking the user to make a selection on the application 272 to confirm the user completed an activity. The application 272 can display a message asking the user to make a selection on the application 272 to confirm the user did not complete an activity. The application 272 can display a message requesting user feedback related to the appropriateness of the message. For example, the user can make a selection on the application 272 that notifies the reporting agent 274 that messages sent during events scheduled on the user's calendar are not appropriate. The user can make a selection on the application 272 that notifies the reporting agent 274 that messages sent after meetings scheduled on the user's calendar are appropriate.

The remote computing device 270 can assign a timestamp to the activity. The reporting agent 274 can access data related to the activity and the timestamp associated with the activity. The reporting agent 274 can detect that a user is performing an activity by accessing data on the remote computing device 270. The reporting agent 274 can receive a report from application 272 detailing the user performed activities. In some implementations, the reporting agent 274 can generate one or more messages to send reporting data to the message selection system 202.

Referring again to the message objects 206, the message objects 206 can be data structures that can be a framework for optimization around a message. The message object's data structure can include a message template 208, a model 210, constraints 212 and a target value 214. The invocator 250 can invoke a plurality of message object 206. A message object 206 can generate a candidate message 240 based off the message template 208 which is evaluated by the message object evaluator 252.

The message object 206 can include one or more message templates 208. A message template 208 can include a text string. The message object 206 can use contextual data 220 to populate field of the message template 208. The message object evaluator 252 can use the message template 208 to generate candidate messages 240. The message template 208 can be a static text, a template, or instructions for generating a message string. The template can include instructions to retrieve data from a data library stored in memory 204. The data from the data library can be substituted into the template before being sent to a user. For example, a template can include placeholders or variables that are filled in or substituted into the template before the message template 208 is set to a remote computing device 270. For example, the message can include images, videos, processor executable instructions that are transmitted to and executed by the remote computing device 270, or meta data. A message template 208 of a first message object 206 can be identical or different from a message template 208 of a second message object 206.

The model 210 of the message object 206 can receive contextual data 220 as inputs and output a confidence value 242 that indicates the predicted effectiveness of a message in achieving a target value 214. For example, contextual data 220 can be inputs to models 210 of respective model objects 206. Contextual data can include user specific data, date, time of day, day of week, weather related data, among others. The model 210 can receive inputs and output various outputs. For example, inputs can include temporal data 224 or user data and outputs can include a success rate or a confidence value 242 calculated based on the input data. For example, the model can correlate temporal data 224 specifying a timestamp of a user response to message effectiveness. The response evaluator 256 can update the model 210 based on historical data. For example, if the response evaluator receives data from the reporting agent 274 indicating that a user of the remote computing device 270 executing the application 272 is unresponsive to messages on the weekends, the response evaluator 256 can update the model 210 to reduce the probability of sending messages on weekends. The model 210 can undergo updates to learn from historical data. The response evaluator 256 can update the model 210 used to generate the message for which a response was generated based on temporal patterns for certain types of demographics based on user application data. For example, the response evaluator 256 can determine that user above a certain age tend to get dehydrated on a hot day. The response evaluator 256 can update the model 210 to send messages getting the user to stay hydrated.

The model 210 can be a machine learning model (e.g., reinforcement learning model, k-nearest neighbor model, backpropagation model, q-learning model, genetic algorithm model, neural networks, supervised learning model, or unsupervised learning model). The model 210 can include feature sets which are the available features for the machine learning model. The feature sets can include user application data, temporal context, effectiveness of similar messages, and user attention indicator which are described in a later part of this section. Retraining the model 210 with new data or time series can allow the message object 206 to improve the model 210 associated with the message object 206. The response evaluator 256 can add new features to the model 210 which may include updating the data service to return more user context information. The response evaluator 256 can fill in data points with new feature values at each historical timestamp which can include recalculating the historical user context, allowing for the response evaluator 256 retrain the model on all historical data with new added features.

It should be appreciated that the message selection system 202 can use feedback received from the remote computing devices 270 to which messages were sent to improve the message generation and selection capabilities of the message selection system 202. For instance, the message selection system 202 can be configured to update the models 210 of the message objects 206 used to generate candidate messages 240 based on historical data relating to the candidate messages 240 generated by the message objects 206. The successes or failures of message objects 206 in the past can improve the predictive capability of future models 210. A model 210 can use sent messages and their corresponding results and feature sets during the training phase of the model 210. A number of different supervised machine learning models can be trained online or offline. Training a model 210 can use a cross-validation approach to find optimal model parameters. Retraining message object models 210 can occur at each iteration (e.g., training cycle). Some models 210 (e.g., tree-based models, neural networks) can be trained on a rolling basis in which new data is received and the existing model can incorporate the new data without retraining using the entire data set. A message object 206 can include a model 210 that is predictive of the confidence values 242 of candidate messages 240.

The message object 206 can include a set of constraints 212. Constraints 212 can include limitations or restrictions that govern whether a candidate message 240 should be generated from the message object 206 or whether the generated candidate message 240 can be transmitted. A constraint 212 can include a predetermined time of day or a window of times to send a candidate message 240. A constraint 212 can include a determined time of day and day of the week defining a time window when a message template 208 can be sent. A constraint 212 can include a user type (e.g., gender, occupation, company, or affiliation). A constraint 212 can include a recurring day of the week to send a message. For example, the constraint 212 for a message object 206 can be a time-based window between 10 AM and 4 PM whereby the message object evaluator 252 can send a message. When the message object evaluator 252 processes the message object 206 with the above constraint, the message object evaluator 252 can determine, based on the current time, whether a candidate message 240 should be generated (or whether a candidate message 240 generated from the message object 206 can be transmitted). A message object 206 may only be able to send a message on a particular day of the week (e.g., only on Mondays or Fridays). A restriction can include days or times when the message object evaluator 252 bars a messages object 206 from sending a message, such as on weekends. A message object 206 may have a constraint 212 of being able to send a message on Mondays unless the Monday is a holiday, in which case, the message object 206 is restricted from sending the message. A constraint 212 can include information about holidays, leap years, time of the day, time of the week, time of the month, time of the year, or any other calendar related subjects. A constraint 212 can specify a particular time or a window of times when a message object evaluator 252 can send a message. A constraint 212 can include a minimum confidence value 242.

The message object 206 can include a target value 214. The target value 214 can correspond to an action (e.g., to get a user to perform a specific action in the application 272). The target value 214 can correspond to a reply or response. The target value 214 can include a numerical value corresponding to the effectiveness of a message received by a remote comping device 270. The target value 214 can correspond to an action in the application 272 and a desired accomplishment rate of the action. For example, a first action in the application 272 may be a breathing exercise and a second action in the application 272 may be a jogging exercise. The target value 214 corresponding to the first action may be 80% and the target value 214 corresponding to the second action may be 15%. For example, a message calling a user to perform a certain task in the application 272 can be assigned a numerical value corresponding to the number of times the user performed the task as a percentage of how many messages were sent to the user to perform the task within a certain time period. A message including subject matter that invites a user to perform a certain task in the application can be assigned a numerical value corresponding to how long after the message is sent to the user that the user performed the task. In another example, a message calling a user to reply can be measured by determining if the user replied to the message or if the user did not reply to the message. Target values 214 for rhetorical messages may not easily defined because a rhetorical message does not elicit a measurable user response.

A message's failure or ability to elicit a purported action can be used as an input to the message object model 210. A first message object 206 can have a target value 214 of getting a user to stay hydrated. The first message object 206 can have a message template 208 of "Hi [name], drink a cup of tea." A second message object 206 can have a target value 214 of getting a user to stay hydrated. The second message object 206 can have a message template 208 of "Hi [name], drink a glass of iced water." The message object evaluator 252 can use contextual data 220 related to the outside temperature and the tendency for the user to forget to stay hydrated to determine that the first message object 206 and second message object 206 should generate candidate messages 240. If the outside temperature is below 20° F., the first message object 206 may generate a first candidate message 240 with a high confidence value 242 compared to the second message object 206 which may generate a second candidate message 240 with a low confidence value 242. If the message object evaluator 252 recently sent a message related to hydration, the message object evaluator 252 may reduce the confidence score 242 of the first candidate message 240 and the confidence score 242 of the second candidate message 240. If the first candidate message 240 has an updated confidence score 242 passing a threshold value, the message object evaluator 252 can populate the message template 208 with data from the user profile 222 and send the candidate message 240 to the user of the remote computing device 270 executing the application 272.

Referring again to the message object evaluator 252, the message object evaluator 252 can generate candidate messages 240. The message object evaluator 252 can generate or assign a confidence value 242 for each of the candidate messages 240 generated from the message objects 206. The message object evaluator 252 can use the confidence values 242 associated with the candidate messages 240 to determine to refrain from sending any messages to a user of the remote computing device 270 or to send one or messages a user of the remote computing device 270. Candidate messages 240 can that have a confidence value 242 higher than a threshold. The candidate messages 240 can be the messages generated from the execution of the message objects 206 by the message object evaluator 252. The candidate messages 240 can include messages that have a confidence value 242 lower than a threshold. The message object evaluator 252 can generate the candidate messages 240 by passing contextual data 220 (and other data) message objects 206. The message objects 206 can output or otherwise generate candidate messages 240 if the data provided to the respective message object 206 satisfies the constraints 212 of the message object 206. The message object evaluator 252 can input contextual data 220 to the message object model 210 to generate a confidence value 242 for the candidate message 240. The message object evaluator 252 can update the confidence value 242 based on a cool down factor to generate an updated confidence value 242. Candidate messages 240 can be selected for transmission to a remote computing device 270 based on an updated confidence value 242. Candidate messages 240 can be generated by the message object evaluator 252.

Candidate messages 240 can include confidence values 242. The confidence values 242 can be normalized and include a number between 0 and 1 (inclusive) 242 indicating the likelihood for a message to have an intended effect on the user of a remote computing device 270. The confidence values 242 can include other ranges, such as between 0 and 100 (inclusive). Message relevance can include a combination of message content, user data, user attention and temporal context. Estimating the effectiveness of a particular message of a particular user at a particular point in time can include a supervised machine learning approach. The current time context (e.g., time of day, day of the week, or week of the year), user application data, and user attention can be used as features in a supervised machine learning model. The type of decision model (e.g., polynomial regression, decision tree, or paired comparison analysis) can vary from message object 206 to message object 206. The model 210 of each message object 206 can output a confidence value 242 indicating the confidence level of the target value 214. The message object evaluator 252 can update confidence values 242 when an invocator 250 initiates an invoke process.

It should be appreciated that the message selection system 202 can use contextual data 220 as inputs into the models 210 to generate confidence values. The contextual data can include a user profile 222 and temporal data 224. The contextual data 220 can include effectiveness of similar messages. For example, the message object 206 can use contextual data 220 as inputs to generate a confidence value 242. A message object 206 can use contextual data 220 to evaluate constraints 212. Similar messages can be a predictive indicator of the success or failure of a current message under scrutiny. Similar messages can be grouped by purpose or subject. The purpose of a message can include a call to action (to get a user to engage with an application 272 feature) or a call to reply (to get the user to respond to the message). The subject of message may, at a high level, be about a feature (e.g., mission), informational, health related, or money related. The contextual data 220 may be manually generated or generated through an unsupervised machine learning approach.

Contextual data 220 can include user profiles 222. A user profile 222 can include data associated with a specific user. A user profile 222 can include a digital representation of a user's identity, such as a user's name, location, historical data, habits, application usage, application interaction, and response rate. A user profile 222 can include data derived from application 272 use. The data may include user event data specific to the application 272 such as the number of times a user smokes a cigarette and a timestamp of the user's smoking of a cigarette. The data may be important for an application involving smoking cessation. The data may include finer grained user engagement data such as when the application 272 opens. In some implementations, the message selection system 202 can generate derived features from raw data, depending on the type of model 210 implemented. For example, derived features can include a list of timestamps of a user's smoking of a cigarette rather than the raw data of number of smoking events per day.

Contextual data 220 can include temporal data 224. Temporal data 224 can include the current time. Temporal data 224 can include temporal context. Temporal context can include usable information about the current time, such as time of day adjusted from time zone, day of the week, and season. Temporal data 224 can be generated by the reporting agent 274. The reporting agent 274 can assign a timestamp to a user action or response. The reporting agent 274 can send the temporal data 224 via the network 104 to the response evaluator 256. The reporting agent 274 can assign a timestamp when a message is received by the remote computing device 270. The reporting agent 274 can assign a timestamp when a message is received by a user of the remote computing device 270.

Contextual data 220 can include an indicator of user attention. User attention can include the receptiveness of a user throughout the day, which can be a factor in whether or not the message will have its intended effect. User attention can be highly specific. The message object evaluator 252 can identify various features of user attention to input into a model 210 for training message objects 206. The message object evaluator 252 can use an initial guess, a historical user time-of-day preference, and application engagement data as inputs into a model 210 for training message objects 206. An initial guess can include an initial hypothesis about user attention. Because there may be no historical data to work with when a user first signs up for the application 272, the message object evaluator 252 may make an initial hypothesis which is random or based on a human guess. The human guess can be based on data from other users. For example, users may mostly interact with the application 272 in the morning or at night on weekdays. The best human guess may be based on demographic data. For example, if there are distinct patterns, the response evaluator 256 can create clusters of users based on demographic data. The response evaluator 256 can use a time-of-day model as an initial hypothesis for user attention. The response evaluator 256 can chart user attention over the span of a day or over the span of a week. The response evaluator 256 can user historical user time-of-day preference as more messages 208 are sent to the user over time. As more messages are sent and results are received, a more accurate picture of when a user is likely to be receptive to a message can be constructed. The models 210 can weigh historical inputs based on the amount of historical inputs that exist in the database and the effect of success rate the predictive nature of the model 210. The response evaluator 256 can use a learning rate to control the speed at which the message selection system 202 learns a user's time-of-day preference. The response evaluator 256 can choose a learning rate to avoid overfitting the engagement pattern and to learn the user's preferences as quickly as possible. Using a high learning rate can lead to overfitting the engagement pattern, which can lead to capturing random noise. Using a low learning rate can lead to taking longer than necessary to learn a user's time-of-day preferences. Application engagement data can include general time of day engagement data generated by the application 272. The response evaluator 256 can use application 272 engagement data to predict of the effectiveness of a message, which may allow the application engagement data to be a proxy for user attention. Contextual data 220 can be generated by the reporting agent 274. The reporting agent 274 can receive feedback from the user.

Referring again to the message object evaluator 252, the message object evaluator 252 in further detail can be an application, applet, script, service, daemon, routine, or other executable logic to determine when to generate candidate messages and transmit one or more of the candidate messages 240. The message object evaluator 252 can pass contextual data 220 to the message objects 206 to generate candidate messages 240. The message object evaluator 252 can generate confidence values 242 for the candidate message 240. For example, the message object evaluator 252 can take a set of confidence values 242 and compare their confidence values 242 to one or more thresholds, which are described further below, to determine whether the candidate message 240 should be sent. The message object evaluator 252 can determine which, if any, of the candidate messages 240 should be sent to the user of the remote computing device 270 based on the confidence values of the candidate messages 240.

The message object evaluator 252 can select a candidate message 240 from a pool of candidate messages 240 generated by a particular invocation of a set of message objects 206 based on the confidence value 242 of the candidate message 240 satisfying a predetermined threshold. The candidate message 240 can be weighted by a confidence value 242. The message object evaluator 252 can adjust the confidence value 242 of the chosen candidate message 240 by multiplying the confidence value 242 by a cool down factor. The message object evaluator 252 can adjust the confidence value 242 of the chosen candidate message 240 by adjusting the confidence value 242 by a cool down factor. In some embodiments, the message object evaluator 252 can adjust the confidence value 242 of the chosen candidate message 240 by scaling the confidence value 242 by a cool down factor. The message object evaluator 252 can determine if the message object evaluator 252 should send the selected candidate message 240 based on a confidence value 242 crossing a threshold. For example, a confidence value 242 of 0.8 exceeds a threshold value of 0.7. The message object evaluator 252 can send a message if the message object 206 satisfies a constraint 212. The constraint 212 can be:

$$CV \times CDF > T, T \in [0,1], CV \in [0,1] \quad \text{(Equation 1)}$$

where CV is the confidence value, CDF is the cool down rate a T is the threshold and $$CDF = (\text{MIN}(LMI/CDI, 1))^{CDR}, CDR \in \mathbb{R}, CDI \in \mathbb{R}, \quad \text{(Equation 2)}$$

where LMI is the last message interval, CDI is the cool down interval, and CDF is the cool down rate.

Each message object 206 (or the candidate messages 240 generated thereby) can compete directly with each other for a particular user at regular time intervals. Competition between candidate messages 240 can include ranking the candidate messages 240 based on, for example, confidence values 242 indicating the likelihood for a message to have an intended effect on the user of a remote computing device 270. The message object evaluator 252 can rank the candidate messages 240 based on confidence values 242. The message object evaluator 252 can rank the candidate message 240 from highest to lowest confidence value 242. The message object evaluator 252 can select a candidate message 240 for transmission based on the rank of the candidate message 240. In some implementations, the message objects 206 can include confidence values 242 and the message objects 206 can be sorted or ranked by, for example, confidence value 242. The message object evaluator 252 can select one or more of the message objects 206 to generate candidate messages 240. In some implementations, the message object evaluator 252 ranks and sorts the message objects 206. The message object evaluator 252 can send the candidate message 240 when the message object evaluator 252 has completed evaluating the message objects 206. In some implementations, the generated candidate messages 240 can be ranked, sorted, and a selected portion of the candidate messages 240 can be transmitted to the client device or remote computing device 270.

Competition between message objects 206 can include sorting message objects 206, such as sorting message objects 206 based on confidence value 242 and selecting a subset of message objects 206 based on the category of the message object 206. For example, a category of the message object 206 can include fitness workouts, breathing exercise, de-stressing activities, hydration reminders, smoking cessation tips, among others. The message object evaluator 252 can select a subset of message objects 206 related to fitness workouts to select a candidate message 240 encouraging the user of the remote computing device 270 to perform a workout. The message object evaluator 252 can select the candidate message 240 with the highest confidence value 242 generated by the message objects 206. The candidate message 240 with the highest confidence value 242 can be selected by the message object evaluator 252 for transmission to the remote computing device 270 if the associated confidence value 242 crosses or satisfies a predetermined threshold.

The message object evaluator 252 can execute the evaluation process of the candidate messages 240. The evaluation process can include the process by which the message object evaluator 252 can make a decision to transmit or not transmit a candidate message 240. The message object evaluator 252 can generate candidate messages 240 by passing contextual data 220 to a message object 206 to evaluate constraints 212. For example, the message object 252 can take contextual data 220 related to a user's smoking habits and temporal data 224 related to the time of day. A message object 206 can generate a candidate message 240 to say "Hi Jim! Instead of grabbing a cigarette, try taking a walk." A constraint 212 of the message object 206 can be that the message is not appropriate during the typical sleeping hours of the user. The user profile 222 can show that the user typically is awake between the hours of 7 am and 11 pm and the temporal data can show that the current time is 1 pm. If the constraints 212 are met, the message object evaluator 252 can generate a candidate message 240, and record the confidence value 242 in a database of candidate messages 240. At regular intervals, the message object evaluator 252 can identify the message objects 206 that have yet to generate a candidate message 240 and generate candidate messages 240 for the message objects 206. The message object evaluator 240 can determine the confidence value 242 of candidate messages 240. The message object evaluator 252 can identify candidate messages 240, weigh or sort the candidate messages 240 by confidence value 242, scale the candidate messages 240 by a cool down factor, and then select a candidate message 240. The message object evaluator 252 can use the confidence values 242 and threshold policies 234 to determine whether or not a candidate message 240 should be sent. For example, if the confidence value 242 is above a threshold value according to a threshold policy 234, the message object evaluator 252 can determine to send the candidate message 240 to the remote computing device 270. If the confidence value 242 is below a threshold value according to a threshold policy 234, the message object evaluator 252 can determine not to send the candidate message 240 to the remote computing device 270. If the message object evaluator 252 makes a decision to send the candidate message 240, in some embodiments, the message object evaluator 252 passes the candidate message 240 to a messenger service of the message selection system 202 or communicatively coupled to the message selection system 202, which will facilitate transmission of the candidate message 240 to the user's device or remote computing device 270. The reporting agent 274 can record the action of the remote computing device 270 receiving the candidate message 240. If the message object evaluator 252 decides not to send the message, the message object evaluator 252 does not send the message.

Referring again to the response evaluator 256, the response evaluator 256 can analyze a response from a user of a remote computing device 270. The response evaluator 256 can record the results of messages that get sent out to a user, such as a success or a failure of a message object 206 to achieve message object target value 214. The response evaluator 256 can record the results of messages to obtain a target value 214 for the learning algorithm to optimize. Each message object 206 can define the success of the message object 206 in achieving the target value 214. Calculating results could be implemented as a batch process or a real time streaming process.

The response evaluator 256 can add new features to the model 210 which may include updating the data service to return more user context information. The response evaluator 256 can fill in data points with new feature values at each historical timestamp which can include recalculating the historical user context, allowing for the response evaluator 256 retrain the model on all historical data with new added features. The response evaluator 256 can create clusters of users based on demographic data. The response evaluator 256 can use a time-of-day model as an initial hypothesis for user attention. The response evaluator 256 can chart user attention over the span of a day or over the span of a week. The response evaluator 256 can user historical user time-of-day preference as more messages 208 are sent to the user over time. The response evaluator 256 can use a learning rate to control the speed at which the message selection system 202 learns a user's time-of-day preference. The response evaluator 256 can choose a learning rate to avoid overfitting the engagement pattern and to learn the user's preferences as quickly as possible. The response evaluator 256 can use application engagement data to predict of the effectiveness of a message, which may allow the application engagement data to be a proxy for user attention.

The response evaluator 256 can use the actions recorded by the reporting agent 274 to determine a cool down factor for future evaluations. A cool down factor can be unique to each individual user of an application 270. The cool down factor can reflect various factors including but not limited to an amount of time since the last message was received by the remote computing device 270, the total number of messages a user of the remote computing device 270 elects to receive within a predetermined time period, and a length of time the user of the remote computing device 270 is awake or active. The cool down factor can reduce the confidence value 242 of the candidate message 240 based on how recently a message was last sent to a user of the remote computing device 270. For example, at time $t=t_1$, the message object evaluator 252 can send a message prompting the user of the remote computing device 270 to engage in a fitness workout. At time $t=t_1+1$ hour, the message object evaluator 252 multiplies the confidence values 242 of the candidate messages 240 generated at $t=t_1+1$ hour by a cool down factor of ½, so the updated confidence values 242 are ½ of the confidence values 242 before the update. At time $t=t_1+4$ hours, the message object evaluator 252 multiples the confidence values 242 of the candidate messages 240 generated at $t=t_1+4$ hours by a cool down factor of ⅝, so the updated confidence values 242 are ⅝ of the confidences values 242 before the update, making it more likely that the message object evaluator 252 sends a message at time $t=t_1+4$ hours. The response evaluator 256 can update the cool down factor based on a user action performed in response to a message. For example, the response evaluator 256 can determine that a user is likely to experience message fatigue based on the current cool down factor so the response evaluator 256 can increase the cool down interval which can decrease the cool down factor. The cool down factor can be determined by one or more policies 230 described herein.

The message selection system 202 can store policies 230 to govern if and when to send a message based on confidence value 242 calculations. Policies 230 can include cool down policies 232 and threshold policies 234. Cool down policies 232 can include a cool down factor. A cool down factor can account for message fatigue by lowering the confidence value 242 of each candidate message 240 relative to how recently the last message was received by a remote computing device 270. For example, a linear cool down rate with a cool down interval equal to the user's waking hour period, w, which can be user reported or monitored through the application 272, divided by the maximum number of messages the user has elected to receive per day, r. The user can elect to receive a certain number of message or the message selection system 202 can determine a number of messages to send the user without causing message fatigue. If a user elected r=4 and w=14 hours, the cool down interval is 14/4=3.5 hours. If the cool down interval is an hour, cool down rate is linear, and the last message was received 10 minutes ago, the cool down factor is ⅙, which can reduce the overall confidence value 242. Cool down rate and cool down interval may be tunable parameters in the model 210. For example, the model 210 can be a linear model, an exponential model, or a decaying model. The type of model can be important for the message object evaluator 252 to construct a model 210 to predict the effectiveness of a message in eliciting a user response.

It should be appreciated that the target value 214 can be used by the response evaluator 256 to train the models 210. The target value 214 can represent whether or not the message had an intended effect, which can include a call to action (getting the user to use a feature in the application 272) or a call to reply (getting a user to reply to the message). The application data can be used to monitor the effects and record the results of the intended effect. Binary values can be used as target values 214. One goal of the message selection system 202 is to drive efficacy of messages objects 206 achieving their target values 214. A call to action and a call to reply can compete directly with each other. Intended effects can include successes in categories that are valued equally. Intended effects can include successes in categories that are weighed differently.

The message selection system 202 can include one or more threshold managers 254. A threshold manager 254 can be an application, applet, script, service, daemon, routine, or other executable logic to manage threshold policies 234. The threshold manager 254 can determine which threshold policy 234 to apply for a given user, given context (e.g., time of day), or message object 206. The threshold manager 254 can select from a variety of threshold policies 234, such as constant threshold, dynamic threshold, weighted random threshold, and fuzzy constant threshold. The threshold manager 254 can select or determine the cool down rate, cool down interval, last message interval, cool down factor, and distribution control factor.

Policies 230 can include threshold policies 234. A threshold manager 254 can control the quality of sent messages by, for example, selecting candidate messages 240 with a value greater than a threshold value. The quality of a message can be a quantitative indication of the usefulness to a user or a quantitative indication of the likelihood the user will act on the message. The threshold manager 254 can control the approximate number of messages sent to a remote computing device 270 receives per day. For example, given a desired number of messages per day, a threshold manager 254 can perform calculation based on a history of predicted confidence values 242. The threshold manager 254 can set a threshold such that the number of predictions above the threshold is equal to the number of messages desired to be delivered in a day. The threshold manager 254 can set a threshold by relaying the threshold to the message object evaluator 252. The message object evaluator 252 can obtain the threshold value or threshold values from stored memory 204. The number of messages delivered in a single day can be approximate because the threshold is based on a probability. The exact number of messages delivered may not be exactly the number of desired delivered messages. For example, the message selection system 202 may send a high-value message, even if sending the high-value message makes the messages sent larger than the number of desired delivered messages. The message selection system 202 may not send a low-value message, even if the message would have brought the number of messages sent to a desirable number of delivered messages. The message object evaluator 252 can determine if sending or refraining from sending a message, based on the threshold policy 234 would lead to message fatigue or positive user engagement with the application 272. The distribution of confidence values 242 can be obtained from mathematical simulation or mock run during an invoke process by the invocator 250. Number of messages per day for a particular user is a parameter that is input into the message object evaluator 252. The number of messages sent to a particular user per day can be a default number, such as 3, or it can be provided explicitly as a preference by a user, or by other models 210 that have learned an optimal number of messages per day given the user context.

Figure 4:
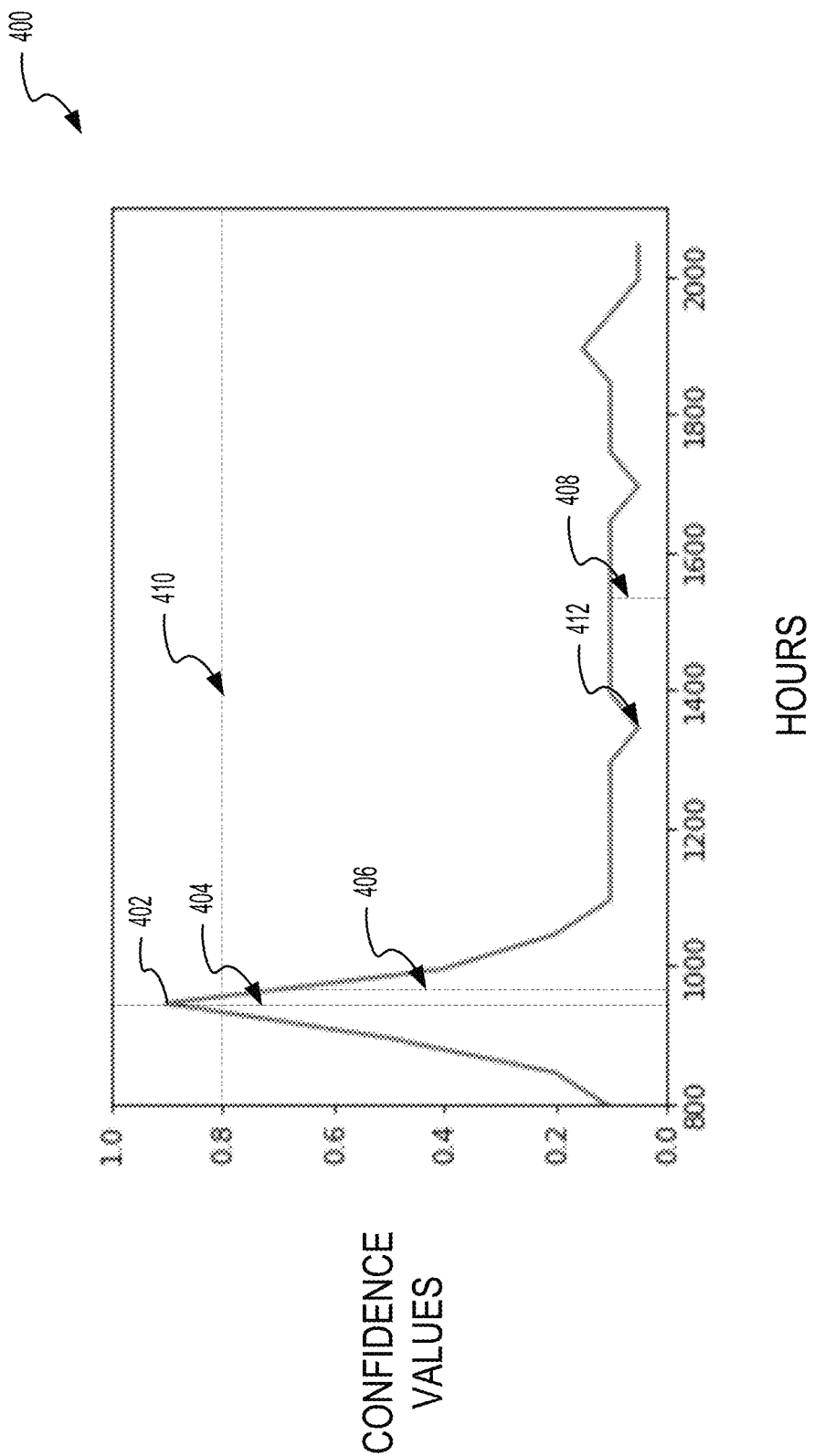
FIG. 4 illustrates a graph of confidence value versus hours with a steep peak.

A threshold policy 234 can include a constant threshold. A constant threshold can find the threshold in a given day where any value above the threshold indicates an optimal time to send a message. The threshold is calculated for a given day and does not change. The effect of an unchanging threshold is that the candidate messages 240 transmitted are optimized for effectiveness. A message object evaluator 252 may not frequently send messages if the threshold policy 234 is a constant threshold. FIG. 4 illustrates a graph 400 of confidence value versus hours with a steep peak. There is a steep peak 402 in the graph 400. A steep peak 402 can indicate that candidate messages 240 with a high confidence values 242 relative to the set of candidate messages are distributed towards one particular time of day. The message object evaluator 252 may not send the user specified number of messages or the number of messages determined by the message selection system 202 if messages with high confidence values 242 are clustered at time 404. The message object evaluator 252 can adjust the confidence values 242 based on a cool down factor, which may reduce the likelihood that messages are sent at time 406, even though messages at time 406 have a high confidence value relative to messages at time 408. If the threshold is set at a confidence value 242 of 0.8 depicted by line 410, the message object evaluator 252 will not send a message at time 406 which has a confidence value 242 of 0.7. Even though a message at time 406 has a high confidence value 242 relative to messages at time 408, a constant threshold may prevent the message object evaluator 252 from sending a message at time 406. A single peak 402 may show that a user has enough attention for a few (e.g., 2 or 3) messages per day and anything more than a few messages will contribute to message fatigue. However, the message object evaluator 252 may miss opportunities to send messages at time 406 with a high confidence value that are below a threshold line 410.

A threshold policy 234 can include a dynamic threshold. The threshold manager 254 may use a dynamic threshold if sending a minimum number of messages per day to the remote computing device is desired. The threshold manager 254 can recalculate the threshold based on the current time of day. A dynamic threshold can include finding the next future peak or set of peaks and solves the problem of missing the firing window if confidence values are skewed toward the beginning of the day. With a dynamic threshold, it can be guaranteed that there is at least one time in the future that message object evaluator 252 can transmit a message, which means that a user can receive the desired number of messages per day. A dynamic threshold may cause the threshold manager 254 to wait until the end of the day to transmit messages and may run out of time due to transmit messages based on the cool down rate. The dynamic threshold can achieve control over number of messages the message selection system 202 sends per day, but the threshold manager 254 may choose suboptimal times to send and may not make decisions regarding number of messages to send per day. For example, the threshold manager 254 can recalculate the threshold line 410 for different times of the day. The threshold line 410 can be at 0.8 between 0800 hours and 1000 hours, 0.9 between 1001 hours and 1800 hours and 0.7 between 1801 hours and 2100 hours. The threshold can be the highest during the working hours of a user's day and lower during the mornings and the evenings. The dynamic threshold policy can be useful in situations where a user is less receptive to messages during working hours and more receptive to messages at the beginning and end of the day.

A threshold policy 234 can include a weighted random threshold. A weighted random threshold can include a probability of sending a message relative to the candidate message confidence value 242. A message object evaluator 252 can scale the probability weight relative to the confidence value 242, with the parameters to that algorithm being derived from data such that the weighted random threshold sends approximately the desired number of message per day (through empirical distribution). The probability based threshold means that messages are allowed to be sent with a higher probability at confidence peak 402 and with lower probability at confidence valley 412. The advantage of a weighted random threshold is that there is still a chance for the message object evaluator 252 to transmit messages even at non-peak hours of the day which can introduce more randomness to the decision made by the message object evaluator 252. Involving more randomness can mean it is harder to control the number of messages sent per day. Changing the rate at which the invocator 250 invokes message objects 206 and the message object evaluator 252 evaluates message objects 206 changes the number of messages sent to the user per day if the probability weights are held constant. The message selection system 202 can recalculate the probability weight parameter and apply the recalculated probability weight parameter every time the message selection system 202 changes the invocation time interval to maintain the same number of messages sent per day.

Figure 5:
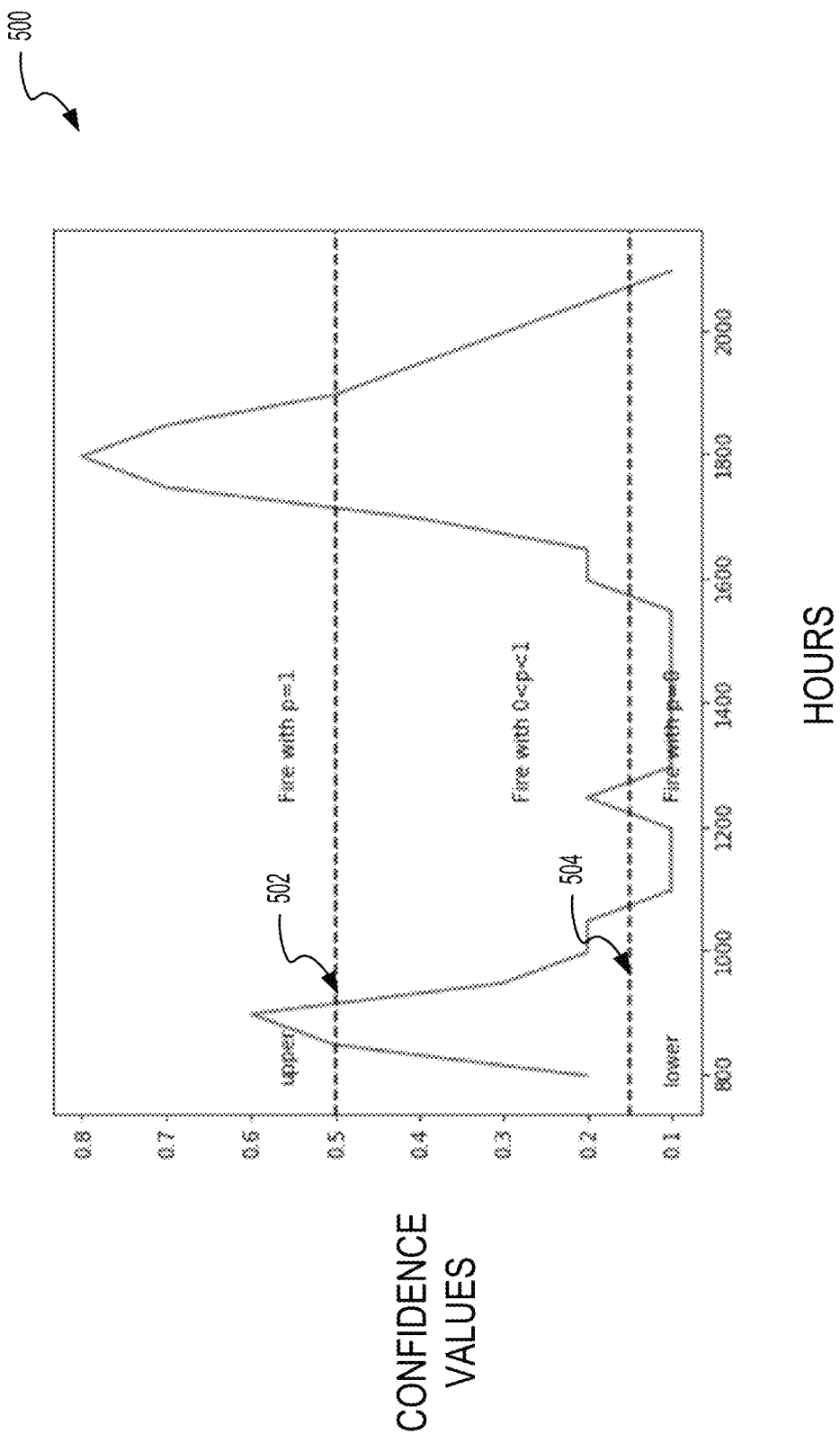
FIG. 5 illustrates a graph of confidence value versus hours with an upper threshold and a lower threshold.

A threshold policy 234 can include a fuzzy constant threshold. FIG. 5 illustrates a graph of confidence value versus hours with an upper threshold and a lower threshold. A fuzzy constant threshold can include values below the upper threshold 502 selected with some probability relative to the value in question. A lower threshold 504 may be chosen to set probability of sending a message to zero if the confidence value 242 is too low. For example, a threshold value of 0.5 can be set to send messages with probability of 1, a threshold value of 0.15 can be set to send messages with probability less than 1 and greater than 0 and a threshold value of 0.1 can be set to send messages with probability of 0. A fuzzy constant threshold can be similar to a constant threshold without a hard threshold where confidence values 242 above which the message object evaluator 252 sends messages and below which the message object evaluator 252 refrains from sending messages.

A distribution control factor can be used to control how quickly the probability of sending a message drops relative to the distance below the threshold. The distribution control factor is a mechanism to control the distribution of number of messages per day. The greater the distribution control factor, the greater the probability that the message object evaluator 252 will send the desired number of messages per day. A fuzzy constant threshold can include the following algorithm:

$$T=(CV^{DCF}) \times CV, CV \in [0,1] \quad \text{(Equation 3)}$$

where CV is the confidence value, DCF is the distribution control factor, and T is the threshold.

A fuzzy constant threshold can have the effect of the message object evaluator 252 sending candidate messages 240 with a lower confidence value 242 below the upper threshold 502, but refraining from sending messages with a confidence value 242 below a lower threshold 504. There is a chance to send messages at non-peak times of the day, introducing some randomness into the message sending decision. A message object evaluator 252 may send a candidate message 240 with a confidence value 242 that does not exceed a threshold to the remote computing device 270. Sending a message that is below a threshold may be advantageous in capturing user attention in a situation that has not been predicted by the model 210. Changing the rate at which message objects 206 are invoked and evaluated can change the number of messages sent to the user per day if the distribution control factor is held constant. The message selection system 202 may recalculate the distribution control factor parameter may be recalculated and apply the distribution control factor every time the invocator 250 changes the invocation time interval to maintain the same number of messages sent per day.

FIGS. 6A-6B illustrate distribution of numbers of messages sent per day. FIG. 6A depicts a distribution of messages sent on a particular day mean three and low variance corresponding to a large number of messages sent around hour three of a particular day. FIG. 6B depicts a distribution of messages sent on a particular day with higher variance than the distribution of FIG. 6A. The threshold manager 254 can apply a distribution control factor to the distribution of FIG. 6B to produce the distribution of FIG. 6C, which has a distribution control factor of 2. In applying a distribution control factor to the distribution, the threshold manager 254 can decrease the variance of the number of messages sent distribution.

An edge case in which the values around the threshold are highly repetitive can arise. For example, a hypothetical list of confidence values 242 can include the following: [0.95, 0.95, 0.95, 0.96, 0.96, 0.96, 0.96, 0.96, 0.96, 0.97]. If the threshold were drawn between the $6^{th}$ and $7^{th}$ elements of the list of confidence values 242 (calculated based on number of messages/day=3), there may be a higher chance of sending more than the desired messages per day, which can occur because there are many confidence values 242 of 0.96 both above and below the threshold. A naïve calculation that simply looks for a value at or above the threshold value may end up sending more messages 208. Message object 206 calculations can be highly repetitive. For example, if there are twenty-four invocations evenly distributed throughout a day, but a user only uses the application 272 at the beginning and end of the day, message object 206 evaluations during periods of non-use end up calculating confidence values 242 based on the same data, producing the same confidence values 242. The message selection system 202 can restrict the number of messages sent to a user, even if the confidence value 242 for the candidate message 240 is greater than a threshold because the message selection system 202 has data indicative of repeating confidence values 242.

Figure 3:
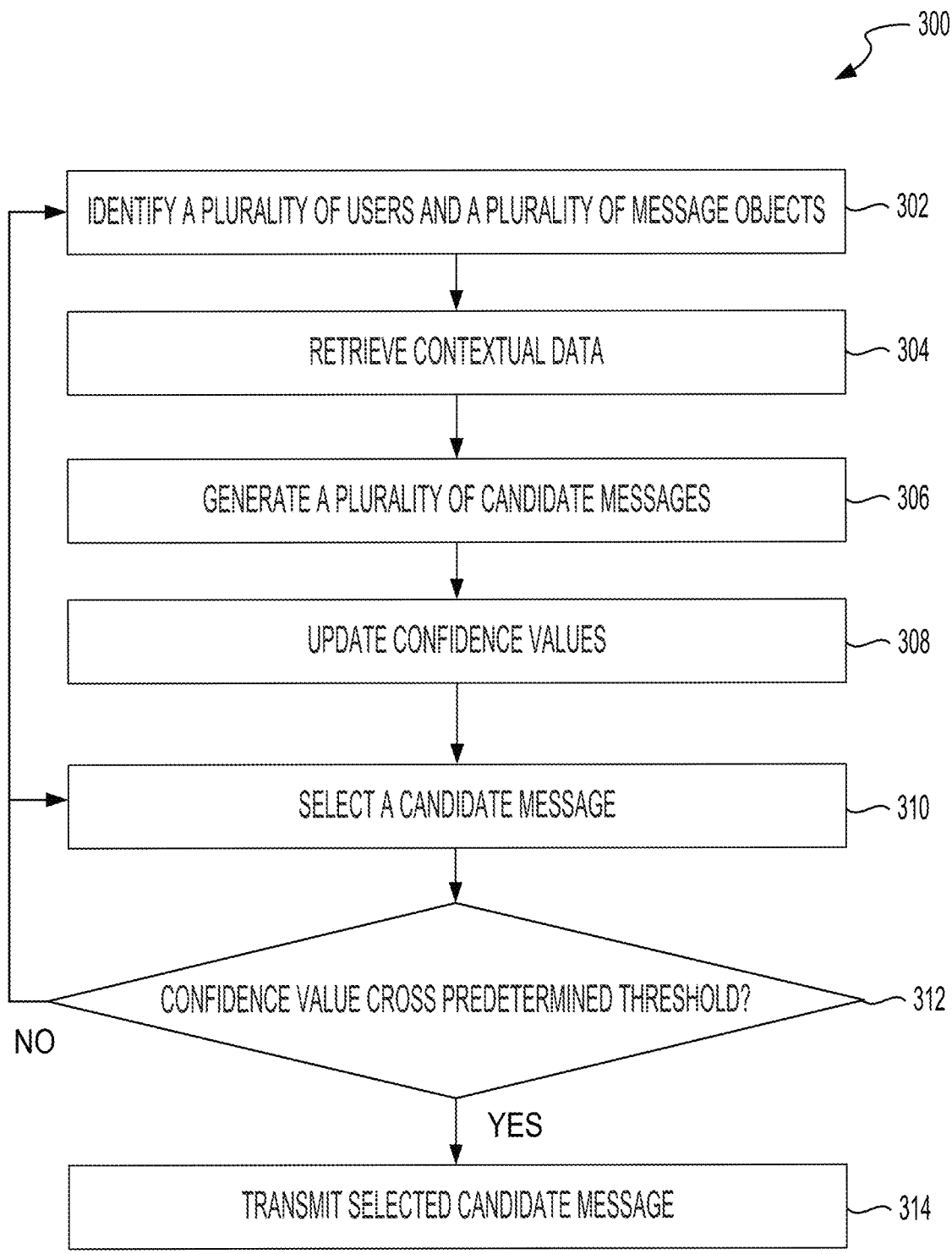
FIG. 3 illustrates a flow diagram of an example method for competitive message selection.

FIG. 3 illustrates a flow diagram of an example method 300 for competitive message selection. The method 300 can include identifying, by one or more processors, a plurality of users and a plurality of message object (BLOCK 302). The method 300 can include retrieving, by one or more processors, contextual data for each of the plurality of users for one or more message objects (BLOCK 304). The method 300 can include generating, by one or more processors, candidate messages based on the one or more message objects and contextual data (BLOCK 306). The method 300 can include updating, by one or more processors, the confidence value for each of the candidate messages based on a cool down factor to generate an updated confidence value (BLOCK 308). The method 300 can include selecting, by one or more processors, a candidate message based on the updated confidence value (BLOCK 310). The method 300 can include determining if the confidence value crosses a predetermined threshold (BLOCK 312). The method 300 can include transmitting, by one or more processors, the selected candidate message (BLOCK 314).

As set forth above, the method 300 can include identifying a plurality of users and a plurality of message object (BLOCK 302). Identifying a plurality of users can include accessing a database to determine active accounts. Also, referring to FIG. 2, among others, the reporting agent 274 can send a report to the response evaluator 256 which can analyze the response from the remote computing device 270. Identifying a plurality of users can include accessing the user profiles 222 of a plurality of users. Identifying a plurality of message objects can include identifying a plurality of message objects 206 stored in the message selection system 202. Identifying a plurality of message objects 206 can include accessing a plurality of message objects 206 stored in the message selection system 202. The invocator 250 can query the application 272 to get the active users with messaging enabled.

The method 300 can include retrieving contextual data for each of the plurality of users for one or more message objects (BLOCK 304). Retrieving contextual data can include retrieving contextual data 220 comprising a user profile 222 or temporal data 224. The message object evaluator 252 can retrieve contextual data and determine if and when to send a message to a user. Retrieving contextual data can include retrieving contextual data for each of the plurality of users identified in BLOCK 302. Retrieving contextual data can include accessing the contextual data 220 of user profiles 222 for each of the plurality of users identified in BLOCK 302. For example, for an identified user, the message object evaluator 252 can gather the contextual data 220 of the user by accessing the user profile 222 of the identified user. The invocator 250 can get data for each user, including application data and an indicator of user attention. The data can be used to filter out message objects 206 that do not satisfy constraints 212.

The method 300 can include generating candidate messages based on the one or more message objects and contextual data (BLOCK 306). The message object evaluator 252 can generate candidate messages. The candidate messages 240 can be based on the one or more message objects 206 and contextual data 220. For example, a first candidate message 240 can be generated by a first message object 206 for an identified user. A second candidate message 240 can be generated by a second message object 206 for the identified user. A third candidate message 240 can be generated by a third message object 206 for the identified user. The first candidate message 240 can be generated based on the user profile 222 of the user and a time-of-day preference of the user. The second candidate message 240 can be generated based on the user profile 222 of the user and the effectiveness of similar messages. The third candidate message 240 can be generated based on the temporal context of the message and the user application data. A message object 206 can generate a message can be transmitted to the remote computing device and is stored as a candidate message 240. The candidate message 240 can be generated and be associated with a confidence value 242. The confidence value 242 associated with the candidate message 240 can indicate how confident the message object 206 is in achieving the message object target value 214. A message object 206 can generate a first or original confidence value 242 associated with the message. A message object 206 can generate a candidate message 240 based on constraints 212. A message object 206 can fail to generate a candidate message 240 because the message object 206 did not fulfill the constraints 212.

The method 300 can include updating the confidence value for each of the candidate messages based on a cool down factor (BLOCK 308). The threshold manager 254 can update the confidence value 242 for each of the candidate messages 240 based on a cool down factor can include generating an updated confidence value 242. Updating the confidence value 242 can include accessing the cool down policies 232 of the message selection system 202 and applying a cool down policy to generate an updated confidence value 242 for the candidate message 240. Generating updated confidence values 242 based on a cool down factor can be applied to a first confidence value or an original confidence value. The updated confidence value 242 can be stored separately from the first confidence value 242 generated by the message object 206. For example, in a scenario where different cool down policies may be applied at different times, the original confidence value or first confidence value may be stored alongside any updated confidence values. The cool down factor can be a scaling factor that updates the confidence value 242 for each of the candidate messages 240.

The method 300 can include selecting a candidate message based on the updated confidence value (BLOCK 310). The message object evaluator 252 may select the candidate message 240 and the selected candidate message 240 can be transmitted to the remote computing device. The selected candidate message 240 may have the highest confidence value 242 of the set of candidate messages 240 that can be sent to a user. The candidate message 240 may not have the highest confidence value 242 of the set of candidate messages 240 that can be sent to a user. For example, a first candidate message 240 can have a lower confidence value 242 than a second candidate message 240 but the first candidate message 240 is sent to the user because of a threshold policy 234 The message object evaluator 252 determines when to execute the message object 206 to generate the candidate messages 240 and when to send the selected candidate message 240. The message object 206 can determine not to transmit the message of the message object 206 even if the candidate message 240 has a confidence value with the largest value of the pool of candidate message 240.

The method 300 can include determining if the confidence value crosses a predetermined threshold (BLOCK 312). If the confidence value 242 does cross or satisfy a predetermined threshold, the message object evaluator 252 can transmit the selected candidate message. If the confidence value does not cross or satisfy a predetermined threshold, the system can identify a plurality of message objects 206 or select a new candidate message 240.

The method 300 can include transmitting the selected candidate message to the remote computing device 270 (BLOCK 314). The message object evaluator 252 can compare the updated confidence value 242 with the threshold and decides whether to transmit the selected candidate message 240. The threshold can be based on various threshold policies 234 discussed in a previous part of the section.

After the message is transmitted, the remote computing device 270 can receive the message. The remote computing device 270 can display the message in the application 272. The user can receive the message, which can evoke a response or reply from the user. The user can receive the message, which can elicit and action from the user.

C. Indirect Updates to Messaging Systems

A messaging system can deliver messages to improve health, wellbeing, fitness and overall quality of life. However, the messaging system can be at risk of delivering an oversupply of messages to the user which can lead to message fatigue. To prevent message fatigue, the messaging system can use responses to messages to update models for selecting when to transmit the message, thereby customizing the time future messages are sent and the content of the messages. The messages sent by the messaging system can include non-rhetorical messages and rhetorical messages. Non-rhetorical messages can prompt a user of an application for a response or other input. Rhetorical messages do not prompt the user of the application for a response or other input. For example, the rhetorical messages can provide the user with information or data. Without user response data pertaining to the efficacy of the rhetorical messages, the messaging system may not be able to update the models for selecting when to transmit the rhetorical messages.

The present disclosure describes system and methods for indirect updates to models of messages objects of a messaging system. The messaging system uses responses to non-rhetorical messages to update models of message objects associated with non-rhetorical messages since the messaging system may not receive responses to rhetorical messages. The effectiveness or ineffectiveness of the rhetorical message cannot be based on a response to the rhetorical message because rhetorical messages implicitly do not generate a response from the user. Additionally, without a response from the user, the messaging system may not be able to quantify the benefit that rhetorical messages have on the user.

To address some of the challenges associated with a lack of response data from rhetorical messages, the present disclosure relates to indirect updates to models of messages objects of a message selection system. The message selection system can include a response evaluator that can incorporate the response data associated with non-rhetorical messages for updating the models of message objects associated with rhetorical messages. In this way, the message selection system can use the response data of non-rhetorical messages as a proxy for the response data (or lack thereof) of rhetorical messages. By doing so, the message selection system can select and transmit customized rhetorical messages to the client device of the user, even though the message selection system does not receive direct feedback regarding the rhetorical messages. The message selection system can also transmit rhetorical messages to the client device of the user at a customized time to prevent message fatigue.

Figure 7:
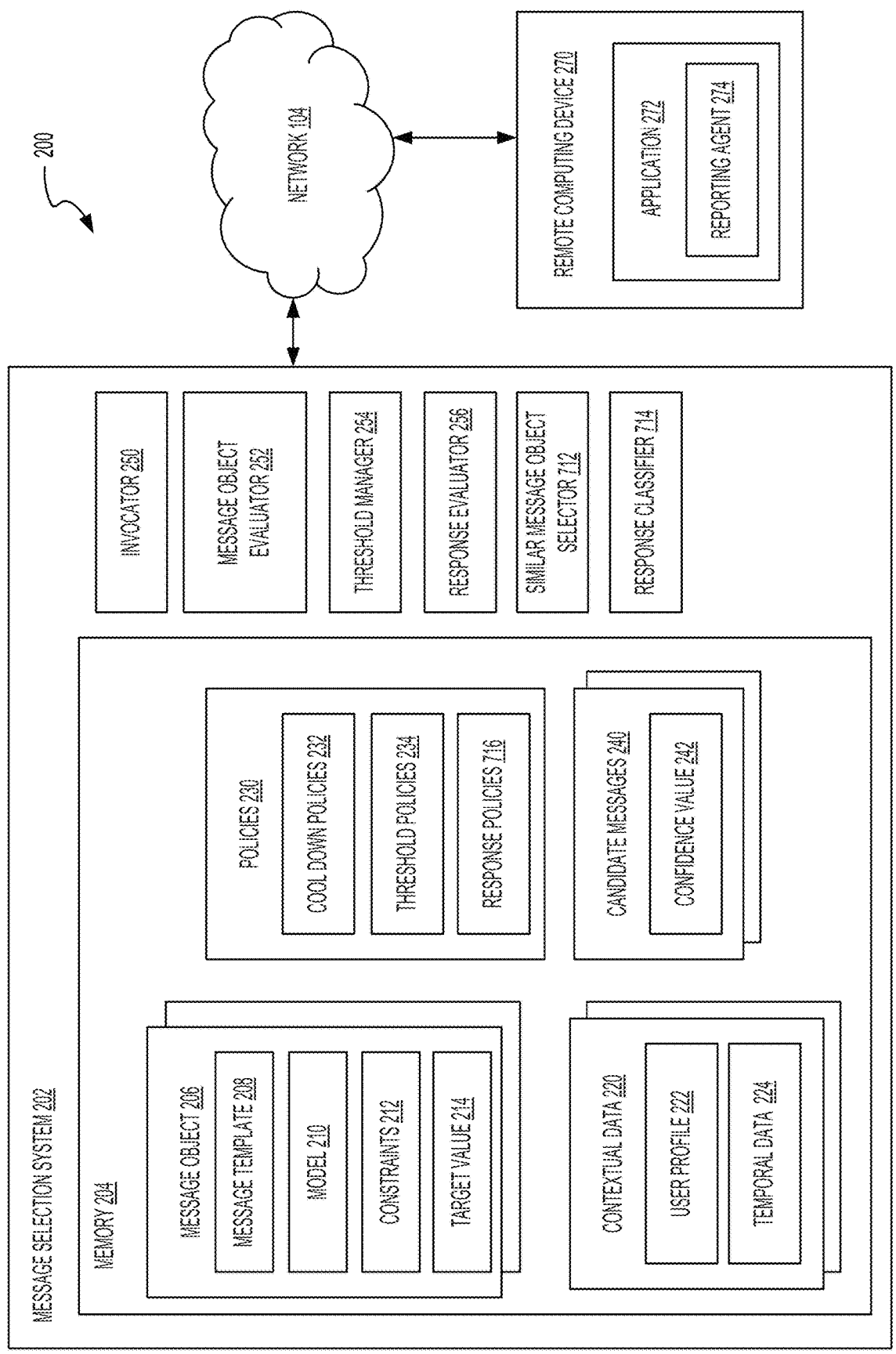
FIG. 7 illustrates a block diagram depicting an embodiment of system for sending relevant messages to a user.

FIG. 7 illustrates a block diagram of an environment 200 of a system to send messages to a user. The environment 200 includes a plurality of modules, components, or other entities that execute within the message selection system 202. The components of the message selection system 202 can include applications, programs, libraries, scripts, services, processes, tasks and/or any type and form of executable instructions executing on a device, such as a mobile device, computer, or server. The message selection system 202 can include any of the components of the other message selection system 202 described herein, such as described in relation to FIG. 2. In addition to the components described in relation to the message selection system 202 described in relation to FIG. 2, the message selection system 202 can include a similar message object selector 712 and a response classifier 714.

The message selection system 202 can include a plurality of message objects 206. The message object 206 can be non-rhetorical message objects 206 or rhetorical message objects 206. A non-rhetorical message object 206 can have a message template 208 from which a non-rhetorical message is generated. A non-rhetorical message is a message which elicits a user response when the message is received by the user of the remote computing device 270. For example, the non-rhetorical message can include processor executable instructions that when executed by the remote computing device 270 cause the remote computing device 270 to display a, for example, prompt or input to the user. Activation of the prompt or input can generate response message that the remote computing device 270 transmits to the message selection system 202. The non-rhetorical message object 206 has a non-rhetorical message model 210. The model 210 can be updated based on the responses from the remote computing device 270 generated in response to the non-rhetorical messages. The non-rhetorical message object 206 has a target value 214 that corresponds to a reply or response from the user of the remote computing device 270. The target value 214 may correspond to an action.

The message objects 206 can also include rhetorical message objects. A rhetorical message object 206 can have a message template 208 from which a rhetorical message is generated. A rhetorical message can be a message which does not elicit a user response when the message is received by the user of the remote computing device 270. For example, the rhetorical message can encourage the user to drink more water without prompting the user to record the user's water intake or without asking the user to confirm that the user increased water intake. In another example, the rhetorical message can display information or data to the user when rendered by the application 272 at the remote computing device 270. The rhetorical message object 206 has a rhetorical message model 210. The rhetorical message object 206 has a target value 214 that may correspond to an action. The message selection system 202 can determine a target value 214 associated with a rhetorical message object 206 based on responses from remote computing device 270 to non-rhetorical messages.

The message selection system 202 can include a response classifier 714. The similar response classifier 714 can be an application, applet, script, service, daemon, routine, or other executable logic to classify a response from a non-rhetorical message. The response classifier 714 can search through a database of responses in the message selection system 202 and generate feature sets for training or updating the models 210 of the message objects 206. The feature sets can include information pertaining to a quality score of the response to messages sent from the message selection system 202. The features sets can include times series that indicate when a message was transmitted to a remote computing device 270, when (or if) a response to the message was received, and a quality score of the response. The quality score can indicate a level of engagement the user has with a received message. The response classifier 714 can determine a quality score for the response based on a time between the transmission of the message to the remote computing device and a time when the message selection system 202 receives a response to the message. For example, the response classifier 714 can assign a high quality score to a response received within a predetermined duration of the message's transmission and a low quality score to a response received after the predetermined duration. In some implementations the quality score can be based on a time-decaying function. In some implementations, the response classifier 714 can generate a quality score based on the content of the response. For example, if the message includes an input box for the user to input text, the response classifier 714 can assign a quality score based on the amount of text entered into the input box.

The response classifier 714 can classify the response from the non-rhetorical message according to a response policy 716. The response classifier 714 can indicate whether the quality score is calculated based on a response time, an amount of interaction or engagement with a message (e.g., the amount of text entered into an input box), or a combination thereof. The response policy 716 can indicate that the quality score is time-based. For example, a response policy 716 can be based on an elapsed time from receipt, by the remote computing device 270, of the non-rhetorical message to recordation of the user's response by the reporting agent 274. For example, the remote computing device 270 can receive a message at 7 AM. The non-rhetorical message can encourage the user of the remote computing device 270 to engage in a five-minute stretching session before the user leaves for the office. The non-rhetorical message can include a button asking the user to confirm that the user engaged in the five-minute stretching session. The reporting agent 274 can receive confirmation that the user engaged in the five-minute stretching session at 7:10 AM, indicating that the user engaged in the stretching session between 7 AM and 7:10 AM, shortly after the user received the message. The response policy 716 can rank responses to non-rhetorical messages based on time. For example, a response policy 716 can rank a quick response to a non-rhetorical message more highly than a slow response to a non-rhetorical message. The response policy 716 can include a time limit for the user to respond to the message.

The response policy 716 can indicate that the quality score is engagement based. For example, a high quality score can be a response with a high level of active user engagement. A message may prompt a user to answer a few questions about the contents of the message, such as "How would you rate the activity?" and "Would you like another reminder about drinking water?" A response with active user engagement can include a response wherein the user answers a majority of the questions prompted by the message.

The message selection system 202 can include a similar message object selector 712. The similar message object selector 712 can be an application, applet, script, service, daemon, routine, or other executable logic to select message objects 206 based on a message object's similarity to another message object 206. The similar message object selector 712 can identify a rhetorical message object 206 to update. The similar message object selector 712 can select a rhetorical message object 206 for updating if the if the response evaluator 256 has not updated the model 210 in a given amount of time. For example, the similar message object selector 712 can update the models 210 every day, week, or month. The similar message object selector 712 can determine the classification of the rhetorical message object 206. The similar message object selector 712 can determine the classification of the rhetorical message object to find similar non-rhetorical message objects 206 that can be used to update the model 210 of the rhetorical message object 206.

The similar message object selector 712 can identify non-rhetorical message objects 206 that are similar to the rhetorical message object 206 being updated. The feature sets (e.g., the response data) of the non-rhetorical message objects 206 can be to update rhetorical message objects 206 of a similar classification. The similar message object selector 712 can identify non-rhetorical message objects 206 that are similar to the rhetorical message object 206 to be updated. A non-rhetorical message object 206 can be similar to a rhetorical message object 206 when the non-rhetorical message object 206 has a same classification, tag, or category as the rhetorical message object 206. For example, the similar message object selector 712 can identify a tag (e.g., breathing exercise) of a rhetorical message object 206 to be updated, and search for one or more non-rhetorical message objects 206 with the same tag. The similar message object selector 712 can identify message objects 206 that have the same tags. For example, message objects can have a "breathing exercise" tag or a "hydration" tag. The similar message object selector 712 can select non-rhetorical message objects 206 based on the non-rhetorical message object's similarity to a rhetorical message object 206. The similar message object selector 712 can identify a group of message objects 206 that have the same tags or classifications.

Referring again to the response evaluator 256, the response evaluator 256 receives information and data from the reporting agent 274 through the network 104 to generate updates to the models 210 of the message objects 206. As discussed in a previous section of the disclosure, the model 210 of the message object 206 can receive contextual data 220 as inputs and output a confidence value 242 that indicates the predicted effectiveness of a message in achieving a target value 214. The model 210 can be a machine learning model (e.g., reinforcement learning model, k-nearest neighbor model, backpropagation model, q-learning model, genetic algorithm model, neural networks, supervised learning model, or unsupervised learning model). The response evaluator 256 can train the model 210 based on feature sets generated from the responses of past responses to messages. The model 210 of each message object 206 can output a confidence value 242 indicating the confidence level of the target value 214.

The response evaluator 256 can update the model 210 of a message object 206. The message object 206 to update can be selected by the similar message object selector 712 based on a classification by the response classifier 714. The response evaluator 256 can update the model 210 of a rhetorical message object 206 based on responses that were classified by the response classifier according to a response policy 716. For example, the similar message object selector 712 can identify non-rhetorical message objects 206 with the same tag or classification as the rhetorical message objects 206 to be updated. The similar message object selector 712 can identify the message responses the message selection system 202 received in response to messages from the identified non-rhetorical message objects 206 and generate features sets that the response evaluator 256 can use to update the models 210 of the non-rhetorical message objects 206 and the rhetorical message objects 206.

The response evaluator 256 can update the model 210 of a message object 206 by training or retraining the model 210. The response evaluator can train the model 210 of a rhetorical message object 206 based on feature sets from the non-rhetorical message objects 206. As described above, the response evaluator 210 can update the model 210 of a non-rhetorical message object 206 based on the responses received to messages generated by the non-rhetorical message object 206. The response evaluator 256 can update the model 210 of a rhetorical message object 206 based on the models 210 of the message objects 206 the similar message object selector 712 identified. For example, the response evaluator 256 can import or copy a model 210 from one of the identified non-rhetorical message objects 206 into the rhetorical message object 206 that is to be updated.

The response evaluator 256 can update the model 210 of a rhetorical message object 206 based on the responses to messages generated by non-rhetorical message objects 206. For example, the similar message object selector 712 can identify a plurality of non-rhetorical message objects 206 that have a same classification as the rhetorical message object 206 being updated. The response evaluator 256 can identify a plurality of past messages and responses to the identified non-rhetorical message objects 206. The response evaluator 256 can generate features sets based on the plurality of past messages and responses to the identified non-rhetorical message objects 206. The response evaluator 256 can then train the model of the rhetorical message object 206 based on the feature sets generated from the plurality of past messages and responses to the identified non-rhetorical message objects 206.

The message selection system 202 can determine the effectiveness of rhetorical messages. The response evaluator 256 can conduct an AB test (e.g., split test or bucket test) in which a subset of users of the application 272 receive rhetorical messages and a subset of users of the application 272 do not receive rhetorical messages. In this way, the message selection system 202 can measure the effectiveness of rhetorical messages. For example, a subset (e.g., half) of the users (Group A) can receive rhetorical messages and a subset (e.g., half) of the users (Group B) can receive no rhetorical messages. The users in Group A may be different from the users in Group B. Group A can include different people who receive rhetorical messages at the same time. The message selection system 202 can hold other variables constant (e.g., number of messages sent, time of day messages are sent) to determine the effect rhetorical messages have on user engagement with the application 272 and whether rhetorical messages translate to user actions that improve health, wellbeing, and fitness. The message selection system 202 can measure the effect of rhetorical message by comparing the actions or responses of users who received rhetorical messages to those that did not receive rhetorical message.

Figure 8:
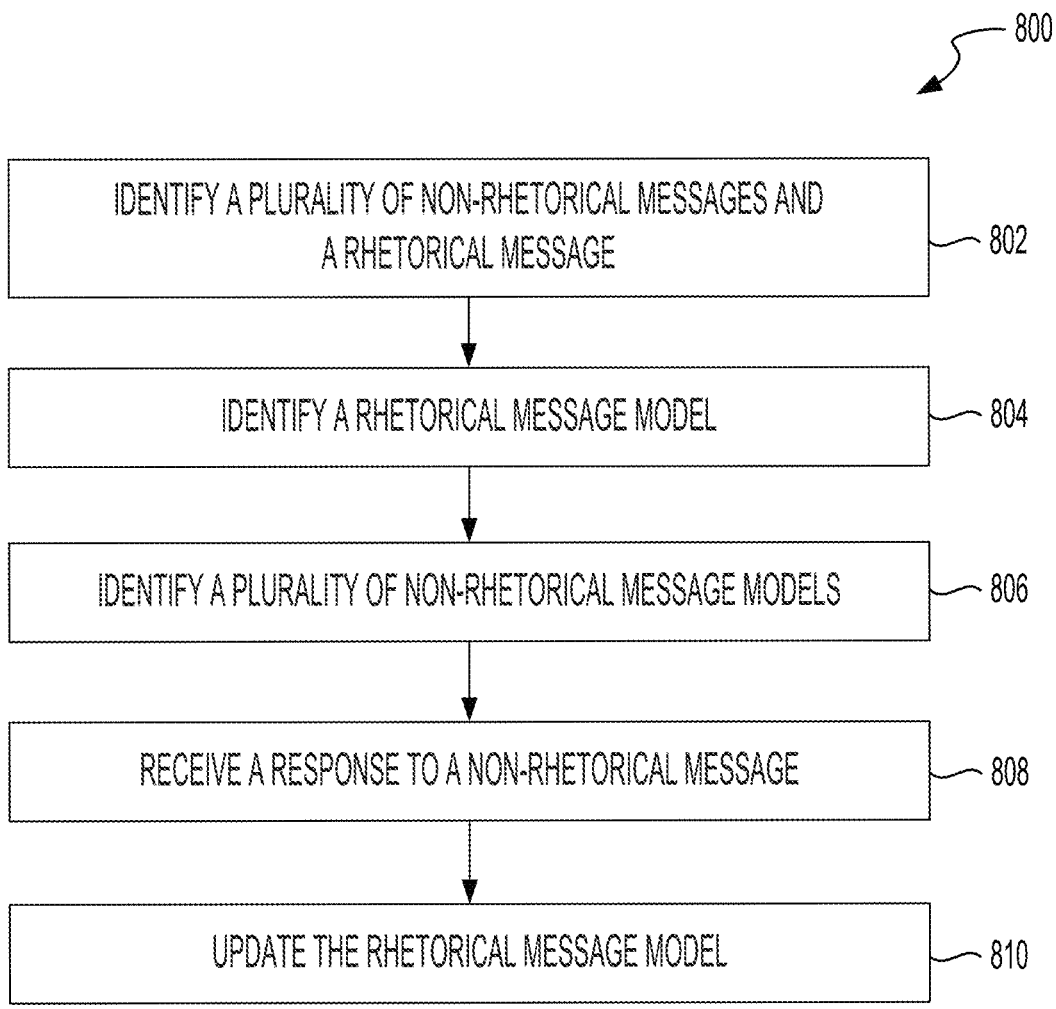
FIG. 8 illustrates a flow diagram of an example method for indirect learning model updates.

FIG. 8 illustrates a flow diagram of an example method 800 to indirectly update learning models. The method 800 can include identifying, by one or more processors of a server, a plurality of non-rhetorical messages and a plurality of rhetorical messages (BLOCK 802). The method 800 can include identifying, by the one or more processors of the server, a rhetorical message model (BLOCK 804). The method 800 can include identifying, by the one or more processors of the server, a plurality of non-rhetorical message models (BLOCK 806). The method 800 can include receiving, by the one or more processors of the server, a response message to a non-rhetorical message (BLOCK 808). The method 800 can include updating the rhetorical message model based on the received response message to the non-rhetorical message (BLOCK 810).

As set forth above, the method 800 can include identifying a plurality of non-rhetorical messages and a plurality of rhetorical messages (BLOCK 802). Non-rhetorical messages can include a message which generates a prompt for the user to respond. Rhetorical messages can include a message which does not generate a prompt for the user to responds. For example, a rhetorical message can include a message that encourages the user or a message that displays interesting facts to the user. Identifying a plurality of non-rhetorical messages and rhetorical messages can include searching through a database of messages. The non-rhetorical messages in the database can be tagged or classified by the response classifier. The rhetorical messages in the database can be tagged as rhetorical.

The method 800 can include identifying a rhetorical message model (BLOCK 804). Identifying a rhetorical message model can include identifying a message object that is tagged, grouped, or classified as a rhetorical message object and selecting or identifying the rhetorical message object's model. For example, a rhetorical message object can be categorized as a rhetorical message object with a rhetorical message model. The message selection system can identify the model of the rhetorical message object as needing to be updated. For example, the message selection system can periodically update the models of both rhetorical and non-rhetorical message objects. The messaging selection system can process through the message objects, daily, weekly, monthly, etc. to select message objects for update.

The method 800 can include identifying a plurality of non-rhetorical message models (BLOCK 806). The message selection system can identify a plurality of non-rhetorical message objects that have a same classification or grouping as the rhetorical message object (and model) being updated. For example, the message selection system can determine the rhetorical message object has a "hydration" tag and a plurality of non-rhetorical message objects that are tagged with the "hydration" tag. An indication of each of the message objects can be stored in a relational or other database. An attribute or column of the message object in the database can be a tag or classification tag. The similar message object selector can determine the tag of the rhetorical message object to be updated and query the database for non-rhetorical message objects that have the same tag.

The method 800 can include receiving a response message to a non-rhetorical message (BLOCK 808). The response evaluator can receive a response message to a non-rhetorical message generated by one of the rhetorical message objects identified at BLOCK 806. In some implementations, the response evaluator can retrieve previously responses to past messages generated by the non-rhetorical message objects identified at BLOCK 806. The response classifier can generate one or more feature sets based on the received response or historical responses to messages generated by the non-rhetorical message objects identified at BLOCK 806. For example, the features sets can indicate a time when the message was transmitted to the remote computing device, a time that the response was received, and a quality score of the response. The response classifier can also generate features sets for messages for which the message selection system did not receive a response. The features sets can include a time that the message was transmitted to the remote computing device and an indication that a response was not received.

The method 800 can include updating the rhetorical message model (BLOCK 810). The response evaluator can update the rhetorical model based on the non-rhetorical models of the identified rhetorical message objects. For example, in some implementations, the response evaluator can retrain the models of the non-rhetorical message objects using the feature sets generated in response to the received (or not received) responses as training data. The response evaluator can copy a model retrained on the updated feature sets into the rhetorical message object being updated. In some implementations, the response evaluator can update the rhetorical message model based on the received response messages to the non-rhetorical messages. For example, rather than updating a model of a non-rhetorical message object based on the responses to its messages and then copying the updated model into a rhetorical message object, the response evaluator can identify one or more feature sets generated based on responses to messages generated by the plurality of identified non-rhetorical message objects. The response evaluator can train a model of the rhetorical message object using the one or more feature sets generated based on responses to messages generated by the plurality of identified non-rhetorical message objects.

D. Systems and Methods of Selecting and Transmitting Messages Across Networked Environments Using Confidence Values A message may be presented via a computing device to notify the user, such as specifying to take a particular action or to provide information. Repeated presentation of the message, however, may cause message fatigue on the part of the user, with the user not taking any action from the presentation of the message. Message fatigue may cause a reduction in the efficacy of the message in notifying the user, thereby decreasing the quality of human-computer interaction (HCI) of the computing device in presenting the message. The reduction in efficacy may lead to waste of computational resources and network bandwidth as messages are transmitted over a network and processed by the computing device.

To address these and other challenges with message fatigue, the selection and provision of the message may be carried out on a user-by-user basis. To that end, the message selection system may maintain a set of message objects. Each message may include a template defining how a corresponding message is to be generated and a selection criterion indicating one or more endpoints (or objectives) to be achieved by serving the corresponding message. When a message is to be provided to a particular user, the message selection system may derive or identify a user state (or "intent") using an activity log of the user. The activity log may include entries indicating how the user responded to previous presentations of messages. The user state may be used to select one of the message objects to generate a corresponding message.

For each of the message objects, the message selection system may generate a confidence value indicating a likelihood that the presentation of the corresponding message to the user will achieve its objective. The message selection system may change the confidence value for the message object based on an adjustment factor, such as: an amount of time elapsed since the provision of any message to the computing device of the user, a total number of messages as indicated in a user profile that the computing device is set to receive within a predefined length of time, and a length of time the user is awake or active, among others. Using the adjusted confidence value, the message selection system may select one of the message objects. The message selection system may generate a message in accordance with the selected message object and provide to the computing device of the user. Reponses by the users may be recorded using the computing device and provided to the message selection system to be used in the next round of selection.

In this manner, the message selection system may send messages that are more likely to result on action by the user at a relevant time, thereby increasing HCI between the user and the computing device, and the efficacy of the presentation of the message on the computing device. Since the message is more likely to result in the action on the part the user, the message selection system may better utilize and reduce wasted computing resources and network bandwidth consumed in providing and presenting the messages. In addition, appropriate content delivered at the right time, tailored for each user, can have a positive effect on a user's engagement with application. Personalized and relevant messages delivered in a timely manner to each user through an application can translate to real-world actions undertaken by the user to improve health, wellbeing, fitness and overall quality of life.

Referring now to FIG. 9A, depicted is a block diagram of a system 900 for selecting and transmitting messages across networked environments using confidence values. In overview, the system 900 may include at least one message selection system 902 and one or more remote computing devices 904A-N (hereinafter generally referred to as remote computing devices 904). The message selection system 902 and the remote computing devices 904 may be communicatively coupled with one another via at least one network 906. The message selection system 902 may include at least one state tracker 908, at least one object evaluator 910, at least one model trainer 912, at least one message deliverer 914, at least one message generator 916, at least one response handler 918, at least one evaluation model 920, at least one delivery policy 922, at least one activity database 924, and at least one message database 926. The activity database 924 may maintain or include one or more activity logs 928A-N (hereinafter generally referred to as activity logs 928). The message database 926 may maintain or include one or more message objects 930A-N (hereinafter generally referred to as message objects 930). Each remote computing device 904 may have at least one application 932. The application 932 running on the remote computing device 904 may have at least one reporting agent 934. The remote computing device 904 may be associated with at least one user 936.

Each of the components in the system 900 (e.g., the message selection system 902 and its components and the remote computing device 904 and its components) may be executed, processed, or implemented using hardware or a combination of hardware, such as the system 100 detailed herein in Section A. The components of the system 900 may be also used to execute, process, or implement the functionalities detailed herein in Sections B and C. For example, the message selection system 902 may include the functions described in relation to the message selection system 202. The message object 930 maintained on the database 924 may include the functions detailed herein in conjunction with message object 206. The object evaluator 912 may include the functions of the message object evaluator 252, among others. The remote computing device 904 may include or execute the functionalities described herein in conjunction with remote computing device 270.

Referring now to FIG. 9B, depicted is a sequence diagram of the system 900 with the operations of the state tracker 908, the model trainer 910, and the object evaluator 912, among others, of the message selection system 902. The state tracker 908 executing on the message selection system 902 may access the activity database 924 to retrieve or identify the activity log 928 for one of the remote computing devices 904, applications 932, or users 936. The activity log 928 maintained on the activity database 924 may include one or more entries 940A-N (hereinafter generally referred to entries 940). Each entry 940 of the activity log 928 may identify or include at least one action by the user 936 that is recorded via the remote computing device 904 associated with the user 936. The action by the user 936 may have been in response to a previous presentation of a message via the application 932 on the remote computing device 904. For example, the application 932 running on the remote computing device 904 may detect an interaction entered by the user 936 via one or more of the user interface elements of the previous message presented on the application 932. The interaction with the user interface elements may indicate an action performed by the user 936. Upon detection, the application 932 may send an indication of the interaction to the message selection system 902 for recordation to the activity log 928 on the activity database 924. The indication may include a timestamp identifying a time at which the interaction was entered. Upon receipt, the indication from the remote computing device 904 may be stored and maintained on the activity database 924 as one of the entries 940 of the activity log 928.

With the identification from the activity database 924, the state tracker 908 may parse the activity log 928 to identify or obtain the entries 940. By identifying the entries 940, the state tracker 908 may determine, identify, or obtain the actions performed by the user 936 recorded via the remote computing device 904 as indicated in the entries 940 of the activity log 928. In some embodiments, the state tracker 908 may select or identify a subset of the entries 940 in the activity log 928 based on timestamps of the entries 940 within a defined time window. The defined time window may be relative to a current time, and may range from an hour to a month. For example, the state tracker 908 may select the subset of entries 940 of the activity log 928 from the past week as indicated in the timestamps. Upon the selection form the activity log 928, the state tracker 908 may identify the actions performed by the user 936 as indicated in each entry 940.

Based on the actions indicated in the entries 940, the state tracker 908 may identify or determine at least one user state 942 (sometimes referred herein as an "intent" or "user intent") for the user 936 of the remote computing device 904. The user state 942 may classify or identify an objective (e.g., a behavioral endpoint) expected on the part of the user 936 as inferred the actions recorded in the entries 940 of the activity log 928 on the activity database 924. The user state 942 may relate to various aspects of the use activity indicated entries 940, and may include, for example: an application navigation event (e.g., opening the application 932), an engagement pattern or interaction rate with one or more features of the application 932 completion of certain milestones in compliance with the regime provided via the application 932, and user input data from a questionnaire (e.g., related to health of user), among others. The user state 942 may be used as one of the parameters in selecting one of the message objects 930 corresponding to a message to provide for presentation to the user 936. In some embodiments, the user state 942 may correspond to the contextual data 220 as discussed in Sections B and C. In some embodiments, the state tracker 908 may select or determine the user state 942 from a set of user states 942 based on the actions identified from the activity log 928. Each user state 942 in the set may be defined as corresponding to one or more actions. For example, if the actions identified from the activity log 928 match one of the actions defined for the user state 942 in the set, the state tracker 908 may determine the corresponding user state 942 for the user 936.

In conjunction, the object evaluator 910 executing on the message selection system 902 may identify the one or more message objects 930 from the message database 926. The identified message objects 930 may serve as candidate message objects from which to select and generate a corresponding message to provide for presentation on the remote computing device 904. Each message object 930 may include a set of executable instructions (e.g., a script) to assess whether to generate and send the corresponding message for presentation to the user 936. In some embodiments, the message object 930 may correspond to the message object 206 and its components discussed above in Sections B and C.

Each message object 930 may include: at least one message template 944, at least one constraint 946, and at least one selection criterion 948, among others. The message template 944 may include instructions for generating a corresponding message to include one or more user interface elements. For example, the message template 944 may identify placeholders to insert textual or visual content in a graphical user interface element of the message to be presented via the remote computing device 904. The constraint 946 may define or include one or more restrictions for generating or transmitting the message corresponding to the message object 930. The restrictions of the constraint 946 may include, for example, one or more time windows (e.g., time of day or weekend versus weekday) during which the corresponding the message is allowed to generated and sent. The selection criterion 948 may define or include one or more endpoints to be achieved by the user 936 in presenting a message corresponding to the message object 930. The selection criterion 948 may also identify or define a time window within which the endpoints are to be achieved. The endpoints of the selection criterion 948 may include behavioral objectives expected to be achieved on the user 936, such as those to motivate the user 936 to engage with the regimen pattern to permit optimal delivery of the digital therapy provided via the application 932. The selection criterion 948 may be pre-configured or preset with the goal of incentivizing the user 936 to receive a greater efficacy of treatment. The behavioral objects defined by the selection criterion 948 may include, for example: an application navigation event (e.g., opening the application 932), a performance of a particular activity (e.g., breathing, exercising, or dieting) on the part of the user 936, and a scheduling of the activity via the application 932 (e.g., specifying a future time in which to perform exercises), among others.

For each message object 930, the object evaluator 910 may calculate, generate, or determine at least one confidence value 952 based on the user state 942 and the selection criterion 948. The confidence value 952 may identify, represent, or indicate a predictive effectiveness of the message corresponding to the message object 930 on a particular user 936 toward achieving the endpoints defined by the selection criterion 948 for the message object 930. The confidence value 952 may also indicate a predicted likelihood that the user 936 will take an action corresponding to at least one of the endpoints defined by the selection criterion 948. In determining the confidence value 952 for the message object 930, the object evaluator 910 may compare the endpoints defined by the selection criterion 948 and the user state 942 of the user 938. The user state 942 may identify the objective on the part of the user 936, and may correspond to one of the endpoints defined by the selection criterion 948. When at least one of the endpoints defined by the selection criterion 948 match or correspond to the user state 942, the object evaluator 910 may determine a relatively higher confidence value 942. Conversely, when none of the endpoints defined by the selection criterion 948 match or correspond to the user state 942, the object evaluator 910 may determine a relatively lower confidence value 942. In some embodiments, the message deliverer 914 may also remove the message object 930 from further processing.

To facilitate the determination of the confidence value 952, the model trainer 912 executing on the message selection system 902 may maintain the evaluation model 920. The evaluation model 920 may be used to determine the confidence value 952 of the message object 930. The evaluation model 920 may include, for example, a regression model (e.g., a linear regression or logistic regression models), a support vector machine (SVM), an artificial neural network (ANN), a Naïve Bayes classifier, and a classification model (e.g., k-nearest neighbor), among others. In general, the evaluation model 920 may include a set of inputs and a set of outputs related to one another via a set of weights. In some embodiments, the evaluation model 920 may be part of or dedicated to one of the message objects 930 (e.g., the model 210). In some embodiments, the evaluation model 920 may be separate from an individual message object 930 and may be general over the set of message objects 930 maintained on the message database 926.

The model trainer 912 may initiate or establish the evaluation model 920 using a training dataset. The training of the evaluation model 920 may be in accordance for the architecture of the evaluation model 920. For example, when the evaluation model 920 is a classification model, the training may be iteratively performed until convergence. The training dataset for the evaluation model 920 may include historical response data from users (e.g., the user 936) to previously presented messages. The messages in the training dataset may correspond to one or more of the message objects 930. The training dataset may include the message templates 944, the constraints 946, and the selection criteria 948 of the message objects 930 corresponding to the messages previously served to the users. The historical response data may indicate success or failure at achieving the endpoint specified by the message objects 930. In training the model, the model trainer 912 may apply the training dataset to the evaluation model 920 to generate an output indicating a success or failure. Based on a comparison of the output with the result indicated in the historical response data, the model trainer 912 may adjust or modify the weights of the evaluation model 920, and repeat the application until convergence. The modification of the weights of the evaluation model 920 may be in accordance with learning for the architecture used to implement the evaluation model 920.

With the establishment, the object evaluator 910 may apply the user state 942 and the message object 930 to the evaluation model 920 to generate or determine the confidence value 952. In some embodiments, the object evaluator 910 may factor in the message template 944, the constraint 946, and the selection criterion 948, or any combination thereof (e.g., in the feature space representation) in applying to the evaluation model 920. For example, the object evaluator 910 may use the user state 942 and the endpoints defined by the selection criterion 948 of the message object 930 to apply to the evaluation model 920. To apply, the object evaluator 910 may feed the user state 942 and the message object 930 (e.g., in their feature space representations) as inputs to the evaluation model 920. The object evaluator 910 may process the input using the weights of the evaluation model 920 to generate the output of the evaluation model 920. The object evaluator 910 may identify the output of the evaluation model 920 as the confidence value 952 for the message object 930. In general, when at least one of the endpoints defined by the selection criterion 948 correlate with the user state 942, the confidence value 942 may be relatively higher. Conversely, when none of the endpoints defined by the selection criterion 948 correlate with the user state 942, the confidence value 942 may be relatively lower.

In some embodiments, the message deliverer 914 may maintain or remove one or more of the message objects 930 from selection based on the constraints 946 defined for the message objects 930. For each message object 930, the message deliverer 914 may identify the constraint 946. As discussed above, the constraint 946 may define or include one or more restrictions (e.g., time window) for generating or transmitting the message corresponding to the message object 930. In some embodiments, the message deliverer 914 may identify a current time corresponding to a time that the message corresponding to the message object 930 is to be transmitted. The message deliverer 914 may compare the current time to the restricted time window defined by the constraint 946 of the message object 930. When the current time is not within the restricted time window defined by the constraint 946, the message deliverer 914 may maintain the message object 930 for further processing as described below. Otherwise, when the current time is within the restricted time window defined by the constraint 946, the message deliverer 914 may remove the message object 930 from further processing.

Referring now to FIG. 9C, depicted is a sequence diagram of the system 900 with the operations of the message deliverer 914 and the message generator 916, among others, of the message selection system 902. The message deliverer 914 executing on the message selection system 902 may identify or select at least one of the message objects 930 in accordance with at least one delivery policy 922. The delivery policy 922 may specify the selection of the at least one of the message object 930 based on the confidence value 952 for the message object 930, among other factors. In some embodiments, the delivery policy 922 may be particular to one of the message object 930. In some embodiments, the delivery policy 922 may be generally applicable to the set of message objects 930.

The delivery policy 922 may identify, define, or otherwise include at least one update factor 960, at least one threshold 962, and at least one delivery time 964, among others. The update factor 960 may identify or define a value or an amount by which the confidence value 952 for the message object 930 is to be modified or adjusted. In some embodiments, the update factor 960 may specify that the amount by which the confidence value 952 is to be adjusted (e.g., increase or decrease) is to be based on an amount of time elapsed since the previous provision of any message to the remote computing device 904. For example, the update factor 960 may function as the cool down policies 232 as discussed in Sections B and C. The threshold 962 may specify a value of the confidence value 952 at which the message object 930 is permitted to be selected for further processing. In some embodiments, the threshold 962 may be defined relatively over the confidence values 952 determined for the message objects 930 maintained on the message database 926. For example, the threshold 962 may specify that message objects 930 with the highest 5% of confidence values 952 are permitted to be selected for further processing. In some embodiments, the threshold 962 may function as the threshold policies 234 as discussed in Sections B and C. The delivery time 964 may specify a time or time window during which a message corresponding to one of the message objects 930 may be transmitted or provided to the remote computing device 904.

In determining which message object 930 to select, the message deliverer 914 may modify or otherwise update the confidence value 952 of each message object 930 using the update factor 960 of the delivery policy 922. In some embodiments, the message deliverer 914 may identify an amount of time elapsed between a previous time of transmission of any message corresponding to one of the message objects 930 to the remote computing device 904 and the current time. The identification of the amount of elapsed time may be identified as specified by the update factor 960 of the delivery policy 922. Based on the amount of elapsed time, the message deliverer 914 may determine the update factor 960 for the message object 930. Using the update factor 960, the message deliverer 914 may modify or update the confidence value 952 of each message object 930. For example, the message deliverer 914 may multiply the update factor 960 with the confidence value 952 to adjust the confidence value 952.

In some embodiments, in addition to the specifications of the delivery policy 922, the message deliverer 914 may maintain or remove one or more of the message objects 930 from selection based on the constraints 946 defined for the message objects 930. For each message object 930, the message deliverer 914 may identify the constraint 946. As discussed above, the constraint 946 may define or include one or more restrictions (e.g., time window) for generating or transmitting the message corresponding to the message object 930. In some embodiments, the message deliverer 914 may identify a current time corresponding to a time that the message corresponding to the message object 930 is to be transmitted. In some embodiments, the message deliverer 914 may compare the current time to the restricted time window defined by the constraint 946 of the message object 930. When the current time is not within the restricted time window defined by the constraint 946, the message deliverer 914 may maintain the message object 930 for further processing as described below. Otherwise, when the current time is within the restricted time window defined by the constraint 946, the message deliverer 914 may remove the message object 930 from further processing.

Based on the updated confidence values 952, the message deliverer 914 may identify or select at least one of the set of message objects 930. In some embodiments, the message deliverer 914 may rank the set of message objects 930 by updated confidence values 952. Using the ranking, the message deliverer 914 may select one of the message objects 930 (e.g., the message object 930 with the highest confidence value 952 in the ranking). In some embodiments, the message deliverer 914 may compare the updated confidence value 952 of the message object 930 to the threshold 962 defined in the delivery policy 922. When the confidence value 952 satisfies (e.g., greater than) the threshold 962, the message deliverer 914 may select the corresponding message object 930. Conversely, when the confidence value 952 does not satisfy (e.g., less than or equal to) the threshold 962, the message deliverer 914 may refrain from selecting the corresponding message object 930.

With the selection of the message object 930, the message generator 916 executing on the remote computing system may create or generate at least one corresponding message 916 for presentation to the user 936 of the remote computing device 904. The message generator 916 may identify the message template 944 of the selected message object 930. With the identification, the message generator 916 may parse the specification of the message template 944 to the message object 930. In parsing, the message generator 916 may execute the message template 944 to generate the message 966. Once generated, the message 966 may include one or more user interface elements 968A-N (hereinafter generally referred to as user interface elements 968). The user interface elements 968 may correspond to graphical user interface elements of the message 966 to be presented via the remote computing device 904, and may include functionality to be invoked in response to detection of an interaction by the user 936.

Referring now to FIG. 9D, depicted is a sequence diagram of the system 900 with the operations of the message generator 916 and the response handler 918, among others, of the message selection system 902 and the remote computing device 914. Upon generation, the message generator 916 may provide, send, or otherwise transmit the message 966 to the remote computing device 904 via the network 906. In some embodiments, the message deliverer 914 may compare the current time to the specified time window defined by the delivery time 964 of the delivery policy 922. When the current time is within the specified time window defined by the delivery policy 922, the message deliverer 914 may transmit the message object 930 to the remote computing device 904. Otherwise, when the current time is outside the specified time window defined by the delivery policy 922, the message deliverer 914 may wait until the current time matches the delivery time 964.

Upon receipt, the application 932 executing on the remote computing device 904 may present the message 966 for the user 936. The application 932 may configure the remote computing device 904 to communicate with the message selection system 902 via the network 906. The application 932 may parse the message 966 and present (e.g., render or playback) the message 966, including the user interface elements 968, via the remote computing device 904. As the message 966 is presented, the reporting agent 934 of the application 932 may monitor for one or more interactions with the user interface elements 968 of the message 966 via an input/output (I/O) device of the remote computing device 904. The interactions may be performed by the user 936, and may be used to record one or more activities performed by the user 936 in response to the presentation of the message 966. For example, when the message 966 presented via the remote computing device 904 indicates that the user 936 is to perform a breathing exercise, the user 936 may select a command button indicating that the breathing exercise has been performed. Based on the interaction detected on the message 966, the reporting agent 934 may generate and send at least one response 970. The response 970 may identify the one or more actions performed by the user 936 upon presentation of the message 966 that are recorded using the interactions via the remote computing device 904. The response 970 may also identify or include a timestamp corresponding to a time at which the actions were recorded on the remote computing device 904. Upon generation, the application 932 may send or transmit the response 970 to the message selection system 902 via the network 906.

The response handler 918 executing on the message selection system 902 may in turn identify or receive the response 970 from the remote computing device 904 via the network 906. The response handler 918 may parse the response 970 to identify the one or more actions performed by the user 936 as indicated in the response 970. Using the actions identified from the response 970, the response handler 918 may generate one or more entries 940'A-N (hereinafter generally referred to as entries 940') to include on the activity log 928 for the user 936. The entry 940 may identify the actions performed by the user 936 in response to the presentation of the message 966. The entry 940 may include the timestamp corresponding to the time at which the actions were recorded by the user 936 on the application 932. The response handler 918 may add or insert the new entries 940' to the activity log 928 for the user 936 maintained on the message database 924. By adding the entries 940', the response handler 918 may record the actions performed by the user 936 in response to the presentation of the message 966 via the remote computing device 904. The newly added entries 940' to the activity log 928 may be used to update the user state 942 for the user 936.

In this manner, the message selection system 902 may select and generate messages 966 that are more likely to be interacted by the user 936 associated with the remote computing device 906 at the appropriate time. The selection and generation of the messages 966 may increase the quality of the human-computer interactions (HCI) between the user 936 and the overall system 900 (including the remote computing device 904). The selection and generation may also result in the increased likelihood the behavioral endpoint or objective of the user 936. Furthermore, because the messages 966 are more likely to be read and interacted with, the message selection system 902 may better utilize and reduce wasted computing resources and network bandwidth.

Referring now to FIG. 10, depicted is a flow diagram of a method 1000 of selecting and transmitting messages across networked environments using confidence values. The method 1000 may be implemented using any of the component as detailed herein above in conjunction with FIGS. 1-9D. In brief overview, a server may obtain actions from an activity log (1005). The server may determine a user state (1010). The server may identity candidate message objects (1015). The server may determine a confidence value (1020). The server may update the confidence value by elapsed time (1025). The server may select a message object (1030). The server may generate a message (1035). The server may transmit the message (1040).

In further detail, a server (e.g., the message selection system 902) may obtain actions from an activity log (e.g., the activity log 928) (1005). The activity log may include one or more entries (e.g., the entries 940). Each entry of the activity log may identify one or more actions performed by a user (e.g., the user 936) in response to a presentation of a previous message. The server may parse the entries of the activity log to identify the one or more actions. The server may determine a user state (e.g., the user state 942) (1010). Using the identified actions, the server may determine the user state for the user. The user may indicate an objective of the user in performing the actions as recorded in the activity log. The server may also select the user state from a set of defined user states. Each user state may correspond to one or more actions performed by the user.

The server may identity candidate message objects (e.g., the message objects 930) (1015). Each message object may include a message template (e.g., the message template 944), a constraint (e.g., the constraint 946), and a selection criterion (e.g., the selection criterion 948), among others. The message template may specify the generation of a corresponding message and user interface elements on the message. The constraint may specify conditions restricting selection of the message object. The selection criterion may define one or more endpoints to be achieved in presenting a message corresponding to the message object.

The server may determine a confidence value (e.g., the confidence value 952) (1020). To determine the confidence value for each message object, the server may compare the user state with the endpoints defined by the selection criterion of the message object. The confidence value may indicate a predictive effectiveness of the corresponding message on the user toward achieving the endpoints identified by the selection criterion for the message object. The server may also apply the message object and the user state on an evaluation model (e.g., the evaluation model 920) to generate the confidence value. The server may update the confidence value by elapsed time (1025). The server may modify the confidence value based on a time elapsed since a previous presentation of a message to the user. The server may increase or decrease the confidence value based on the elapsed time.

The server may select a message object (1030). The server may select one of the message objects based on the confidence values. The server may compare the confidence value for the message object with a threshold (e.g., the threshold 962). When the confidence value satisfies the threshold, the server may select the message object. Otherwise, when the confidence value does not satisfy the threshold, the server may refrain from selecting the message object. The server may generate a message (e.g., the message 966) (1035). Using the template of the selected message object, the server may generate the message. The message may include one or more user interface elements (e.g., the user interface elements 968). The server may transmit the message (1040). The message may be transmitted to a remote computing device (e.g., the remote computing device 904). Upon receipt, the remote computing device may present the message.

E. Systems and Methods of Selecting and Transmitting Messages of Different Types Across Networked Environments Repeated presentation of the message, however, may cause message fatigue on the part of the user, with the user not taking any action from the presentation of the message and lead a reduction in the efficacy of the message in notifying the user. This may lead to the decrease in the quality of human-computer interaction (HCI) of the computing device in presenting the message. The reduction in efficacy may lead to waste of computational resources and network bandwidth as messages are transmitted over a network and processed by the computing device. This may be especially problematic when assessing or evaluating the performance of messages that may include information for the user but may not be configured to receive any input via user interface elements (sometimes herein referred to as rhetorical messages). With messages configured to receive input via user interface element (sometimes herein referred to as non-rhetorical messages), the performance score of such messages may be determined based on the recorded responses. In contrast, with messages not configured to receive any input, there may be no record of the responses to the messages.

To address these and other technical challenges with assessing the efficacy of messages, the performance scores of messages with recorded responses may be used to estimate the predicted performance scores of message lacking user interface elements. The message selection system may identify a set of message objects with recorded responses to the corresponding messages. Each message object may define an endpoint to be achieved on the part of the user in presenting the corresponding message. The message selection system may compare the responses from the users to the endpoints of the message object. From the comparison, the message selection system may determine a number of users that satisfied the endpoint of the message object corresponding to the message that were presented to the users.

Based on the number of users, the message selection system may determine a performance score for each message object. The performance score may indicate a degree of effectiveness of presenting the message to the user. With the determination, the message selection system may rank the message objects by the performance scores. Using the ranking, the message selection system may select a set of message objects to permit for use in generating messages for transmission. The message selection system may also select another set of message object to restrict from use in generating messages. From the set of permitted message objects, the message selection system may identify another message object lacking ability to record responses due to the configuration without any input elements. The identification of the other message objects may be based on corresponding endpoints. The message selection system may add the identified message objects to the set of permitted message objects.

In this manner, the message selection system may expand the set of messages capable of generation and provision to remote computing devices, thereby augmenting the functionality of the messages. The expansion of messages may increase the quality of human-computer interactions (HCI) between the user and the remote computing device. In addition, since the messages are more likely to result in an action on the part of the user (even if not recorded), the message selection system may better utilize and reduce wasted computing resources and network bandwidth consumed in providing and presenting the messages.

Referring now to FIG. 11A, depicted is a block diagram of a system 1100 for selecting and transmitting messages of different types across networked environments using confidence values. In overview, the system 1100 may include at least one message selection system 1102 and one or more remote computing devices 1104A-N (hereinafter generally referred to as remote computing devices 1104). The message selection system 1102 and the remote computing devices 1104 may be communicatively coupled with one another via at least one network 1106. The message selection system 1102 may include at least one response tracker 1108, at least one object evaluator 1110, at least one model trainer 1112, at least one delivery controller 1114, and at least one message correlator 1116, at least one performance model 1118, at least one response database 1120, and at least one message database 1122, among others. The response database 1120 may maintain or include response data 1124A-N (hereinafter generally referred to as response data 1124). The message database 1122 may maintain or include a set of message objects 1126A-N of one type (hereinafter generally referred to as message objects 1126) and another set of message objects of another type 1126'A-N (hereinafter generally referred to as message objects 1126'). Each remote computing device 1104 may include at least one application 1128. The application 1128 running on the remote computing device 1104 may include at least one reporting agent 1130. The remote computing device 1104 may be associated with at least one user 1132.

Each of the components in the system 1100 (e.g., the message selection system 1102 and its components and the remote computing device 1104 and its components) may be executed, processed, or implemented using hardware or a combination of hardware, such as the system 100 detailed herein in Section A. The components of the system 1100 may be also used to execute, process, or implement the functionalities detailed herein in Sections B and C. For example, the message selection system 1102 may include the functions described in relation to the message selection system 202. The message object 1126 or 1126' maintained on the database 1120 may include the functions detailed herein in conjunction with message object 206. The object evaluator 1110 may include the functions of the message object evaluator 252, among others. The remote computing device 1104 may include or execute the functionalities described herein in conjunction with remote computing device 270.

Referring now to FIG. 11B, depicted is a sequence diagram of the system 1100 with the operations of the response tracker 1108, the object evaluator 1110, and the model trainer 1112, among others, of the message selection system 1102. The response tracker 1108 executing on the message selection system 1102 may access the response database 1120 to retrieve or identify response data 1112. The response data 1112 may include one or more entries 1140A-N (hereinafter generally referred to entries 1140) across one or more of the remote computing devices 1104, the applications 1126, or the users 1130. In some embodiments, the response tracker 1108 may identify a subset of the entries 1140 from the response data 1124 within a time window. The time window may be defined relative to the present time, and may range between an hour to a month. Response data 1124 gathered from the time window may be used to evaluate or assess the performance of the messages corresponding to message objects 1126 previously presented to the users 1130.

Each entry 1140 (sometimes referred herein as a response) of the response data 1120 may identify or include at least one action by the user 1132 that is recorded via the remote computing device 1104 associated with the user 1132. The action by the user 1132 may have been in response to a previous presentation of a message via the application 1128 on the remote computing device 1104. For example, the application 1128 running on the remote computing device 1104 may detect an interaction entered by the user 1132 via one or more of the user interface elements of the previous message presented on the application 1128. The previous message may have been generated using the message object 1126 of the first type. The interaction with the user interface elements may indicate an action performed by the user 1132. Upon detection, the application 1128 may send an indication of the interaction to the message selection system 1102 for recordation to the response data 1124 on the response database 1120. The indication may include a timestamp identifying a time at which the interaction was entered. Upon receipt, the indication from the remote computing device 1104 may be stored and maintained on the response database 1120 as one of the entries 1140 of the response data 1124.

In some embodiments, the response tracker 1108 may identify or determine a user state (sometimes referred herein as an "intent" or "user intent") for each user 1132 using the entries 1140 of the response data 1112 for the user 1132. The determination of the user state by the response tracker 1108 in the same manner as the determination of the user state 942 by the state tracker 908 as discussed above. The user state may classify or identify an objective (e.g., a behavioral endpoint) expected on the part of the user 1132 as inferred the actions recorded in the entries 1140 of the response data 1124. The user state may relate to various aspects of the use activity indicated entries 1140 include, for example: an application navigation event (e.g., opening the application 1128), an engagement pattern or interaction rate with one or more features of the application 1128 completion of certain milestones in compliance with the regime provided via the application 1128, and user input data from a questionnaire (e.g., related to health of user), among others. In some embodiments, the response tracker 1108 may determine the user state for the user 1132 prior to the presentation of the message by using a subset of entries 1140 prior to the presentation. The subset of entries 1140 from the response data 1124 may include, for example, the those used in selecting the message or a set number of entries 1140 prior to the presentation of the message. The response tracker 1108 may identify the entries 1140 prior to the presentation based on the timestamps of the entries 1140. In some embodiments, the response tracker 1108 may select or determine the user state from a set of user states based on the actions identified from the response data 1124. Each user state in the set may be defined as corresponding to one or more actions.

The object evaluator 1110 executing on the message selection system 1102 may identify the one or more message objects 1126 of the first type (sometimes referred herein as a non-rhetorical type) from the message database 1122. Each message object 1126 may include a set of executable instructions (e.g., a script) to assess whether to generate and send the corresponding message 1146 for presentation to the user 1132. In some embodiments, the message object 1126 may correspond to the message object 206 and its components discussed above in Sections B and C. In some embodiments, the object evaluator 1110 may identify the message objects 1126 of the first type.

Each message object 1126 may include: at least one message template 1142 and at least one selection criterion 1144, among others. The message template 1142 may include instructions for generating at least one corresponding message 1146 of the first type to include one or more user interface elements. For example, the message template 1142 may identify placeholders to insert textual or visual content in a graphical user interface element of the message to be presented via the remote computing device 1104. The selection criterion 1144 may define or include one or more endpoints to be achieved by the user 1132 in presenting the message 1146 corresponding to the message object 1126. The selection criterion 1144 may also identify or define a time window within which the endpoints are to be achieved. The endpoints of the selection criterion 1144 may include, for example, behavioral objectives expected to be achieved on part of the user 1132, such as those described above with respect to the behavioral objectives defined by the selection criterion 948. The selection criterion 1144 may also indicate which actions are to be performed by the user 1132 to satisfy one or more of the endpoints.

The message template 1142 of each message object 1126 of the first type may correspond to or may be used to generate at least one message 1146. For message objects 1126 of the first type, each message 1146 may include: one or more non-interactive elements 1148A-N (hereinafter generally referred to as non-interactive elements 1148) and one or more interactive elements 1150A-N (hereinafter generally referred to as interactive elements 1150). Each non-interactive element 1148 may lack a configuration to respond to detected interactions by the user 1132 when presented via the remote computing device 1104. The non-interactive elements 1148 may also lack the configuration to record the interactions by the user 1132. In contrast, each interactive element 1150 may have a configuration to respond to detected interactions by the user 1132 when presented via the remote computing device 1104. The interactive elements 1150 may also have the configuration to record the interactions by the user 1132 and to communicate the detected interactions with the message selection system 1102.

For each message object 1126, the object evaluator 1110 may identify the response data 1124 recording actions performed by users 1130 when presented with the message 1146 corresponding to the message object 1126. In identifying the response data, the object evaluator 1110 may access the response database 1120 to identify one or more of the entries 1140 of the response data 1124 corresponding to responses to the presentation of the corresponding message 1146. In each identified entry 1140, the object evaluator 1110 may identify an input by the user 1132 on one or more of the interactive elements 1152 of the message 1146. The input may be recorded via an interaction with one of the interactive elements 1152 on the message 1146. The input may also indicate the action performed by the user 1132 recorded via the remote computing device 1104 when presented with the corresponding message 1146. In some embodiments, the object evaluator 1110, in conjunction with the response tracker 1108, may parse the entry 1140 to identify the recorded action performed by the user 1132.

Based on the inputs from each entry 1140 for the message object 1126, the object evaluator 1110 may determine whether at least one of the endpoints defined by the selection criterion 1144 of the message object 1126 is satisfied. To determine, the object evaluator 1110 may compare the action indicated in the entry 1140 with the endpoint defined by the selection criterion 1144 of the message object 1126. As discussed above, the selection criterion 1144 of the message object 1126 may specify the one or more actions to be performed by the user 1132 to satisfy the defined endpoint. In some embodiments, the object evaluator 1110 may traverse through the entries 1140 for the message object 1126 in comparing the action with the endpoint.

When the action identified from the entry 1140 match one of the actions specified by the endpoint of the selection criterion 1144, the object evaluator 1110 may determine that at least one of the endpoints for the message object 1126 is satisfied. From the determination, the object evaluator 1110 may count or determine the number of users 1130 for each message object 1126 that satisfied at least one of the endpoints specified by the selection criterion 1144 of the message object 1126. Conversely, when the action identified from the entry 1140 does not match any of the actions specified by the endpoint of the selection criterion 1144, the object evaluator 1110 may determine that none of the endpoints for the message object 1126 is satisfied. From the determination, the object evaluator 1110 may count or determine the number of users 1130 for each message object 1126 that did not satisfy any of the endpoints specified by the selection criterion 1144 of the message object 1126.

Using the number of users 1130 that satisfied at least one of the endpoints defined by the selection criterion 1144 of the message object 1126, the object evaluator 1110 may calculate, generate, or determine at least one performance score 1154 for the message object 1126. In some embodiments, the number of users 1130 that did not satisfy any endpoint defined by the selection criterion 1144 of the message object in determining the performance score 1154. The performance score 1152 may identify, represent, or indicate an effectiveness of the corresponding message 1146 in achieving the endpoints defined by the selection criterion 1144. The performance score 1152 may also indicate a proportion of users 1130 that satisfied one or more endpoints defined by the selection criterion 1144 of the message object 1126. In some embodiments, the object evaluator 1110 may use a function (e.g., a weighted average) to determine the performance score 1152. The function may factor in the number of users 1130 that satisfied at least one of the endpoints and the number of users 1130 that did not satisfy any of the endpoints, among other factors. In general, when the number of users that are determined to have satisfied at least one of the endpoints defined by the selection criterion 1144 of the message object 1142 is higher, the performance score 1152 may be relatively higher. Conversely, when the number of users that are determined to have satisfied at least one of the endpoints defined by the selection criterion 1144 of the message object 1142 is lower, the performance score 1152 may be relatively lower.

In some embodiments, in determining the performance score 1152, the object evaluator 1110 may compare the user state for the user 1132 associated with the entry 1140 prior to the presentation of the corresponding message 1146 with the endpoint defined for the corresponding message object 1126. When the user state matches or corresponds to at least one of the endpoints defined in the selection criterion 1144 for the message object 1126, the object evaluator 1110 may determine a relatively higher performance score 1152. Conversely, when the user state does not match or correspond to any of the endpoints defined by the selection criterion 1144 for the message object 1126, the object evaluator 1110 may determine a relatively lower performance score 1152.

To facilitate the determination of the performance score 1152, the model trainer 1112 executing on the message selection system 1102 may maintain the performance model 1118. The performance model 1118 may be used to determine the performance score 1152 of the message object 1126. The performance model 1118 may include, for example, a regression model (e.g., a linear regression or logistic regression models), a support vector machine (SVM), an artificial neural network (ANN), a Naïve Bayes classifier, and a classification model (e.g., k-nearest neighbor), among others. In general, the performance model 1118 may include a set of inputs and a set of outputs related to one another via a set of weights. In some embodiments, the performance model 1118 may be part of or dedicated to one of the message objects 1126 (e.g., the model 210). In some embodiments, the performance model 1118 may be separate from an individual message object 1126 and may be general over the set of message objects 1126 (and the message objects 1126').

The model trainer 1112 may initiate or establish the performance model 1118 using a training dataset. The training of the performance model 1118 may be in accordance for the architecture of the performance model 1118. For example, when the performance model is a classification model, the training may be iteratively performed until convergence. The training dataset for the performance model 1118 may include historical response data from users (e.g., the user 1132) to previously presented messages. The messages in the training dataset may correspond to one or more of the message objects 1130. The training dataset may include the message templates 1142 and the selection criteria 1144 of the message objects 1130 corresponding to the messages previously served to the users. The historical response data may indicate success or failure at achieving the endpoint specified by the message objects 1130. In training the model, the model trainer 1112 may apply the training dataset to the performance model 1118 to generate an output indicating a success or failure. Based on a comparison of the output with the result indicated in the historical response data, the model trainer 1112 may adjust or modify the weights of the performance model 1118, and repeat the application until convergence. The modification of the weights of the performance model 1118 may be in accordance with learning for the architecture used to implement the performance model 1118.

In some embodiments, the model trainer 1112 may use at least a portion of the response data 1124 to modify or update the performance model 1118. The application of the response data 1124 may be prior to, in conjunction with, or subsequent to the determination of the performance score 1152. The training of the performance model 1118 using the response data 1124. In some embodiments, at least a portion of the response data 1124 may be included as part of the training dataset. In some embodiments, the model trainer 1112 may update the performance model 1118 based on the determination of whether the endpoint defined by the message object 1126 is satisfied using the entries 1140 of the response data 1124. For example, in training, the model trainer 1112 may apply the entries 1140 to the performance model 1118 to generate an output indicating a success or failure. Based on a comparison of the output with the determination of whether the endpoint is satisfied, the model trainer 1112 may adjust or modify the weights of the performance model 1118, and repeat the application until convergence. The modification of the weights of the performance model 1118 may be in accordance with learning for the architecture used to implement the performance model 1118.

With the establishment of the performance model 1118, the object evaluator 1110 may apply the response data 1124 identified for the message object 1126 to determine the performance score 1152. In some embodiments, the object evaluator 1110 may also factor in the message template 1142 and the selection criterion 1144 of the message object 1126 in determining the performance score 1152. In some embodiments, the object evaluator 1110 may also factor in the user state determined from the entries 1140 for the message object 1126. To apply, the object evaluator 1110 may feed the entries 1140 of the response data 1124 identified for the message object 1126 and the message object 1126 itself as inputs of the performance model 1118. The object evaluator 1110 may process the input using the weights of the performance model 1118 to generate the output of the performance model 1118. The object evaluator 1110 may identify the output of the performance model 1118 as the performance score 1152 for the message object 1126. In general, when the number of users that are determined to have satisfied at least one of the endpoints defined by the selection criterion 1144 of the message object 1142 is higher, the performance score 1152 may be relatively higher. Conversely, when the number of users that are determined to have satisfied at least one of the endpoints defined by the selection criterion 1144 of the message object 1142 is lower, the performance score 1152 may be relatively lower.

In some embodiments, the object evaluator 1110 may assign or attribute one or more additional endpoints to the selection criterion 1144 of at least one of the message objects 1126 based on the response data 1124 for the message object 1126. The object evaluator 1110 may identify the user state from the entry 1140 prior to the presentation of the message 1146 corresponding to the message object 1126. Based on the identification of the user state, the object evaluator 1110 may identify an endpoint corresponding to the user state. In some embodiments, the object evaluator 1110 may select the endpoint from a set of defined endpoints using the user state. The set may define a mapping between the user state and one or more of the endpoints to include into the selection criterion 1144. The mapping may be defined in the message object 1126 or the message database 1122. Upon finding a match between the user state and one or more of the endpoints, the object evaluator 1110 may add or insert the endpoints into the definition of the selection criterion 1144 of the message object 1126. In some embodiments, the object evaluator 1110 may add the identified endpoints, when the performance score 1152 for the message object 1126 satisfies (e.g., greater than or equal to) a threshold score. The threshold score may demarcate a value for the performance score 1152 at which to add endpoints to the selection criterion 1144 of the message object 1126.

Referring now to FIG. 11C, depicted is a sequence diagram of the system 1100 with the operations of the deliver controller 1114, among others, of the message selection system 1102. The delivery controller 1114 executing on the message selection system 1102 may to determine whether to assign or include each message object 1126 into a permitted set 1160 or a restricted set 1162 based on the corresponding performance score 1152. Both the permitted set 1160 and the restricted set 1162 may be maintained on the message selection system 1102 (e.g., with the message database 1122). Message objects 1126 assigned to the permitted set 1160 may be allowed to be selected for generation and provision to the remote computing devices 1104. In some embodiments, the message objects 1126 assigned to the permitted list 1160 may be more likely (e.g., weighted higher) to be selected for generation and provision for presentation via the remote computing devices 1104. On the other hand, message objects 1126 assigned to the restricted set 1162 may be restricted or prevented from selection for generation and transmission to the remote computing devices 1104. In some embodiments, the message objects 1126 assigned to the restrict set 1162 may be less likely (e.g., weighted lower) for selection to be generated and provided for presentation of the remote computing devices 1104.

To determine the assignment, the delivery controller 1114 may rank the message objects 1126 based on the performance scores 1152. The ranking of the message objects 1126 may be in accordance with a sort algorithm, such as an insertion sort, a merge sort, a heap sort, a quick sort, a bubble sort, a radix sort, or a bucket sort, among others. Based on the ranking, the delivery controller 1114 may assign the message object 1126 to the permitted set 1160 or to the restricted set 1162. In some embodiments, the delivery controller 1114 may select a subset of message objects 1126 with the highest n performance scores 1152 to assign to the permitted set 1160 and may assign the remaining message objects 1126 to the restricted set 1162. In some embodiments, conversely, the delivery controller 11144 may select a subset of message objects 1126 with the lowest n performance scores 1152 to assign to the restricted set 1162 and may assign the remaining message objects 1126 to the permitted set 1160.

In some embodiments, the delivery controller 1114 may determine the assignments of the message objects 1126 based on a comparison between the performance scores 1152 and a threshold score. The threshold score may demarcate a value of the performance score 1152 at which to assign the corresponding to the message object 1126 to the permitted set 1160 or to the restricted set 1162. When the performance score 1152 of the message object 1126 is determined to satisfy (e.g., greater than or equal to) the threshold score, the delivery controller 1114 may assign the message object 1126 to the permitted set 1160. Conversely, when the performance score 1152 of the message object 1126 is determined to not satisfy (e.g., less than) the threshold score, the delivery controller 1114 may assign the message object 1126 to the restricted set 1162. Based on the assignment to the permitted set 1160 or the restricted set 1162, the message selection system 1102 may determine whether to generate and send messages 1148 (e.g., in the manner described in Section D).

Referring now to FIG. 11D, depicted is a sequence diagram of the system 1100 with the operations of the message correlator 1116, among others, of the message selection system 1102. The message correlator 1116 executing on the message selection system 1102 may identify the one or more message objects 1126' of the second type (sometimes referred herein as a rhetorical type). Each message object 1126' may include a set of executable instructions (e.g., a script) to assess whether to generate and send the corresponding message 1146' for presentation to the user 1132. In some embodiments, the message object 1126' may correspond to the message object 206 and its components discussed above in Sections B and C.

Each message object 1126' may include: at least one message template 1142' and at least one selection criterion 1144', among others. The message template 1142' may include instructions for generating at least one corresponding message 1146' of the first type to include one or more user interface elements. For example, the message template 1142' may identify placeholders to insert textual or visual content in a graphical user interface element of the message to be presented via the remote computing device 1104. The selection criterion 1144' may define or include one or more endpoints to be achieved by the user 1132 in presenting the message 1146' corresponding to the message object 1126'. The selection criterion 1144' may also identify or define a time window within which the endpoints are to be achieved. The endpoints of the selection criterion 1144' may include, for example, behavioral objectives expected to be achieved on the user 1132. The selection criterion 1144' may also indicate which actions are to be performed by the user 1132 to satisfy one or more of the endpoints.

The message template 1142' of each message object 1126' of the second type may correspond to or may be used to generate at least one message 1146'. For message objects 1126' of the second type, each message 1146' may one or more non-interactive elements 1148'A-N (hereinafter generally referred to as non-interactive elements 1148). Unlike messages 1146 generated from the message objects 1126 of the first type, the message 1146' generated from the message object 1126' of the second type may lack one or more interactive elements 1150. Each non-interactive element 1148' may lack a configuration to respond to detected interactions by the user 1132 when presented via the remote computing device 1104. The non-interactive elements 1148' may also lack the configuration to record the interactions by the user 1132. Because of the configuration, the message 1146' may further lack the capability of sending back recorded interactions to the message selection system 1102. For example, when the message 1146' is provide to the remote computing device 1104, the application 1128 may present the message 1146' to the user 1132. The application 1128 may parse the message 1146' and present (e.g., render or playback) the message 1146', including the non-interactive elements 1148. While the message 1146' is presented, the reporting agent 1130 of the application 1128 may monitor interactions with the message 1146'. Since the message 1146' lacks the configuration to report back responses to the message selection system 1102, the reporting agent 1130 may be prevented from returning a response.

The message correlator 1116 may determine or identify at least one correspondence 1170 between one of the message objects 1126 of the first type in the permitted set 1160 with at least one message object 1126' of the second type. The correspondence 1170 may indicate that the message object 1126 and message object 1126' have similar or matching endpoints defined in the selection criterion 1144 and selection criterion 1144' respectively. The identification of the correspondence 1170 may be based on the selection criterion 1144 of the message object 1126 of the first type and the selection criterion 1144' of the message object 1126' of the second type. In some embodiments, the message correlator 1116 may compare the selection criterion 1144 of each message object 1126 with the selection criterion 1144' of the message object 1126'. When the selection criterion 1144 is determined to not match, the message correlator 1116 may determine or identify a lack of the correspondence 1170 between the message object 1126 and the message object 1126'. In addition, the message correlator 1116 may identify another message object 1126 from the permitted set 1160 to compare against. In some embodiments, the message correlator 1116 may include the message object 1126' into the restricted list 1162.

Otherwise, when the selection criterion 1144 is determined to match, the message correlator 1116 may determine or identify the correspondence 1170 between the message object 1126 and the message object 1126'. With the identification of the correspondence 1170, the message correlator 1116 may select the message object 1126' to include into the permitted set 1160. In some embodiments, the message correlator 1116 may select a subset of the message object 1126' determined to have the correspondence 1170 with one of the message objects 1126 in the permitted set 1160. With the selection, the message correlator 1116 may include the subset of the message objects 1126' of the second type into the permitted list 1160 along with the message object 1126 of the first type. By including to the permitted set 1160, the message objects 1126' may be allowed to be selected for generation and provision to the remote computing devices 1104. In some embodiments, the message objects 1126' assigned to the permitted list 1160 may be more likely (e.g., weighted higher) to be selected for generation and provision for presentation via the remote computing devices 1104.

Referring now to FIG. 12, depicted is a flow diagram of a method 1200 of selecting and transmitting messages of different types across networked environments using confidence values. The method 1200 may be implemented using any of the component as detailed herein above in conjunction with FIGS. 1-9D. In brief overview, a server may identify message objects of a first type (1205). The server may determine a number of users satisfying an endpoint (1210). The server may determine a performance score (1215). The server may rank message objects by performance scores (1220). The server may permit or restrict message objects (1225). The server identify corresponding message objects of a second type (1230).

In further detail, a server (e.g., the message selection system 1102) may identify message objects of a first type (e.g., message objects 1126) (1205). Each message object may include a message template (e.g., the message template 1142) and a selection criterion (e.g., the selection criterion 1144), among others. The message template may specify the generation of a corresponding message and user interface elements on the message. The selection criterion may define one or more endpoints to be achieved in presenting a message corresponding to the message object.

The server may determine a number of users (e.g., the user 1132) satisfying an endpoint (1210). To determine, the server may identify response data (e.g., the response data 1124) including entries (e.g., the entries 1140) for each message object. From each entry, the server may identify the action performed by the user. With the identification, the server may compare the action with the endpoint specified by the message object. When the action matches the endpoint, the server may increment the number of users satisfying the endpoint.

The server may determine a performance score (e.g., the performance score 1154) (1215). Based on the number of users satisfying the endpoint, the server may calculate the performance score for each message object. In some embodiments, the server may use a performance model (e.g., the performance model 1116) to determine the performance score. The server may rank message objects by performance scores (1220). The server may compare the performance scores of the message objects to a threshold value.

The server may permit or restrict message objects (1225). Based on the ranking, the server may permit or restrict message objects. For example, the server may select the top ranking message objects as permitted, while restricting the remainder of message objects. Message objects identified as permitted may be allowed or more likely to be used to generate and transmit corresponding messages (e.g., the message 1146). Message objects identified as restricted may be prevented or less likely to be used to generate and transmit corresponding messages.

The server identify corresponding message objects of a second type (e.g., the message objects 1126') (1230). The message objects of the second type may have a message template (e.g., the message template 1144') specifying the lack of interactive elements (e.g., the interactive elements 1150). The server may identify the message object of the second type as corresponding to the message object of the first type when the endpoints of the two message objects match.

While the disclosure has been described with respect to specific embodiments, one skilled in the art will recognize that numerous modifications are possible. For instance, although specific examples of rules (including triggering conditions and/or resulting actions) and processes for generating suggested rules are described, other rules and processes can be implemented. Embodiments of the disclosure can be realized using a variety of computer systems and communication technologies including but not limited to specific examples described herein.

Embodiments of the present disclosure can be realized using any combination of dedicated components and/or programmable processors and/or other programmable devices. The various processes described herein can be implemented on the same processor or different processors in any combination. Where components are described as being configured to perform certain operations, such configuration can be accomplished, e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present disclosure may be encoded and stored on various computer readable storage media; suitable media include magnetic disk or tape, optical storage media such as compact disk (CD) or DVD (digital versatile disk), flash memory, and other non-transitory media. Computer readable media encoded with the program code may be packaged with a compatible electronic device, or the program code may be provided separately from electronic devices (e.g., via Internet download or as a separately packaged computer-readable storage medium).

While this specification contains many specific embodiment details, these should not be construed as limitations on the scope of any inventions or of what may be claimed, but rather as descriptions of features specific to particular embodiments of particular inventions. Certain features described in this specification in the context of separate embodiments can also be implemented in combination in a single embodiment. Conversely, various features described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain embodiments, multitasking and parallel processing may be advantageous.

Having described certain embodiments of the methods and systems, it will now become apparent to one of skill in the art that other embodiments incorporating the concepts of the invention may be used. It should be understood that the systems described above may provide multiple ones of any or each of those components and these components may be provided on either a standalone machine or, in some embodiments, on multiple machines in a distributed system. The systems and methods described above may be implemented as a method, apparatus or article of manufacture using programming and/or engineering techniques to produce software, firmware, hardware, or any combination thereof. In addition, the systems and methods described above may be provided as one or more computer-readable programs embodied on or in one or more articles of manufacture. The term "article of manufacture" as used herein is intended to encompass code or logic accessible from and embedded in one or more computer-readable devices, firmware, programmable logic, memory devices (e.g., EEPROMs, ROMs, PROMs, RAMs, SRAMs, etc.), hardware (e.g., integrated circuit chip, Field Programmable Gate Array (FPGA), Application Specific Integrated Circuit (ASIC), etc.), electronic devices, a computer readable non-volatile storage unit (e.g., CD-ROM, floppy disk, hard disk drive, etc.). The article of manufacture may be accessible from a file server providing access to the computer-readable programs via a network transmission line, wireless transmission media, signals propagating through space, radio waves, infrared signals, etc. The article of manufacture may be a flash memory card or a magnetic tape. The article of manufacture includes hardware logic as well as software or programmable code embedded in a computer readable medium that is executed by a processor. In general, the computer-readable programs may be implemented in any programming language, such as LISP, PERL, C, C++, C #, PROLOG, or in any byte code language such as JAVA. The software programs may be stored on or in one or more articles of manufacture as object code.

Thus, although the disclosure has been described with respect to specific embodiments, it will be appreciated that the disclosure is intended to cover all modifications and equivalents within the scope of the following claims.

What is claimed is:

1. A method of selecting messages to transmit across networked environments, comprising:
    maintaining, by at least one server having one or more processors:
        (i) a first plurality of message objects of a first message type, each message object of the first plurality of message objects associated with of a plurality of endpoints to be achieved and having a first respective message template including one or more input elements; and
        (ii) a second plurality of message objects of a second message type, each message object of the second plurality of message objects associated with at least one of the plurality of endpoints to be achieved and having a second respective message template lacking any input elements, each of the second plurality of message objects having a respective association with one or more of the first plurality of message objects;
    determining, by the at least one server for each message object of the first plurality of message objects, a number of users associated with a plurality of remote computing devices that satisfied at least one of the plurality of endpoints of the message object via input on the one or more input elements of a corresponding message when presented via the plurality of remote computing devices;
    determining, by the at least one server for each first message object of the first plurality of message objects, a corresponding performance score based on the number of users that were presented with the corresponding message and that satisfied at least one of the plurality of behavior endpoints of the first message object;
    selecting, by the at least one server, based on the performance score for each message object of the first plurality of message objects, at least a first subset of message objects from the first plurality of message objects to be used to generate messages for transmission to the plurality of remote computing devices; and
    identifying, by the at least on server, from the second plurality of message objects of the second message type, a second subset of message objects to be used to generate the messages for transmission, each of the second subset of message objects having the association with at least one of the first subset of messages objects and having the second respective message template lacking any input elements.

2. The method of claim 1, further comprising receiving, by the at least one server, response data for each first message object of the first plurality of message objects of the first message type via the input on the one or more input elements of the corresponding message for message object when presented on the plurality of remote computing devices.

3. The method of claim 1, wherein identifying the second subset of message objects from the second plurality of message objects further comprises identifying the second subset of message objects from the second plurality of message objects based on one or more of the plurality of endpoints to be achieved associated with the subset of the first plurality of message objects of the first message type.

4. The method of claim 1, further comprising:
for each first message object of the first plurality of message objects:
identifying, by the at least one server, in each response to a message corresponding to the first message object when presented on one of the plurality of remote computing devices, the input on the one or more input elements of the corresponding message; and
determining, by the at least one server, for each response to the corresponding message, that at least one of one or more of the plurality of endpoints of the first message object is satisfied based on the input on the one or more input elements of the message, and
wherein determining the number of users further comprises determining the number of users based on the determination, for each first message object of the first plurality of message objects, that at least one of the plurality of endpoints of the first message object is satisfied.

5. The method of claim 1, further comprising establishing, by the at least one server, a performance model for determining performance scores using a training dataset, the training dataset including historical response data from users for one or more of the first plurality of message objects, and
wherein determining the performance score further comprises applying the performance model to responses received from the plurality of remote computing devices responsive to the presentation of the corresponding message.

6. The method of claim 1, further comprising:
determining, by the at least one server, for each first message object of the first plurality of message objects, that at least one of the plurality of endpoints of the first message object is satisfied based on the input on the one or more input elements of the message corresponding to the first message object; and
updating, by the at least one server, a performance model for determining performance scores using the determination, for each first message object of the first plurality of message objects, that at least one of the plurality of endpoints of the first message object is satisfied.

7. The method of claim 1, further comprising attributing, by the at least one server, one or more of the plurality of endpoints to each first message object of the first plurality of message objects based on responses received from the plurality of remote computing devices responsive to the presentation of the corresponding message.

8. The method of claim 1, further comprising restricting, by the at least one server, remaining subset of the first plurality of message objects based on a comparison between the performance scores and a threshold value, the threshold value defined by a message selection policy.

9. The method of claim 1, wherein selecting the first subset of message objects from the first plurality of message objects further comprises transmission of a plurality of messages corresponding to the first subset of the first plurality of message objects across the plurality of remote computing devices.

10. A system for selecting messages to transmit across networked environments, comprising:
at least one server having one or more processors coupled with memory, configured to:
maintain:
(i) a first plurality of message objects of a first message type, each message object of the first plurality of message objects associated with of a plurality of endpoints to be achieved and having a first respective message template including one or more input elements; and
(ii) a second plurality of message objects of a second message type, each message object of the second plurality of message objects associated with at least one of the plurality of endpoints to be achieved and having a second respective message template lacking any input elements, each of the second plurality of message objects having a respective association with one or more of the first plurality of message objects;
determine, for each first message object of the first plurality of message objects, a number of users associated with a plurality of remote computing devices that satisfied at least one of the plurality of endpoints of the message object via input on the one or more input elements of a corresponding message when presented via the plurality of remote computing devices;
determine, for each first message object of the first plurality of message objects, a corresponding performance score based on the number of users that were presented with the corresponding message and that satisfied at least one of the plurality of behavior endpoints of the first message object;
select, based on the performance score for each first message object of the first plurality of message objects, at least a first subset of message objects from the first plurality of message objects to be used to generate messages for transmission to the plurality of remote computing devices
identify, using from the second plurality of message objects of the second message type, a second subset of message objects to be used to generate the messages for transmission, each of the second subset of message objects having the association with at least one of the first subset of messages objects and having the second respective message template lacking input elements.

11. The system of claim 10, wherein the at least one server is further configured to receive response data for each first message object of the first plurality of message objects of the first message type via the input on the one or more input elements of the corresponding message for message object when presented on the plurality of remote computing devices.

12. The system of claim 10, wherein the at least one server is further configured to:
identify the second subset of message objects from the second plurality of message objects based on one or more of the plurality of endpoints to be achieved associated with the subset of the first plurality of message objects of the first message type.

13. The system of claim 10, wherein the at least one server is further configured to:
for each first message object of the first plurality of message objects:
identify, in each response to a message corresponding to the first message object when presented on one of the plurality of remote computing devices, the input on the one or more input elements of the corresponding message; and
determine, for each response to the corresponding message, that at least one of one or more of the plurality of endpoints of the first message object is satisfied based on the input on the input elements of the message, and
determine the number of users based on the determination, for each first message object of the first plurality of message objects, that at least one of one or more of the plurality of endpoints of the first message object is satisfied.

14. The system of claim 10, wherein the at least one server is further configured to:
establish a performance model for determining performance scores using a training dataset, the training dataset including historical response data from users for one or more of the first plurality of message objects, and
determine the performance score by applying the performance model to responses received from the plurality of remote computing devices responsive to the presentation of the corresponding message.

15. The system of claim 10, wherein the at least one server is further configured to
determine, for each first message object of the first plurality of message objects, that at least one of one or more of the plurality of endpoints of the first message object is satisfied based on the input on the one or more input elements of the message corresponding to the first message object; and
update a performance model for determining performance scores using the determination, for each first message object of the first plurality of message objects, that at least one of the plurality of endpoints of the first message object is satisfied.

16. The system of claim 10, wherein the at least one server is further configured to attribute one or more of the plurality of endpoints to each first message object of the first plurality of message objects based on responses received from the plurality of remote computing devices responsive to the presentation of the corresponding message.

17. The system of claim 10, wherein the at least one server is further configured to restrict a remaining subset of the first plurality of message objects based on a comparison between the performance scores and a threshold value, the threshold value defined by a message selection policy.

18. The system of claim 10, wherein the at least one server is further configured to permit transmission of a plurality of messages corresponding to the first subset of message objects from the first plurality of message objects across the plurality of remote computing devices.

19. The method of claim 1, further comprising transmitting, by the at least one server, for presentation on a remote computing device, a message generated using one of the first subset of message objects from the first plurality of message objects of the first message type or the second subset of message objects from the second plurality of message objects of the second message type.

20. The system of claim 10, wherein the at least one server is further configured to transmit, for presentation on a remote computing device, a message generated using one of the first subset of message objects from the first plurality of message objects of the first message type or the second subset of message objects from the second plurality of message objects of the second message type.

* * * * *